(12) United States Patent
Heimerl

(10) Patent No.: US 11,810,675 B2
(45) Date of Patent: Nov. 7, 2023

(54) COMPUTER SYSTEM FOR GROUP CRISIS-STATE DETECTION AND INTERVENTION

(71) Applicant: Kristen M. Heimerl, Minnetonka, MN (US)

(72) Inventor: Kristen M. Heimerl, Minnetonka, MN (US)

(73) Assignee: Kristen M. Heimerl, Minnetonka, MN (US)

( * ) Notice: Subject to any disclaimer, the term of this patent is extended or adjusted under 35 U.S.C. 154(b) by 395 days.

(21) Appl. No.: 17/140,884

(22) Filed: Jan. 4, 2021

(65) Prior Publication Data

US 2021/0217532 A1     Jul. 15, 2021

Related U.S. Application Data

(60) Provisional application No. 63/054,230, filed on Jul. 20, 2020, provisional application No. 62/959,858, filed on Jan. 10, 2020.

(51) Int. Cl.
```
A61B 5/16         (2006.01)
G16H 50/30        (2018.01)
H04M 1/72421      (2021.01)
A61B 5/00         (2006.01)
G16H 40/67        (2018.01)
```
(Continued)

(52) U.S. Cl.
CPC ........... *G16H 50/30* (2018.01); *A61B 5/0004* (2013.01); *A61B 5/0022* (2013.01); *A61B 5/01* (2013.01); *A61B 5/024* (2013.01); *A61B 5/026* (2013.01); *A61B 5/08* (2013.01); *A61B 5/11* (2013.01); *A61B 5/117* (2013.01); *A61B 5/14517* (2013.01); *A61B 5/165* (2013.01); *A61B 5/7264* (2013.01); *A61B 5/742* (2013.01); *A61B 5/7405* (2013.01); *G06Q 50/265* (2013.01); *G16H 20/70* (2018.01); *G16H 40/67* (2018.01);

(Continued)

(58) Field of Classification Search
CPC .................... G01N 2800/7004; G08B 31/00
See application file for complete search history.

(56) References Cited

U.S. PATENT DOCUMENTS

| 6,934,954 | B1 | 8/2005 | Crites et al. |
| 9,313,634 | B2 | 4/2016 | Suzuki et al. |

(Continued)

OTHER PUBLICATIONS

[No author listed], "Workplace violence: a growing threat, or growing in awareness?" SHRM Better Workplaces Better World, Mar. 2019, 5 pages.

(Continued)

*Primary Examiner* — Benyam Haile
(74) *Attorney, Agent, or Firm* — Barnes & Thornburg LLP

(57) ABSTRACT

The disclosed technology provides a system and a computer implemented method for crisis state detection and intervention of a person or group of persons, the method comprising: providing a computer system designed to detect and intervene non-normal, elevated crisis operating states; using one or more sensors that ascertains a crisis state via physical, behavioral, or cognitive indicators; deducing, with computational hardware, the operational state of a user or users from one or more sensors; and administering an immediate, dual intervention of a sensory form to de-escalate the crisis operating state of a person or group of persons.

20 Claims, 35 Drawing Sheets

(51) Int. Cl.
| | |
|---|---|
| A61B 5/01 | (2006.01) |
| A61B 5/024 | (2006.01) |
| A61B 5/026 | (2006.01) |
| A61B 5/08 | (2006.01) |
| A61B 5/11 | (2006.01) |
| A61B 5/117 | (2016.01) |
| A61B 5/145 | (2006.01) |
| G06Q 50/26 | (2012.01) |
| G16H 20/70 | (2018.01) |
| G16H 50/20 | (2018.01) |
| G16Y 10/60 | (2020.01) |
| H04M 1/27453 | (2020.01) |

(52) U.S. Cl.
CPC ............ *G16H 50/20* (2018.01); *G16Y 10/60* (2020.01); *H04M 1/72421* (2021.01); *H04M 1/27453* (2020.01)

(56) References Cited

U.S. PATENT DOCUMENTS

| | | | |
|---|---|---|---|
| 9,566,411 | B1 | 2/2017 | Sherpa et al. |
| 10,191,537 | B2 | 1/2019 | Tanaka et al. |
| 10,339,781 | B2 | 7/2019 | Kaplan et al. |
| 10,692,606 | B2 | 6/2020 | Bender et al. |
| 2016/0189149 | A1* | 6/2016 | MacLaurin ...... G06Q 20/40145 705/44 |
| 2016/0342905 | A1* | 11/2016 | Ghose ................. G06Q 50/01 |
| 2017/0039045 | A1 | 2/2017 | Abraham et al. |
| 2017/0171614 | A1* | 6/2017 | el Kaliouby ........... G16H 50/70 |
| 2017/0341746 | A1* | 11/2017 | Erickson ............... B64C 39/024 |
| 2017/0347907 | A1 | 12/2017 | Le et al. |
| 2020/0089939 | A1* | 3/2020 | Rodriguez Bravo ... H04L 67/10 |
| 2020/0286505 | A1* | 9/2020 | Osborne ................. G06N 3/08 |
| 2021/0217533 | A1 | 7/2021 | Heimerl |

OTHER PUBLICATIONS

[No author listed], "Workplace violence: a growing threat, or growing in awareness?" SHRM Better Workplaces Better World, retrieved on Aug. 4, 2020, 1 page.

AdAge.com [online], "5 consumer trends that will endure after covid-19, and what they mean for marketers," Apr. 2020, retrieved on Aug. 4, 2020. retrieved from URL <https://adage.com/article/cmo-strategy/5-consumer-trends-will-endure-after-covid-19-and-what-they-mean-marketers/2247986>, 14 pages.

AGreeenStore.com [online], "FeverWatch body temperature SMART monitor bracelet bluetooth heartrate—a green store," retrieved on Jul. 31, 2020 retrieved from URL<https://agreenstore.com/products/feverwatch-body-temperature-smart-monitor-bracelet-ecg-sleep-waterproof-bluetooth-heartrate>, 10 pages.

Amazon.com [online], "Room temperature monitor," retrieved on Jul. 31, 2020, retrieved from URL <https://www.amazon.com/Room-Temperature-monitor/s?k=Room+Temperature+Monitor>, 4 pages.

AnxietyCentre.com [online], "Change in body temperature caused by anxiety," Feb. 2020, retrieved on Jul. 30, 2020, retrieved from URL<https://www.anxietycentre.com/anxiety-disorders/symptoms/change-in-body-temperature/>, 4 pages.

Bailey, "Looking back to the future: the re-emergence of green care," BJPsych International, Nov. 2017,14(4):79.

BehavioralEconomics.com [online], "Herd Behavior," retrieved on Jul. 29, 2020, 4 pages, retrieved from URL <https://www.behavioraleconomics.com/resources/mini-encyclopedia-of-be/herd-behavior/>, 4 pages.

BeyondIntractability.org [online] "The necessity of social structural change," Jul. 2003, retrieved on Jul. 31, 2020, retrieved from URL <https://www.beyondintractability.org/ssay/social_structural_changes>, 12 pages.

Blog.Bonus.ly [online], "21 expert antidotes for a toxic work environment," Jan. 27, 2016, retrieved on Aug. 4, 2020, retrieved from URL, <https://blog.bonus.ly/20-expert-antidotes-for-a-toxic-work-environment/>, 29 pages.

BusinessInsider.com [online] "Employees at the world's largest hedge fund use iPads to rate each other's performance in real-time—see how it works," Sep. 2017, retrieved on Aug. 4, 2020, retrieved from URL <https://www.businessinsider.com/bridgewater-ray-dalio-radical-transparency-app-dots-2017-9>, 26 pages.

Businesswire.com [online] "New Survey Reveals Toxic Cultures and Negative Behaviors Are Prevalent in the Workplace," Nov. 2019, retrieved on Jul. 31, 2020, retrieved from <https://www.businesswire.com/news/home/20191120005080/en/New-Survey-Reveals-Toxic-Cultures-%20Negative-Behaviors> 3 pages.

CBC.ca [online], "Green space improves mental health, well-being: Researchers found exposure to green space improved well-being both immediately and over time," Jun. 2014, retrieved on Jul. 31, 2020, retrieved from URL <https://www.cbc.ca/news/health/green-space-improves-mental-health-well-being-1.2672323>, 6 pages.

CDC.gov [online], "Violence in the workplace," Jul. 1996, retrieved on Jul. 30, 2020, retrieved from URL <https://www.cdc.gov/niosh/docs/96-100/introduction.html>, 3 pages.

Chatelaine.com [online], "The toxic effects of workplace stress," Sep. 2018, retrieved on Jul. 31, 2020, retrieved from URL <https://www.chatelaine.com/health/wellness/the-toxic-effects-of-workplace-stress/>, 6 pages.

Colenberg et al., "The relationship between interior office space and employee health and well-being—a literature review," Building Research & Information, Jan. 2020, 16 pages.

Conoley et al., "Integrating positive psychology into family therapy: Positive family therapy," The Counseling Psychologist, Jul. 2015, 43(5):703-733.

ControlServices.com [online], "What is Building Automation," retrieved on Aug. 4, 2020, retrieved from URL<http://www.controlservices.com/learning_automation.htm>, 7 pages.

Damousis et al., "Four machine learning algorithms for biometrics fusion: A comparative study," Applied Computational Intelligence and Soft Computing, Jan. 2012, 2012:8 pages.

Developers.facebook.com [online] "Best Practices on Instant Games," retrieved on Jul. 31, 2020, retrieved from URL <https://developers.facebook.com/docs/games/monetization/best-practices>, 21 pages.

En.wikipedia.org [online], "Toxic workplace," Mar. 2020, retrieved on Jul. 30, 2020, retrieved from URL <https://en.wikipedia.org/wiki/Toxic_workplace>, 4 pages.

Especialneeds.com [online] "Sensory Rooms, explained," Feb. 2019, retrieved on Jul. 31, 2020, retrieved from URL <https://www.especialneeds.com/blog/landing-pages/sensory-rooms/>, 15 pages.

Evans, "The built environment and mental health," Journal of Urban Health: Bulletin of the New York Academy of Medicine, Dec. 2003, 80(4):536-555.

Fitnessprofessionalonline.com [online], "Using group heart rate monitoring to improve results and sales of group HIIT Training," Jan. 2015, retrieved Jul. 30, 2020, retrieved from URL <https://www.fitnessprofessionalonline.com/articles/expert-advice/using-group-heart-rate-monitoring-to-improve-results-and-sales-of-group-hiit-training/>, 9 pages.

Forbes.com [online], "How does lighting affect mental health in the workplace," Dec. 2018, retrieved on Jul. 31, 2020, retrieved from URL <https://www.forbes.com/sites/pragyaagarwaleurope/2018/12/31/how-does-lighting-affect-mental-health-in-the-workplace/?sh=340ff4cc4ccd>, 5 pages.

Forbes.com [online], "Why breaking down hierarchies will get the most out of talent," Jan. 14, 2019, retrieved on Jul. 31, 2020, retrieved from URL <https://www.forbes.com/sites/jasondownes1/2019/01/14/why-breaking-down-hierarchies-will-get-the-most-out-of-talent/?sh=75f83c0c1bc3>, 5 pages.

Georgiou et al., "Can wearable devices accurately measure heart rate variability? A systematic review," Folia Medica, Feb. 2018, 60(1):15 pages.

Gonzalez et al., "Hair cortisol measurement by an automated method," Scientific Reports, Jun. 2019, 9(1):1-6.

(56) References Cited

OTHER PUBLICATIONS

Han et al., "Bergamot (*Citrus bergamia*) essential oil inhalation improves positive feelings in the waiting room of a mental health treatment center: A pilot study," Phytotherapy Research, May 2017, 31(5):812-816.
Hashoul et al., "Sensors for detecting pulmonary diseases from exhaled breath," European Respiratory Review, Jun. 2019, 28(152):13 pages.
Hcamag.com [online], "Five biggest drivers of workplace stress—and how to fight them," Apr. 2019, retrieved on Aug. 4, 2020, retrieved from URL <https://www.hcamag.com/au/news/general/five-biggest-drivers-of-workplace-stress-and-how-to-fight-them/165110>, 6 pages.
Healey et al., "Detecting stress during real-world driving tasks using physiological sensors," IEEE Journals & Magazine, Jun. 2005, 6(2):28 pages.
heart.org [online] Spend time in nature to reduce stress and anxiety, Aug. 2018, retrieved on Jul. 30, 2020, retrieved from URL <https://www.heart.org/en/healthy-living/healthy-lifestyle/stress-management/spend-time-in-nature-to-reduce-stress-and-anxiety>, 6 pages.
Herborn et al., "Skin temperature reveals the intensity of acute stress," Physiology & Behavior, Dec. 2015, 152:225-230.
Howard et al., "Expectancies, not aroma, explain impact of lavender aromatherapy on psychophysiological indices of relaxation in young healthy women," British Journal of Health Psychology, Nov. 2008, 13:603-617.
Hr.com [online] "Preventing toxic workplaces: The role of values, training, and leadership in promoting a positive workplace culture," Nov. 2019, retrieved on Jul. 31, 2020, retrieved from URL <https://www.hr.com/en/resources/free_research_white_papers/hrcom-preventing-toxic-workplaces-2019-research_k2nrdqt2.html>, 21 pages.
Inc.com [online], "4 devastating consequences of a toxic workplace culture when fear permeates an organization, its leaders are living on borrowed time," retrieved on Aug. 4, 2020, retrieved from URL <https://www.inc.com/tanya-prive/4-devastating-consequences-of-a-toxic-workplace-culture.html>, 4 pages.
Inc.com [online], "8 best industries for starting a business in 2020," Feb. 4, 2020, retrieved on Aug. 4, 2020, retrieved from URL <https://www.inc.com/best-industries-2020.html>, 11 pages.
Itoh et al., "Development of an exhaled breath monitoring system with semiconductive gas sensors, a gas condenser unit, and gas chromatograph columns," Sensors, Nov. 2016, 16(11):16 pages.
Kim et al., "Emotion recognition system using short-term monitoring of physiological signals," Medical and Biological Engineering and Computing, May 2004, 42(3):419-27.
Kutlu et al., "Effects of aroma inhalation on examination anxiety," Teaching and Learning in Nursing, Oct. 2008, 3(4):125-130.
Lansisalmi et al., "Collective stress and coping in the context of organizational culture," European Journal of Work and Organizational Psychology, Dec. 2000, 9(4):527-559.
Liang et al., "Real-time detection of driver cognitive distraction using support vector machines," IEEE Transactions on Intelligent Transportation Systems, Jun. 2007, 8(2):340-350.
Loriol et al., "Collective forms of coping and the social construction of work stress among industrial workers and police officers in France," Theory & Psychology, Feb. 2016, 26(1):112-129.
Macworld.com [online], "Apple Watch Series 3 vs Fitbit Versa 2: Even a two-year-old Apple Watch is hard to beat," Nov. 22, 2019, retrieved on Jul. 30, 2022, retrieved from URL <https://www.macworld.com/article/233301/fitbit-versa-2-vs-apple-watch-series-3-specs-features-price.html>, 13 pages.
Mayoclinic.org [online], "Thermometers: understand the options," Nov. 2020, retrieved on Jul. 31, 2020, retrieved from URL <https://www.mayoclinic.org/diseases-conditions/fever/in-depth/thermometers/art-20046737?p=1>, 4 pages.
McKinsey & Company, "AI, automation, and the future of work: ten things to solve for," Prepared for the Tech4good Summit, Organized by The French Presidency, Jun. 2018, 7 pages.
McLaughlin et al., "Developing an organization culture to facilitate radical innovation," International Journal of Technology Management, Oct. 2008, 44:27 pages.
Mental illness in the workplace: Psychological disability management, Harder et al., Jul. 2014, 406 pages (abstract only).
MindTools.com [online], "Why Good Employees Go Bad—#MTtalk Roundup," Aug. 2016, retrieved on Jul. 31, 2020, retrieved from URL <https://www.mindtools.com/blog/mttalk-good-employees-bad/>, 5 pages.
Motivations for promotion and prevention, Molden et al., in Handbook of motivation science, Jan. 2008, chapter 11:169-87.
Musicant et al., "Supervised learning by training on aggregate outputs," Seventh IEEE International Conference on Data Mining, Oct. 2007, 10 pages.
Nam et al., "Monitoring of heart and breathing rates using dual cameras on a smartphone," PloS one, Mar. 2016, 11(3):15 pages.
Nytimes.com [online], "The Unbearable heaviness of Clutter," Jan. 2019, retrieved on Aug. 4, 2020, retrieved from URL <https://www.nytimes.com/2019/01/03/well/mind/clutter-stress-procrastination-psychology.html>, 2 pages.
Padilla et al., "The toxic triangle: Destructive leaders, susceptible followers, and conducive environments," The Leadership Quarterly, Jun. 2007, 18(3):176-194.
PaintedBrain.org [online], "Aromatherapy and mental wellbeing," Jun. 2019, retrieved on Jul. 31, 2020, retrieved from <https://paintedbrain.org/news/aromatherapy-and-mental-wellbeing/>, 6 pages.
Picard et al., "Toward machine emotional intelligence: Analysis of affective physiological state," IEEE Transactions on Pattern Analysis and Machine Intelligence, Oct. 2001, 23(10):1175-1191.
ProgressFocusedApproach.com [online], "Approach/avoidance and promotion/prevention," available on or before Feb. 5, 2015, via Internet Archive: Wayback Machine URL <http://web.archive.org/web/20150205034025/http://www.progressfocusedapproach.com/approachavoidance-and-promotionprevention/>, retrieved on Jul. 31, 2020, URL <http://www.progressfocusedapproach.com/approachavoidance-and-promotionprevention/>, 2 pages.
Psychologicalscience.org [online], "The slippery-slope effect: minor misdeeds lead to major ones," Mar. 2015, retrieved on Jul. 31, 2020, retrieved from URL <https://www.psychologicalscience.org/news/minds-business/the-slippery-slope-effect-minor-misdeeds-%20lead-to-major-ones.html>, 8 pages.
Sciencedaily.com [online], "Stressed? Take a 20-minute 'nature pill'," Apr. 2019, retrieved on Jul. 30, 2020, retrieved from URL <https://www.sciencedaily.com/releases/2019/04/190404074915.htm>, 3 pages.
Stress.org [online], "42 worrying workplace stress statistics," Sep. 25, 2019, retrieved on Jul. 31, 2020, retrieved from URL <https://www.stress.org/42-worrying-workplace-stress-statistics>, 29 pages.
Supportz.com [online], "5 free android apps that function as thermometers," Dec. 2014, retrieved on Jul. 31, 2020, retrieved from URL <https://supportz.com/5-free-android-apps-that-function-as-thermometers/> 9 pages.
torbenrick.eu [online], "Top 30+ key obstacles to innovation," Sep. 2014, retrieved on Aug. 4, 2020, retrieved from URL <https://www.torbenrick.eu/blog/strategy/30-key-obstacles-to-innovation/>, 5 pages.
TowardsDatascience.com [online] "K-means Clustering: Algorithm, Applications, Evaluation Methods, and Drawbacks," Sep. 2018, retrieved from <https://towardsdatascience.com/k-means-clustering-algorithm-applications-evaluation-methods-and-drawbacks-aa03e644b48a>, 15 pages.
Unbc.ca [online], "Harder, Dr. Henry," retrieved on Jul. 31, 2020, retrieved from <https://www2.unbc.ca/people/harder-dr-henry>, 2 pages.
Van den Bosch M et al., "Environmental exposures and depression: biological mechanisms and epidemiological evidence," Annual Review of Public Health, Jan. 2019, 40:239-259.
Vice.com [online], "Watching fish swim is an odd but effective way to relax," Feb. 2018, retrieved on Jul. 31, 2020, retrieved from <https://www.vice.com/en/article/qvep4q/aquarium-therapy-good-for-health>, 15 pages.
Weeks, Aesthetics and interior design: effects on overall mental health, Rocky Mountain Products, retrieved on Jul. 31, 2020, 8 pages.

(56) References Cited

OTHER PUBLICATIONS

Wells et al., "Associations of hair cortisol concentration with self-reported measures of stress and mental health-related factors in a pooled database of diverse community samples," Stress, Jul. 2014, 17(4):334-342.
Welsh, III et al., "ILJS" International journal of leadership studies, Winter 2011, 7(1):142 pages.
What Is "Positive Family Therapy?" Peseschkian, Dec. 2012, 340 pages (abstract only).
Whywelikethis-ca.com [online], "Top 8 best body temperature fitness trackers," retrieved on Jul. 31, 2020, retrieved from URL <https://www.whywelikethis-ca.com/top-8-best-body-temperature-fitness-trackers/>, 16 pages.
Wikipedia.org [online], "Interface (computing)," May 2020, retrieved on Jul. 31, 2020, retrieved from URL <https://en.wikipedia.org/wiki/Interface_(computing), 5 pages.
Wojtusiak, "Model Learning from Published Aggregated Data," Learning Structure and Schemas from Documents, Sep. 2011, 3:375:369.
Wright et al., "Hair cortisol analysis: A promising biomarker of HPA activation in older adults," The Gerontologist, Jun. 2015, 55(S1):140-145.
Yu et al., "Driving distraction analysis by ECG signals: an entropy analysis," In International Conference on Internationalization, Design and Global Development, Jul. 2011, 258-264.
Zimbardo, "A situationist perspective on the psychology of evil: Understanding how good people are transformed into perpetrators," in The Social Psychology of Good and Evil, 1st ed., Miller (ed)., Apr. 6, 2005, chapter 2, 16 pages.

\* cited by examiner

FIG. 1

3 Things Affect Our Stress Levels:
1. Personal Factors
2. Physical Environment Factors
3. Social Environment Factors

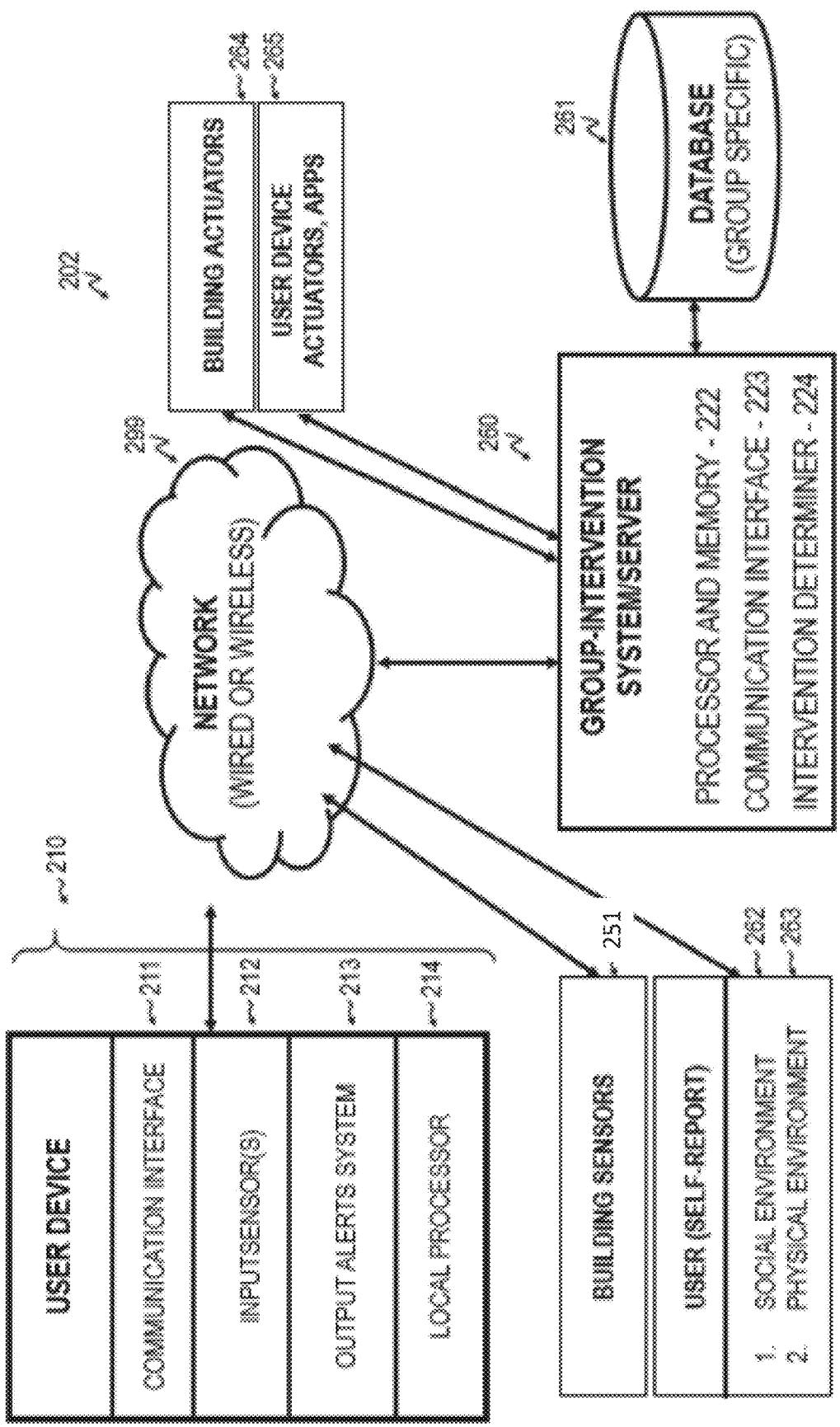
FIG. 4 — *GROUP-CRISIS-STATE DETECTION AND INTERVENTION SYSTEM*

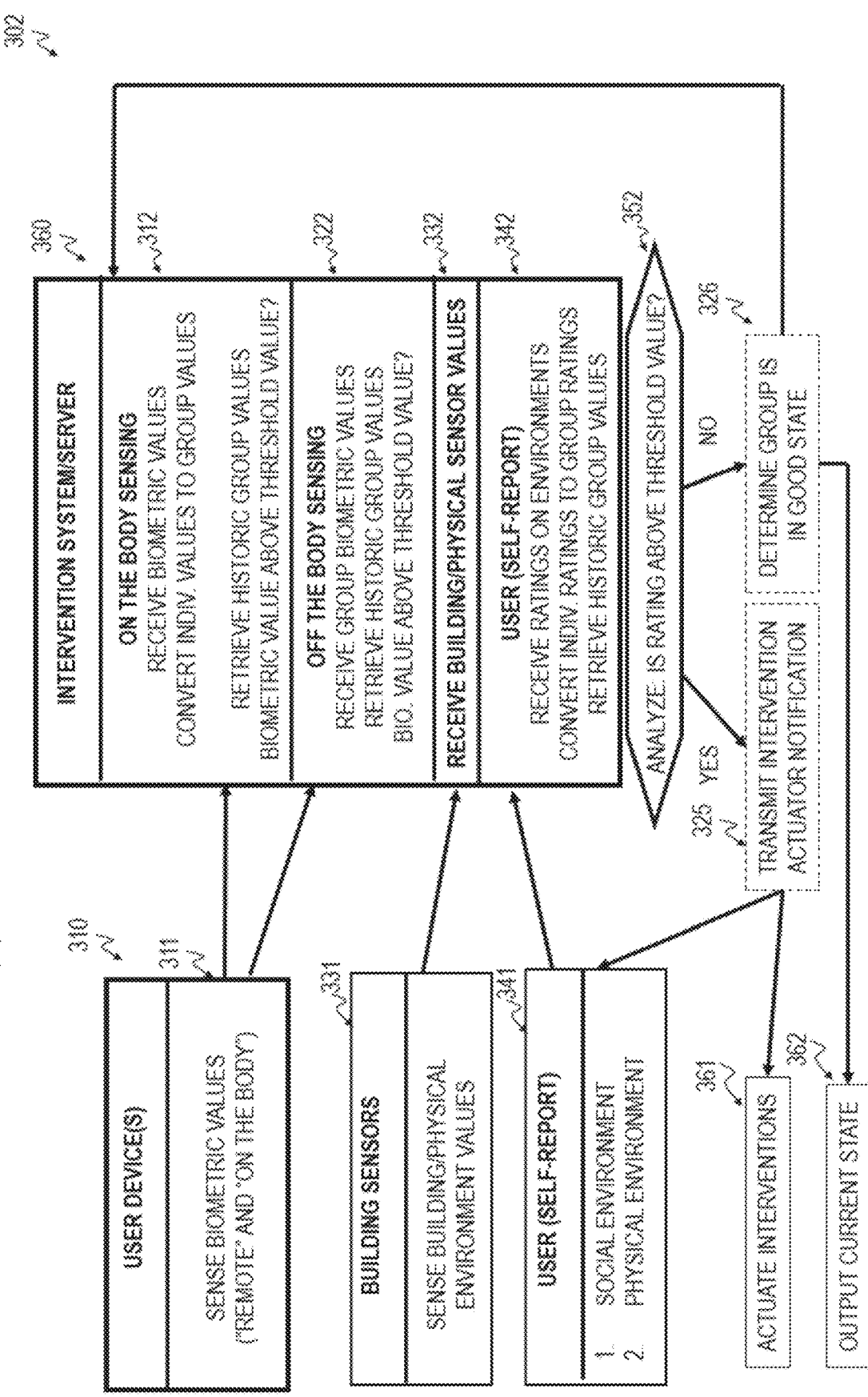
FIG. 5 — USER DEVICE(S) AND INTERVENTION SYSTEM/SERVER

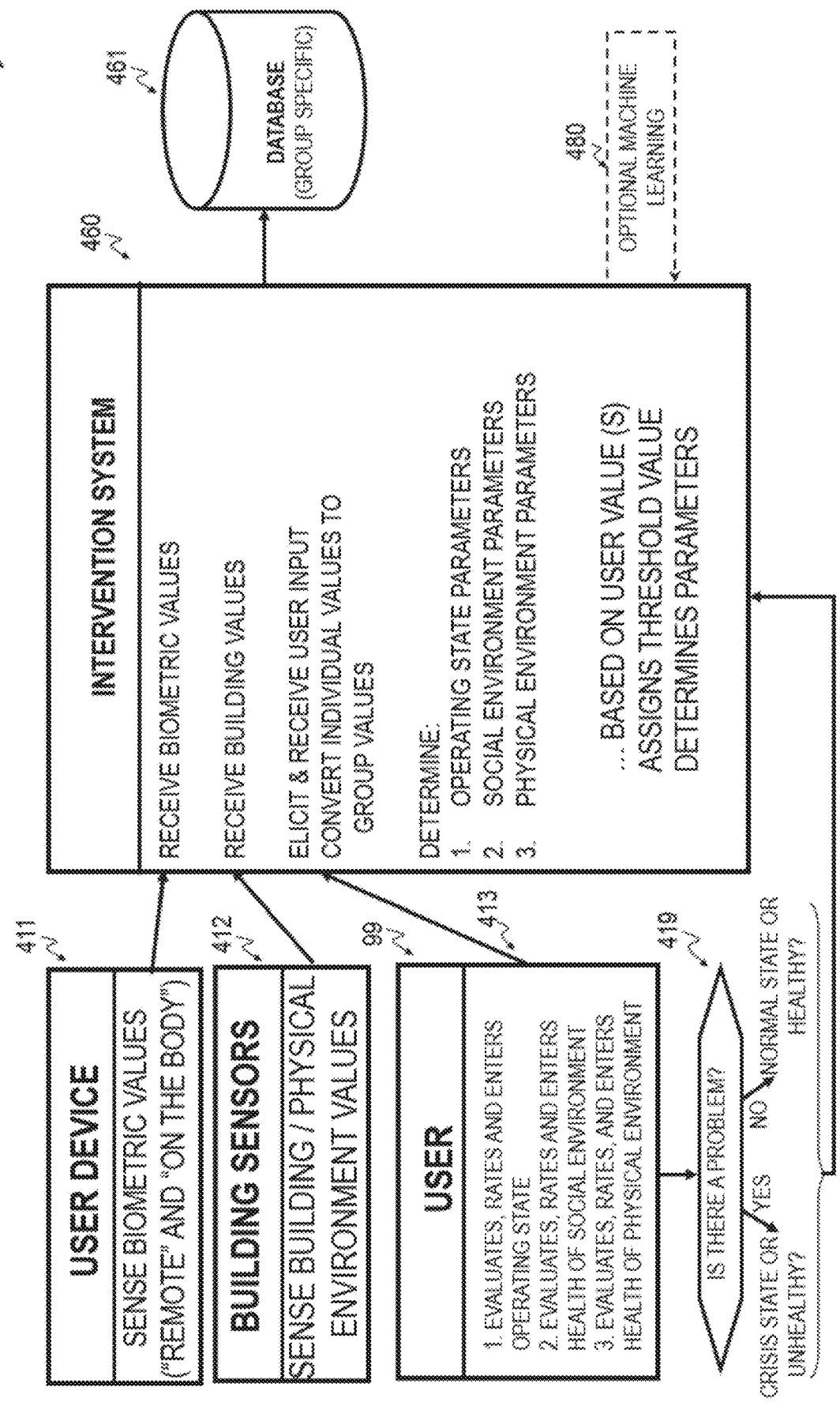

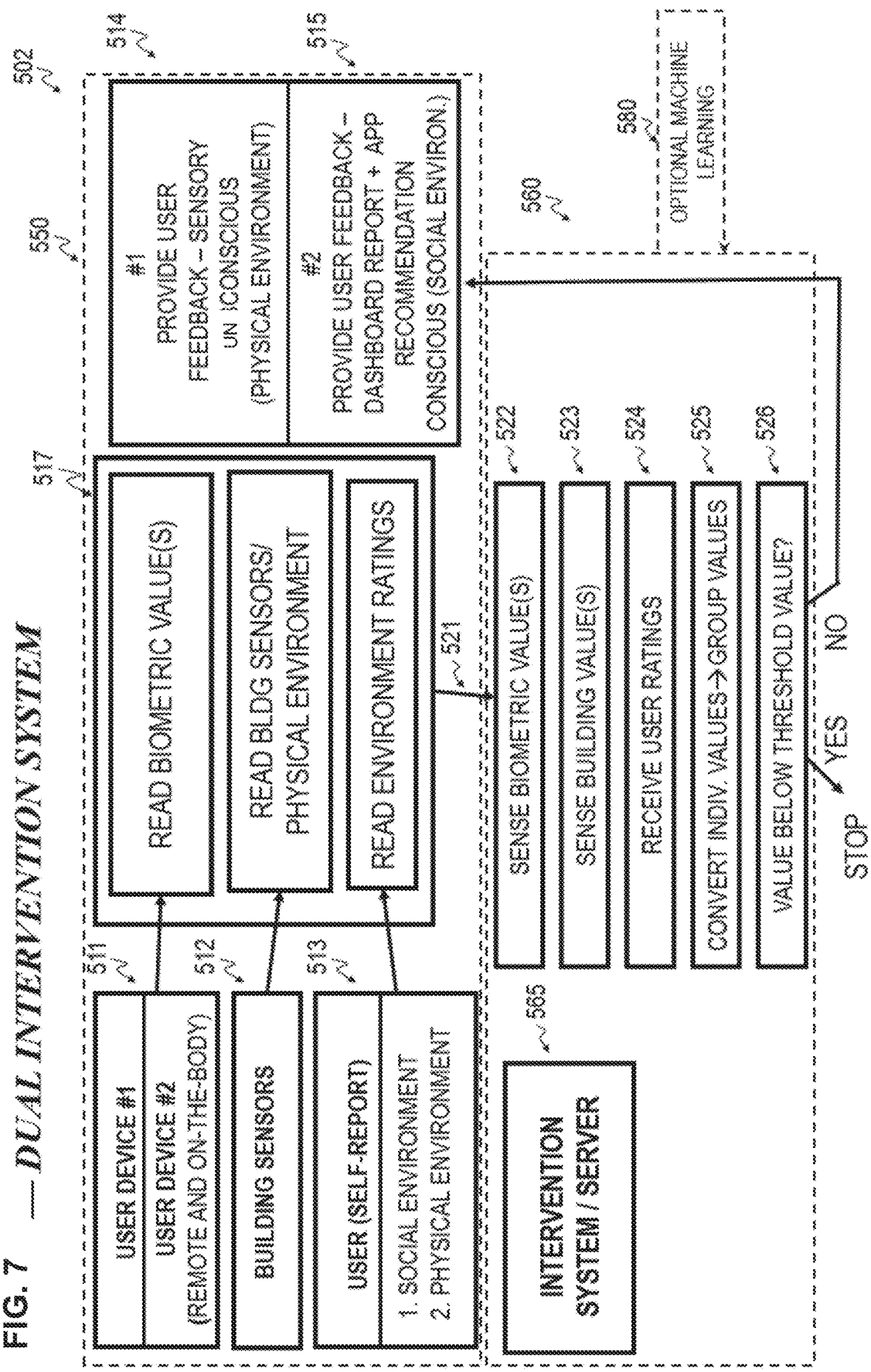
FIG. 7 — DUAL INTERVENTION SYSTEM

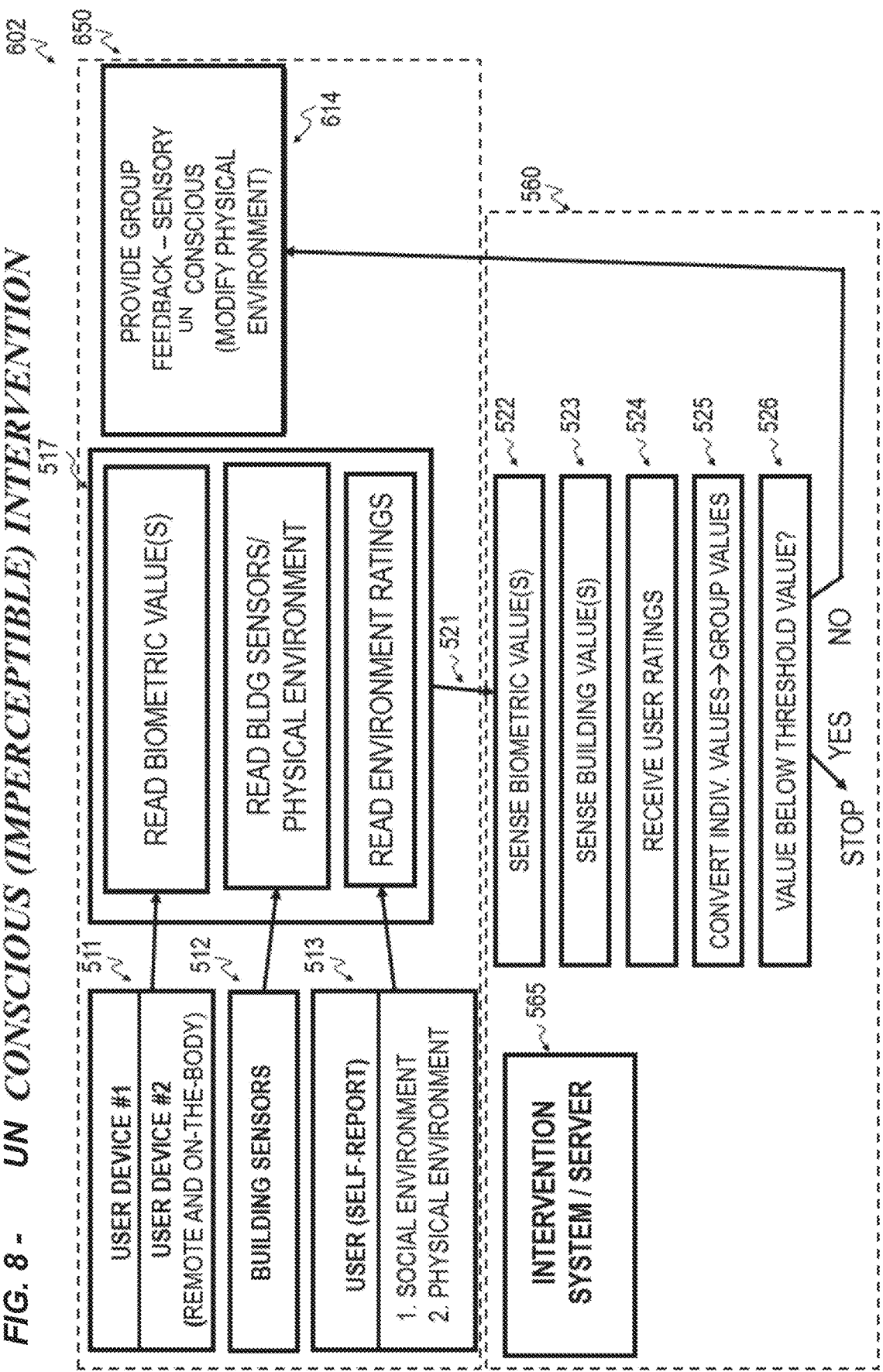
FIG. 8 - UN CONSCIOUS (IMPERCEPTIBLE) INTERVENTION

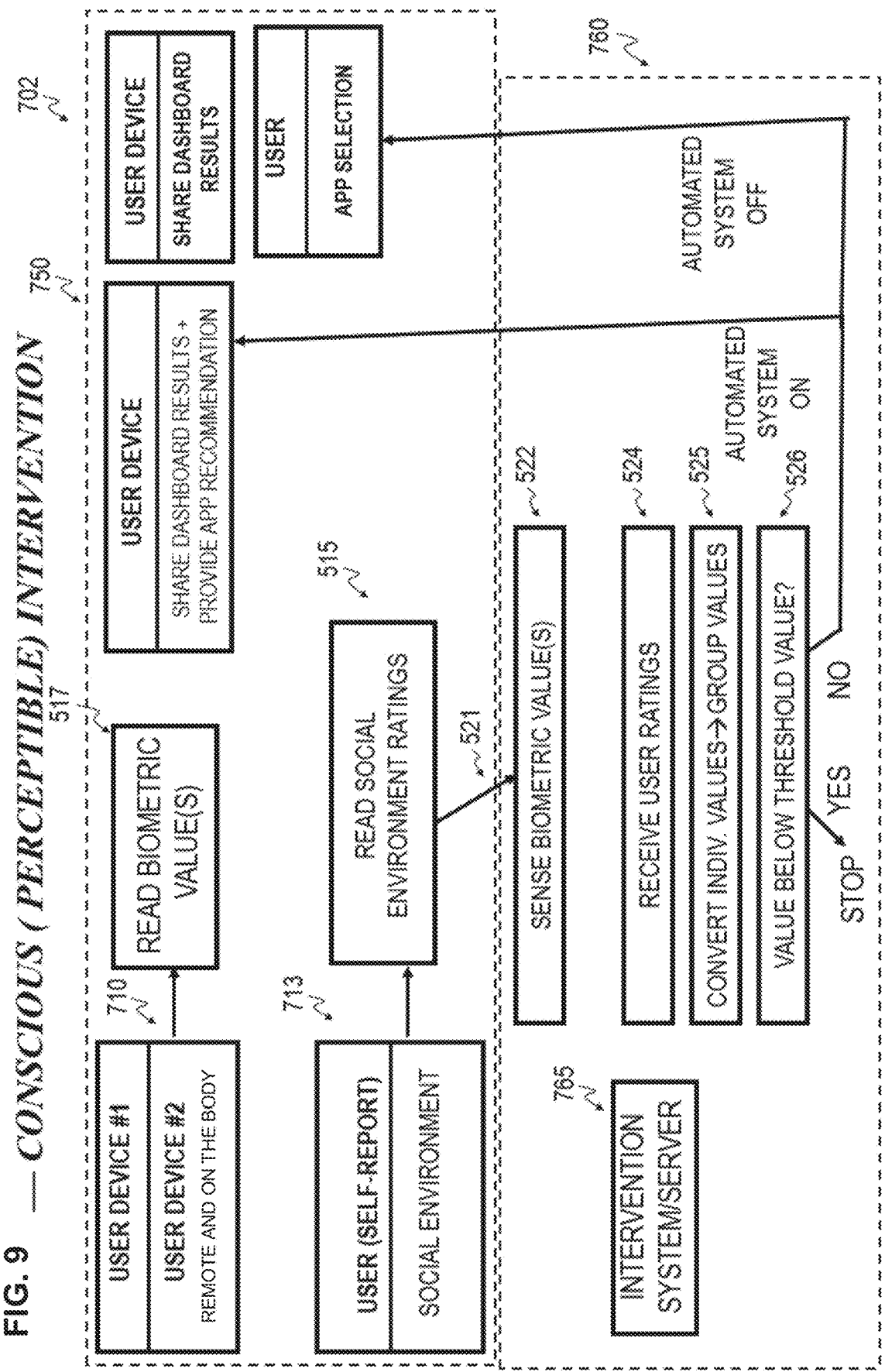
FIG. 9 — CONSCIOUS (PERCEPTIBLE) INTERVENTION

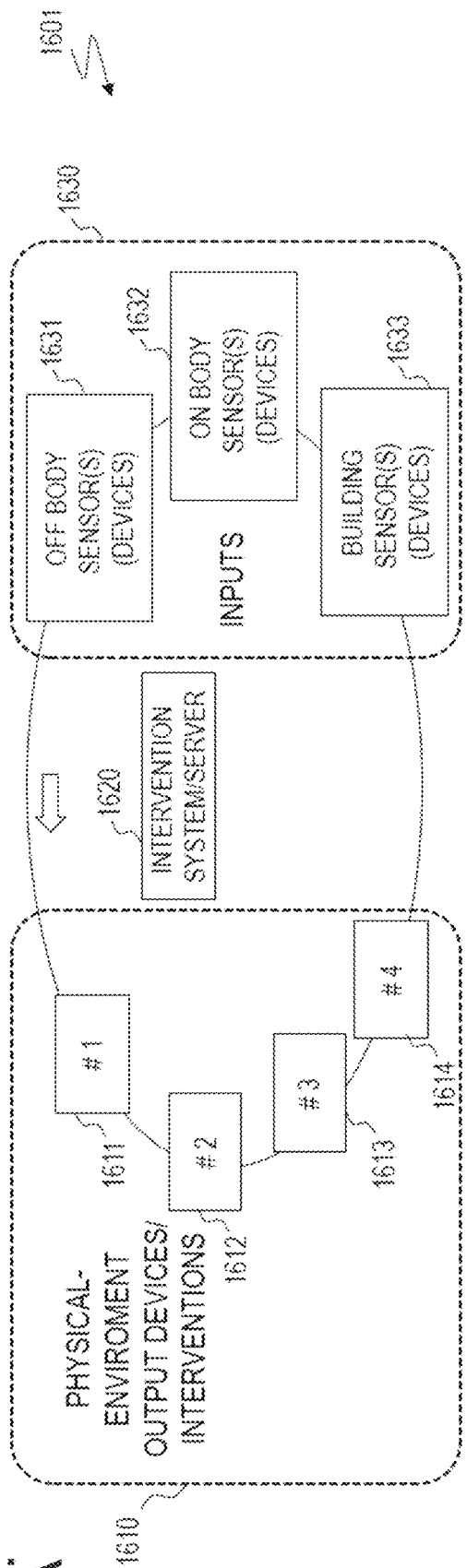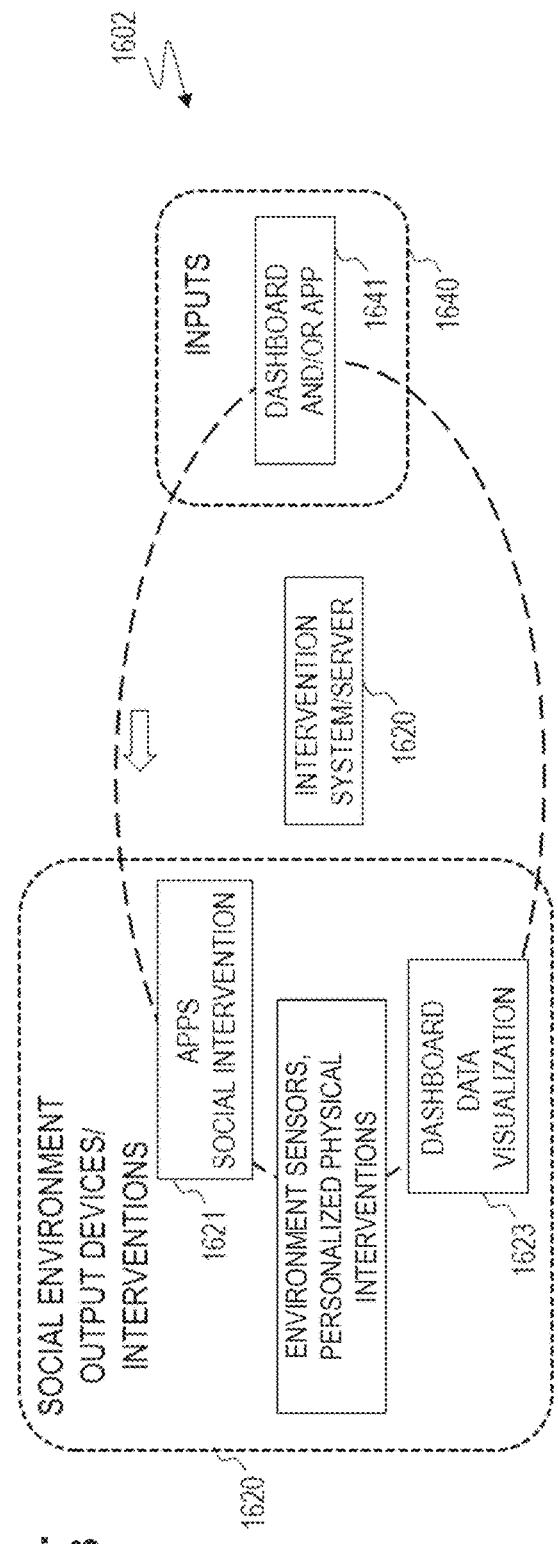

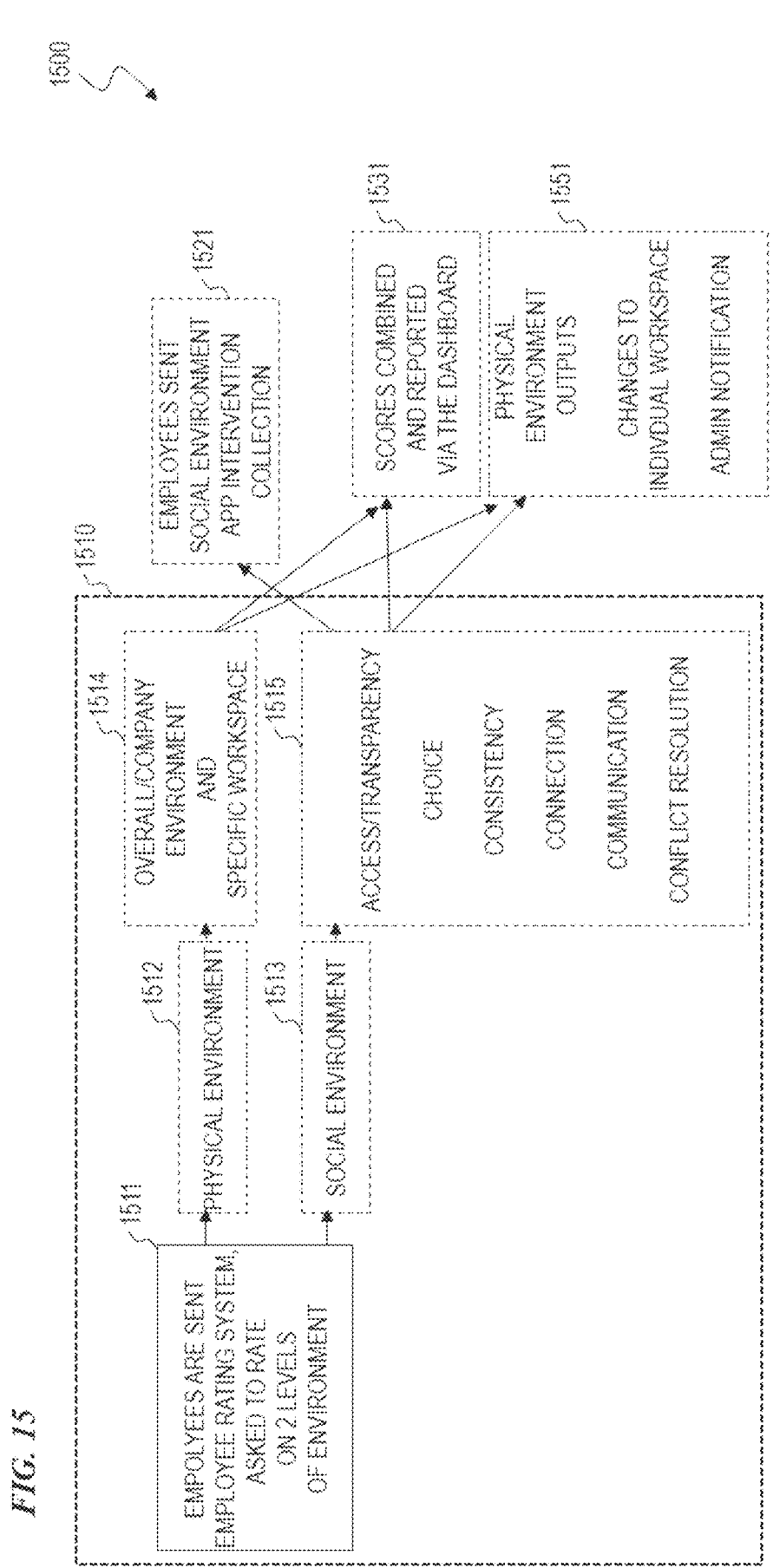

Measureable Group Stress Examples Table
1701

| Tool/Sensor | Form (On Body or Off Body) | Device Examples | Measured Information |
|---|---|---|---|
| Traditional Surveillance Tools (e.g., audio) | Off | Recorded power bank, flash drive | Group vocal speed, pace, volume (Increase = vocal distress = anxiety) |
| IPS and GPS Camera | Off | Portable, stationary | Walking speed, movement to specific locations (e.g., desire to escape) |
| Body Temperature | On | Wearable device | Increases in body temperature |
| Room Temperature | Off | Thermostat | Impact of aggregate group body temperature on room temperature |
| Group Heart Rate Monitoring | On | Wearable device | Increases in heart rate and strength of beat, use of machine learning algorithms for biometric fusion |

Input Sensor Area #1: Examples of Physical Environment Sensors  1703

| Sensor | What it measures |
|---|---|
| Decibel meter/microphone | Sound level |
| Photometer | Light intensity for lighting control |
| Thermometer | Room temperature |
| VOC sensor | Air quality (volatile organic compounds) |
| Carbon dioxide meter | Air quality |
| Olfactometer | Aroma/odor dilution |

FIG. 20B

Input Sensor Area #2: Examples of " OFF-THE-BODY Group Stress Sensors  1704

| Sensor | What it measures |
|---|---|
| Audio / recording devices | Group vocal speed, pace, volume |
| Desktop computer and/or smartPhone activity monitoring/recovery sticks | Aggregated increases in anxious-indicating content (e.g. escapism, distress texts) |
| Cameras | Increase in movement—fidgeting, nervousness. Increased lack of concentration—distraction. Aggregated measure. |
| Motion sensors (gyroscope accelerometer) | Change in velocity or speed |
| Room Temperature | Increasing body temps raises room temp. |
| IPS (Indoor Positioning System) | Location of people or things |

FIG. 20C

INPUT SENSOR AREA #3: EXAMPLES OF " ON-THE-BODY " GROUP-STRESS SENSORS

| Sensor | What it measures |
|---|---|
| Breath sensors (gas condenser, mass spectrometry – GC/MS) | Increases in metabolism |
| Body temperature (fever watch, smart bracelet, ear or forehead thermometers) | Increases in body temperature |
| Skin temperature (paste-on sensors, infrared cameras, tattoo thermometers) | Decreases in skin temperature |
| Heart rate monitor (FitBit, Apple watch, chest strap, arm/leg band) | Electric wave of depolarization of the heart muscle (chest strap); blood flow (arm/leg band) |
| Eye movement (smart glasses, cameras); ECG signals | Mental distraction – i.e., performance, productivity |
| Mass spectrometry (MS); chemoluminescent immunoassay analyzer | Cortisol concentration in hair (proxy to total HPA activity in the preceding months.) |
| Electrocardiogram + skin temp variation + electrodermal activity OR electrocardiogram + electromyogram + skin conductance + respiration | Human affective/emotional state |

INPUT SENSOR AREA #3: EXAMPLES OF "ON-THE-BODY GROUP-STRESS SENSORS

Building Output Devices
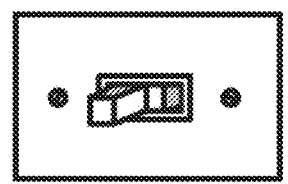
1801E
1801D
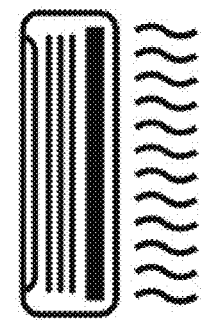
1801N
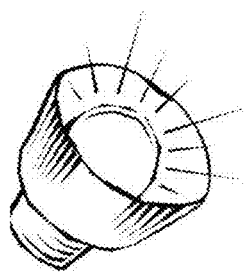
1801C
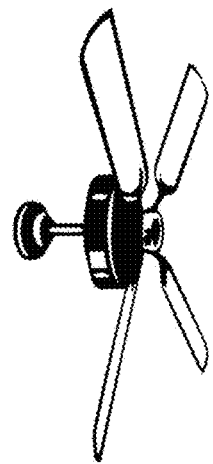
1801B
FIG. 21A Physical Environment Attributes Table
1802

POSITIVE ATTRIBUTES
- Window views
- Lighting & (day) light
- Signs of life (e.g., fish tank, plants)
- Ocean & park visuals - real or not
- Furniture layout for social interaction
- Natural textures & patterns
- Temperature
- Privacy
- Wall openings
- Ceiling surface and height
- Aroma inhalation
- Expectancy of calm
- Hominess
- Ability to move freely— i.e., physical wandering
- Green & blue spaces
- Individual control

NEGATIVE ATTRIBUTES
- Clutter
- Poor lighting
- Crowding
- Loud exterior noise
- Inaccessible architecture (low mobility)
- No individual control
- No green or blue spaces
- Low sound absorption

Communication Interfaces

*Could include...*

- Amazon Alexa
- Gogle Echo
- Apply Home
- IFTTT
- ZigBee
- 4-20 MA
- RS232
- RS485 Modbus
- Optical fiber
- ARCNET

- Ethernet Modbus TCP/IP
- I2C
- 1-Wire Communication
- Controller Area Network (CAN Bus)
- Bluetooth Low Energy
- Near Field Communication
- LTE
- IEEE 802.11n
- IEEE 802

OVERARCHING INTEROPERABILITY – via SNMP

Harmful Collective Behaviors:

1. Conflict tolerance.
2. Intention to change the situation—without action.
3. Change the interpretation of the situation—i.e., to make "sense" of it.
4. Storytelling to bring order and understanding.
5. Rationalization attempts.
6. Projection of the undesirable behaviors.
7. Resignation—i.e., psychological disengagement
8. Immobilization.
9. Minimization—especially when only one person is hurt.
10. Redefining the meaning of the situation.

10 Common Social Environment Ingredients that Lead to Behavior Transformation (i.e., from good to bad)

1. Identifying an acceptable justification for engaging in the undesirable action—"I'm helping them to become a better X".
2. Insistence on fulfilling a contractual obligation.
3. Giving participants meaningful, "esteemed" roles—e.g., teacher.
4. Presenting basic rules that seem to make sense prior to use, but then can be arbitrarily used to justify mindless compliance.
5. Altering the semantics of an act or action—e.g., from hurting someone to helping them to learn.
6. Creating opportunities for others to be responsible for the outcome—i.e., not the actor.
7. Starting the path toward the ultimate (unsavory) act with a small, insignificant first step only.
8. Increasing each level of aggression in gradual steps that do not seem like noticeable differences.
9. Gradually changing the nature of the influence authority—e.g., from just to unjust.
10. Making the "exit costs" high and the process of exiting difficult.

COMPUTER SYSTEM FOR GROUP CRISIS-STATE DETECTION AND INTERVENTION

CROSS-REFERENCE TO RELATED APPLICATIONS

This application is related to U.S. Provisional Patent Application No. 62/959,858, filed Jan. 10, 2020 by Kristen M. Heimerl titled "Computer system for crisis state detection and intervention" and U.S. Provisional Patent Application No. 63/054,230, filed on Jul. 20, 2020 by Kristen M. Heimerl titled "Computer system for crisis state detection and intervention", which are incorporated herein by reference in their entirety.

TECHNICAL FIELD

The disclosed technology relates principally to computerized systems for automatically sensing collective stress and providing active feedback to a group of individuals and more particularly to sensing individual and group behaviors and physiological states using building sensors that gather data about the physical environment, sensors remote to the persons that gather data about the persons, sensors on the persons that gather data about the persons, and input received overtly from individuals, and helping achieve the optimal collective operating state of a group of persons and, more specifically, to a system and method for detecting and intervening when collective physiological operating states become elevated or aroused, thereby reaching a group-crisis state. The system and methods are designed to gather parameters from a plurality of sensor types, analyze those parameters and output corrective measures for the group to diffuse collective crisis operating states, returning the group of individuals to their optimal or normal operating state. Three factors affect human stress levels that, when elevated, result in crisis operating states: 1) Personal Factors, 2) Physical Environment Factors, and 3) Social Environment Factors. The disclosed technology in this patent is designed to address Social Environment Factors and Physical Environment Factors that drive human stress levels. The disclosed technologies can be combined to holistically address the totality of factors that drive human stress.

BACKGROUND

A crisis state may be defined as "a time of intense difficulty or danger." A group crisis is an event or state that threatens the very stability of a group of persons convening for employment, education, community, social, recreational, or other communal or living purposes. A crisis implies a situation where time is short, and an effective decision must be taken immediately. The collective crisis state, if not intervened, perpetuates a sense of lack of control worsening the situation and thereby risking escalation and/or flawed human decision making. Crisis state intervention needs to be swift and effective with flexibility of interventions to meet individual and group differences and to meet further or prolonged shocks.

Three elements are generally attributed to a crisis state: (i) threat to the system, (ii) an element of surprise or unpreparedness, (iii) a short decision time to mitigate vs. exacerbate the situation which can lead to crisis escalation and the potential for irreversible damage via substandard decision making.

With 94% of Americans reporting experiencing stress at their workplace, 54% of workers reporting toxic cultures at work, and half of human resources professionals reporting that their organization had experienced a workplace-violence incident in the last year, harmful, crises-states and the outbursts that ensue from them are rising to unprecedented levels today—and not just in workplaces but in the private homes, schools, organizations, and various communities that make up society-at-large. There remains a need for providing groups with feedback to reduce collective stress levels that contribute to negative behaviors that cause injury to the group or individuals within the group. At the household level, the previously unmet need is for smart-home technology including hubs and controllers to enable crisis detection and intervention; and at the organizational or community level, the previously unmet need is for intelligent building technology married with wearable technology and sophisticated analysis and reporting tools to enable crisis detection and intervention.

SUMMARY

The disclosed system of wearable and non-wearable devices coupled with software and computing technology is designed to address the group-stress problem (also clinically referred to as "collective-stress problem") in the myriad social environment (also commonly referred to as "culture") and physical environments in which it manifests. Personal Factors that affect human stress levels can be addressed effectively with application of a direct intervention(s) aimed at the individual experiencing heightened stress. Addressing Social Environment Factors and Physical Environment Factors that affect human stress levels may not be as clear-cut. There is a complex interplay between individuals and the environments in which they live, work, and play. On the one hand, as humans, we are the product of our environment, but we are also a parent to it. Our behaviors and the behaviors we allow (and refuse to allow) in others shape our macro environment and the various microcultures in which we spend our lives. On the other hand, with the exception of one's private home, corporations, organizations, and communities create the buildings and shape the cultures in which we live through their spending, decision making, and values. The environments in which we operate, such as the workplace environment, have an existing physical structure and "tone" when we join them. As individuals, we're hard pressed to fundamentally change them. Likewise, corporations, organizations, and communities cannot exert total control over individuals to fundamentally change them. But while organizations cannot change people (unless the people want to be changed), they CAN change the social and physical environments that contain the people and shape their thinking and behaviors. The technology disclosed in related application entitled "COMPUTER SYSTEM FOR CRISIS-STATE DETECTION AND INTERVENTION," therefore can provide individuals with tools and technology to positively address the Personal Factors that affect human stress; and the disclosed technology herein provides organizations and communities with tools and technology to positively address Social Environment and Physical Environment Factors that drive human stress. Healthy environments lead to healthy people that want to help themselves and others lead healthy, productive lives.

Crisis states—individual and group—can be effectively detected and intervened via an amalgam of automated hardware, software, and sensors that perform measurement of physical, behavioral, and cognitive indicators. At an individual level, smart wearable technology enables crisis detection and intervention; at the household level, smart home technology including hubs and controllers enables crisis detection and intervention; and at the organizational and/or community level, intelligent building technology married with wearable and non-wearable personal technology enable crisis detection and intervention. And while the scale and complexity differ, the system and method for human crisis detection and intervention is the same and is outlined below.

In some embodiments, the disclosed technology provides a machine-learning computerized process that repeatedly, and substantially continuously, obtains data (symptoms) relevant to group stress (group-crisis state), determines an appropriate intervention, activates that intervention, obtains data relevant to the effectiveness of the intervention, and "learns" which symptoms are most relevant to group-stress determinations and which interventions are most effective in order to modify the system's future determinations and interventions based on the learning.

In some embodiments, the disclosed technology provides a PROCESS #1 that includes reading physiological parameters from a group of persons using on-the-body sensors (e.g., heart-rate, skin-resistance, temperature and the like), using off-the-body sensors (e.g., camera, interior position sensors (IPS), global positioning sensors (GPS), temperature sensors (e.g., FLIR cameras) and the like), and obtaining self-reported parameters from persons in the group relating to physical and social (cultural) environmental factors and their impact on stress levels via the system dashboard software application which serves both a data capture and reporting role. The dashboard can include information that can be organization-wide, including data, analytics, and reporting to assist an organization in determining how to improve and/or redefine employee engagement and/or satisfaction. Inputs from these sources are combined and analyzed (and, in some embodiments, individual data is anonymized) to determine if collective-stress levels are elevated outside the normal operating state range. Concurrently, the system reads data from building sensors (e.g., temperature, air quality, $CO_2$ level and the like, which communicate, for example, as an internet-of-things (IoT) system) to determine the current physical environment parameters from which to act upon (in circumstances of high collective stress.) IF group-stress levels are elevated, THEN the system outputs an (UNCONSCIOUS) PHYSICAL ENVIRONMENT intervention in the form of adjustments to building sensors (e.g., sensory-based modification to change the building environment and optionally customize individual workspaces,) and (CONSCIOUS) SOCIAL ENVIRONMENT interventions designed to both enhance cultural health and reduce or eradicate culture dysfunction or "toxicity" in the form of software applications that include the system dashboard (with reporting indicating an overall organizational health score aggregated from the measures taken from the input sources/sensors, scores indicating the PHYSICAL and SOCIAL ENVIRONMENT stress levels, and metrics pertaining to each of the input areas to identify where, specifically, stressors are outside of the "normal" range,) and a recommended social (cultural) environment group-stress-reducing "app" (software application) to individuals in the group that can coincide with one of six software application sub-collections aligned with proven group stress mitigating areas (which, non-coincidentally, are also culture improvers that have a direct, positive impact on productivity and innovation as well). This dual-intervention system outputs feedback systematically that is both CONSCIOUS and UNCONSCIOUS for optimal collective stress intervention and crisis-state mitigation and avoidance. As described herein, the term "unconscious" is utilized as shorthand to refer to complex, but familiar, psychological phenomenon whereby a good deal and perhaps most of mental life, as well as subtle changes in our surroundings, happen without our knowing much about it (UNCONSCIOUS) or, if of our consciousness, it flies below our 'radar screen.' In other words, some of the interventions can be perceptible to the individual or group—e.g., CONSCIOUS INTERVENTIONS but other interventions—UNCONSICOUS INTERVENTIONS—can be either imperceptible or largely imperceptible to the individual or group. In some embodiments, the system anonymizes and combines the on-the-body data, off-the-body data, and building data to determine a group stress level and an appropriate dual-part (unconscious and conscious) group-stress intervention to the physical environment and the social environment, and outputting that dual-part group-stress intervention. In some such embodiments, the system customizes some aspects of the GROUP intervention (e.g., social or physical environment influencer) for certain individuals in the group based on those individual's data and preferences as reported to the system. In some embodiments, the system anonymizes and combines the individual data to provide every user in the group with the same GROUP intervention. Anonymizing the data precludes the possibility of subsequent retaliation toward any one individual member of the group for unpopular or unwelcome feedback regarding the organizational PHYSICAL or SOCIAL environments ("culture").

In some embodiments, the disclosed technology provides a PROCESS #2. Process #2 can be comprised of two core processes—one of the processes can be automated; the other process includes some human intervention.) Process #2 includes reading physiological parameters from a group of persons using on-the-body sensors and using off-the-body sensors, anonymizing and combining these on-the-body and off-the-body data to determine the group stress level from physiological-type measures. IF group stress is elevated outside of the "normal" range, the system then reads data from building sensors to: (First) determine the current state of the physical environment by reading physical-environment parameters from traditional building IoT sensors, and (second) output an (UNCONSCIOUS) automatic adjustment to the PHYSICAL ENVIRONMENT to favorably influence the group stress level by creating a more positive space for individual and group activities to be carried out. Once the on-the-body and off-the-body sensors determine a crisis state, and after the physical environment has been modified via the building sensors, then the system can request self-reported feedback from persons in the group (via the dashboard application) to ascertain the health of the SOCIAL ENVIRONMENT (CULTURE) factors and their impact on collective stress levels. The employee data request can include requests for feedback on the health of the current state of social environment and the current state of the physical environment. These two inputs combined can provide a self-reported group stress measure (e.g., not biometric-based). If the intervention system/server determines that SELF-REPORTED group stress is elevated, and if individual data is not anonymized in step two, then it can implement three distinct interventions designed to positively impact the social environment—e.g., current cultural tone of the organization—thereby reducing the group stress level. First, the system can distribute a software app optimally selected for each individual from one of the sub-collections to the users based on their user feedback. Second, individual workspace office sensors can be adjusted to the personal needs of users as reported in the feedback and, finally, users can receive the data dashboard providing robust data and visualizations of the overall organizational health and key metrics underscoring it, including their personalized data and history, in some embodiments.

In some embodiments, after the SYSTEM automatically adjusts the PHYSICAL environment, then all individuals/users in the group are automatically provided a dashboard app that indicates that group stress is elevated, and in the dashboard app is a request-for-feedback form that elicits and receives from each user their evaluation of the SOCIAL environment. If the system determines that social-environment stress is elevated, then ALL USERS RECEIVE THE SAME SOCIAL- (CULTURAL-) INTERVENTION APP BASED ON INDIVIDUAL DATA THAT HAS BEEN AGGREGATED TO A GROUP LEVEL. In other words, in this embodiment, ALL users receive the SAME intervention app designed to improve the social environment from the stress-reducing app collection. In some embodiments, for example, All users are provided with the SAME app because the self-reported individual feedback, when aggregated, indicates one primary or common social environmental driver to group stress so, a common intervention is provided to all individuals in the group. In some embodiments, where individual data is captured and not anonymized, the system provides a tailored intervention to each individual—e.g., each user receives a social intervention app aligned with one of six collective stress mitigating areas that is MOST relevant to the collective stress drivers impacting that user: Access, Choice, Consistency, Connection, Communication, Conflict Resolution. In some embodiments, no individual data is captured as being identifiable as coming from a particular user nor stored in a user-identifiable format, and no personalized social environmental optimizing app recommendations are made, and every user gets the same intervention to reduce group stress with a GROUP INTERVENTION to preclude the possibility of retaliation toward any one individual by anonymizing individual data. In some embodiments, each user can choose not to accept the system-provided group intervention and can then privately choose an alternative from the six social-environment-optimizing app sub-collections, or to have their personal physical workspace environment adjusted to be, for example, warmer than the group space, if that setting helps them operate optimally.

In some embodiments, the foregoing process can be reversed. Specifically, after combining self-reported data to determine a set of social-environment parameters, and then combining these data to obtain self-reported group-stress-level parameters and IF group stress is present, then the system can deploy a trio of individualized social environment interventions: an appropriate app from the collections, a personalized sensory-based physical workspace adjustment, and the dashboard with data visualization, analysis, and reporting capabilities. Once the social environment has been addressed, then the system can address the physical environment by reading data from the building sensors (e.g., temperature, air quality, $CO_2$ level and the like, which communicate, for example, as an internet-of-things (IoT) system) to determine a set of physical-environment parameters. In addition, the system can take a reading of the on-the-body and off-the-body physiological attribute-sensing sensors. If group stress is determined to be elevated, then the building sensors can make adjustments to improve the health and comfort of the organization's physical environment.

One or more preferred embodiment can include a system for group-crisis state detection and intervention, the system having a plurality of mobile devices (e.g., user devices, input devices) that can collectively detect first biometric conditions specific to individual users of a plurality of users, each of the first biometric conditions identifying a health state of each of the users in the plurality of users and transmit, to a computing system, the first biometric conditions. The system can also include a plurality of sensors positioned in a physical environment where the plurality of users are located, the plurality of sensors being separate from the plurality of mobile devices, and can detect group conditions of the plurality of users in the physical environment and transmit, to the computing system, the group conditions. The system can also include a computing system having one or more processors, the computing system can receive, from the plurality of mobile devices and the plurality of sensors, the first biometric and the group conditions can associate the first biometric conditions and the group conditions as being part of conditions relevant to a group. The association between the first biometric conditions and the group conditions can be based on associations between (i) the plurality of users and the plurality of devices, (ii) users of the plurality of users and the plurality of users and (iii) the plurality of users and the physical environment. The computing system can also identify, using one or more models, a group state of the plurality of users in the group based on the conditions relevant to the group, wherein the one or more models have threshold indicators of different group states of the plurality of users in the group, wherein the different group states include a group crisis state and a group normal state. The computing system can also generate, based on identifying that the group is currently in the group crisis state, intervention instructions that are configured to be automatically executed by one or more acting devices, the intervention instructions being configured to produce actions on the one or more acting devices to lower the plurality of users collectively from the group crisis state to the group normal state, and transmit, to the one or more acting devices, the intervention instructions. The one or more acting devices can receive the intervention instructions from the computing system, and, in response to receiving the intervention instructions and without permission or input from the plurality of users, to automatically perform the intervention instructions on the acting devices.

The preferred embodiments can include one or more of the following features. For example, intervention instructions include one or more of (i) adjusting one or more settings in the physical environment, (ii) providing one or more interactive applications to the plurality of users at the plurality of mobile devices, and (iii) activating communication between the plurality of users at the plurality of mobile devices and an interactive coach. The intervention instructions can include two or more of (i) adjusting one or more settings in the physical environment, (ii) providing one or more interactive applications to the plurality of users at the plurality of mobile devices, and (iii) activating communication between the plurality of users at the plurality of mobile devices and an interactive coach. The intervention instructions can include (i) adjusting one or more settings in the physical environment, (ii) providing one or more interactive applications to the plurality of users at the plurality of mobile devices, and (iii) activating communication between the plurality of users at the plurality of mobile devices and an interactive coach. The intervention instructions can cause at least one of unconscious intervention or conscious intervention on the plurality of users.

The computing system can also determine the group normal state based on one or more historic first biometric conditions, historic group conditions, the detected first biometric conditions, and the detected group conditions being below a threshold value. The historic and detected first biometric conditions can include at least one of current physiological conditions, a heartrate, a blood flow, sweat, bodily movement, volume of voice, or speaking pace. The first biometric conditions can also be a combination of one or more of breathing rate, body temperature, skin temperature, cognitive-distraction, cortisol-concentration, electrocardiogram, electrodermal activity, electromyogram, skin conductance, and/or respiration. The historic and detected group conditions can include at least one of bodily movement, volume of voice, speaking pace, temperature of the physical environment, noise level in the physical environment, or odor. The historic and detected group conditions can also include location of members of the group in the physical environment, quantity of members in the group, or location of objects in the physical environment relative to locations of the members of the group (e.g., too many people in one area can cause crowding, which can cause stress). The intervention instructions can include adjusting one or more settings in the physical environment including dispersing an aroma in the physical environment, adjusting a temperature of the physical environment, adjusting a lighting of the physical environment, or playing calming audio in the physical environment. Moreover, in some implementations, the intervention instructions can include causing movement of physical objects or elements of the physical environment to reduce group stress. For example, the physical environment can have automated walls, windows, ceilings, doors, etc. that can be automatically moved within the physical environment to create space where there is crowding, add natural light where this is none, or inject fresh air where it is still (e.g., in smart homes).

The acting devices can be configured to, in response to receiving the intervention instructions, provide a visual alert or an audible alert to the plurality of mobile devices that prompts the plurality of users to perform an action on the plurality of mobile devices. The action can be (i) selection of an interactive application presented at each of the plurality of mobile devices or (ii) performing actions in an interactive application that was selected by the computing system based on the group crisis state exceeding a threshold level. The computing system can be configured to select the interactive application based on determining, from the one or more models, that the group crisis state is above a threshold indicator of a group crisis state. The interactive application can include instructions prompting the plurality of users to perform actions at the plurality of mobile devices that are intended to collectively lower the plurality of users in the group from the group crisis state to the group normal state, the actions including (i) engaging in an online conflict resolution between the plurality of users and an artificial intelligence (AI) mediator, (ii) playing a game with one or more of the plurality of users, (iii) performing an act of service for one or more of the plurality of users, (iv) providing positive feedback to one or more of the plurality of users, or (v) providing negative feedback to one or more of the plurality of users.

The one or more acting devices can be configured to (i) execute the intervention instructions while the detected first biometric conditions and the group conditions exceed a threshold value indicative that the plurality of users in the group are operating in the group crisis state and (ii) terminate the intervention instructions when the detected first biometric conditions and the group conditions are lower than the threshold value. The computing system can also receive, from the plurality of mobile devices, user input from one or more of the plurality of users identifying stressors in the physical environment, and modify, based on the user input, the intervention instructions to target the identified stressors.

The computing system can also train the one or more models having threshold indicators of different group states of the of the plurality of users in the group based on the detected first biometric conditions and group conditions, executed intervention instructions, an amount of time taken to lower the group from the group crisis state to the group normal state, and an efficacy score of the executed intervention instructions. In some implementations, the efficacy score can be based on key leading measures and/or lagging measures. Leading measures can include time to reduce the group from the crisis state, increased positive behaviors, and/or decreased negative behaviors induced by the applications (e.g., more sharing, more communicating, more acts of service, more effective conflict management). These can be leading measures because more positive behaviors and fewer negative behaviors done by each individual—and collectively—are early, impartial indicators of achieving the desired end goal which is a healthier environment and, thus, healthier people. Lagging measures can include individual user feedback. For example, user feedback can include reviews of what group members think or perceive about the physical and social environments, what changes can drive the people to be more productive and innovative. User feedback and/or perceptions are another, albeit subjective, measure that attests to the health of the physical and/or social environment.

The intervention instructions can include activating communication between the plurality of users at the plurality of mobile devices and an interactive coach, the interactive coach being an artificial intelligence (AI) coach that can be trained, by the computing system and using machine learning, based on historic crisis interventions for the plurality of users in the group. The acting devices can be configured to, in response to receiving the intervention instructions from the computing system, uniformly execute the intervention instructions at the plurality of mobile devices for the plurality of users in the group. The acting devices can also, in response to receiving the intervention instructions from the computing system, modify the intervention instructions at each of the plurality of mobile devices for each of the plurality of users in the group based on the first biometric conditions for each of the plurality of users. The interactive coach can be a human coach. The computing system can also predict, using machine learning and the one or more models having threshold indicators of different group states of the plurality of users in the group, when the group will enter the group crisis state and generate second intervention instructions that are configured to be automatically executed by the acting devices, the second intervention instructions being configured to produce an action on the acting devices to maintain the plurality of users in the group in the group normal state. The acting devices can include the plurality of mobile devices, the one or more sensors in the physical environment, and a building computing system, wherein the building computing system can adjust one or more conditions of the physical environment. The computing system can also determine an efficacy score for executed intervention instructions in lowering the plurality of users in the group from the group crisis state to the group normal state. The efficacy score can be based on an amount of time taken to lower plurality of users in the group from the group crisis state to the group normal state being less than a threshold value.

One or more advantages can be recognized from the disclosure herein. Human crises states—the human stress response—is an insidious invader to human health that sneaks in and takes over hundreds of different mind and body pathways if we aren't vigilant. Bringing a group (or individual) down from an elevated state of physiological distress can require a full-on attack that involves constant control over human HEADS (COGNITION) and human BODIES (SENSES—PHYSIOLOGY). The disclosed technology can ambush group crisis states via a multiplicity of UNCONSCIOUS (e.g., sensory-based physical changes to the built environment) and CONSCIOUS (e.g., interactive software applications) interventions delivered IMMEDIATELY through myriad user and building devices at an ongoing basis to improve environmental factors, stop rising physiological stress levels, and return the group to their normal operating state. Multiple devices can be used in the system because, depending on where the devices are placed on the human body, or in the built environment, and/or the role the devices play, each device can allow for sensing different physiological attributes that drive the human stress response, different sensory attributes that contribute to a positive or negative physical environment, and different cultural attributes that contribute to a positive or negative social environment or "organizational culture." In addition, these devices allow for many different types of interventions—and combinations of interventions—both CONSCIOUS and UNCONSCIOUS. The DUAL INTERVENTION system can provide for enhanced system efficacy. UNCONSCIOUS interventions can be largely imperceptible and include SENSORY-TYPE interventions—sight, sound, taste, touch, smell—made via the building sensors to tangibly modify the built or physical environment. The sensing organs associated with each sense send information to the brain to help us understand and perceive the world around us. The UNCONSCIOIUS INTERVENTIONS—e.g., favorable, physical modification to the built environment—can directly impact human physiology—grabbing hold of a runaway human stress response (individual AND group)—by physically diffusing a threat to the system perceived by the sense organs of the human body. For example, the sensory intervention can be the closing of a movable wall partition to isolate the loud noise level of one group from distracting another working quietly nearby. Or the sensory intervention can be the opening of a skylight/window to allow natural air and sunlight into a workspace; or a screen or film depicting beautiful or awe-inspiring nature images may be released to cover a blank wall in a common area where motion sensors have detected hyper-agitation. Or there may be the emission of a calming aroma through the ventilation system such as mountain air, cookies baking in the oven, or lavender. These UNCONSCIOUS INTERVENTIONS can be advantageous for a few reasons. First, they elicit a positive response from the user and the group—both types of human stress are impacted by the change. Second, the intervention can be implemented without distracting the user or the group (e.g., preventing them from carrying on with a current task) or inducing a sense of overwhelm by forcing the user or group to cognitively focus on sub-optimal surroundings contributing to elevated stress levels.

CONSCIOUS INTERVENTIONS have a different job, providing another layer of advantage. In the disclosed technology, the conscious interventions (apps) can be distributed to all members of the group at once. As such, each individual who receives the app benefits from the intervention but so does the entire group by engaging in a social environment-enhancing activity collectively and concurrently. The apps are designed to grab hold of the group member's brain/cognition while group stress is elevated by offering an IMMEDIATE DISTRACTING ACTIVITY to the individuals in the group. Human lives are controlled by three things: Thoughts, Emotions, and Actions. Humans cannot change their emotions directly. Changing our thoughts can be difficult. We can change our actions to consciously disrupt a runaway crisis state. We can influence group crisis states by applying positive mass interventions that individual members of the group engage in concurrently or experience together but at different times. CONSCIOUS INTERVENTION activities described herein can be software applications that consume and engage the users in the group by offering another, different form of IMMEDIATE intervention. The app collection can be comprised of six app sub-collections each aligned with a different proven social environment enhancer that diffuse crisis states (e.g., Access, Choice, Consistency, Connection, Communication, Conflict Resolution). Just like there are multiple devices and device combinations enabled by the system to sense rising stress levels and intervene, there can also be many different immediate intervention types made possible by the five broad types of sense-influencing UNCONSCIOUS interventions and six broad families of cognitive-influencing CONSCIOUS interventions. All of the CONSCIOUS interventions can activate the mesolimbic pathway (e.g., "the pleasure center") of the brain. Positive emotional states arise from using our software by influencing a core neurophysiological system (related to valence—a pleasure-displeasure continuum) that shifts user's affective state from displeasure to pleasure. The interventions delivered and described herein can be IMMEDIATE by design. Individuals in a crisis state need IMMEDIATE interventions to help them manage the critical MOMENT of heightened physiological arousal. Because groups are comprised of individuals, our interventions can be centered on swift, effective, IMMEDIATE de-escalation techniques, however, because group stress is a complex function of the individuals in the group, and we know that not all users will engage or de-escalate at the same time despite the immediacy and mass release of the intervention, we know that there can be a lag in response time between when the intervention is applied and the time that a favorable reduction in group stress will be achieved. So, while IMMEDIACY is equally as important to the group crisis state intervention system as to individual crisis state intervention, the impact of a group intervention can be less immediate than the impact of an individual intervention simply because of the inherent complexity of group stress.

Another advantage of the system is that it can be flexible and scalable. Although the technical design and intention is to bombard a crisis state from every angle in real-time to bring about swift reduction and return to the group's normal—non crisis—operating state, not every group may require the same level of crisis support. For example, a family or a small, tightly-knit privately held accounting practice with 8 employees and one physical location would need a far less robust system than a Fortune 100 company with unstable leadership, 100,000 global employees, and thousands of workers concentrated in any one location.

Other advantages are realized from the disclosed technology, systems, and methods. For example, in workplace environments, conventional employee-satisfaction surveys are taken once yearly and may take weeks or months to achieve a company's response to a detrimental social or physical environment. In contrast, the disclosed technology provides real-time and continuing anonymized measurements and determines and outputs real-time interventions for addressing problematic social environment (culture) and physical environment factors that lead to elevated stress levels and contribute to "toxic" organizational cultures that are breeding grounds for dysfunctional individual and collective behaviors including intentionally behaving or causing others to act in ways that demean, dehumanize, harm, destroy or kill innocent people. Common collective behaviors that manifest in environments overwhelmed by group stress also include the failure to help those in distress, sometimes called "bystander failures." The disclosed technology provides for real-time, continuous assessment of conditions in a social and/or physical environment to predict and prevent one or more individuals or groups of individuals from entering crisis states that lead to behaviors that may cause irreparable damage to self or others. Importantly, the disclosed technology further provides for intervention generation and application of interventions to the physical environment which, when coupled with interventions made to improve the social environment, address the totality of drivers to human stress, excluding personal factors.

The disclosed technology provides a computer-implemented method and system for automatically detecting and automatically intervening in group-crisis states resulting from sub-optimal physical and social environments in which people live, work, and play. The system utilizes one or more user devices and/or input sensors to monitor, measure, and detect the collective operating state of a group of persons via obtaining measurements/values of physical (e.g., heartrate, blood flow, breathing, bodily secretions, muscle tension, body metabolism) and/or behavioral (e.g., movement, voice) indicators, or any combination thereof. These biometric values are taken both by remote-from-the-person ("off-the-body" sensors, e.g., traditional surveillance tools, building sensors, and the like) and on-the-person (sometimes called "on-the-body," "on-the-skin" or "under-the-skin," e.g., wearable devices, smart cell phones, and the like, although these sensors may include devices implanted inside the person, in some embodiments) and are used to determine the group operating state at any given moment within particular social and physical environments. Where individual measures are sensed, sophisticated algorithms are used to transform individual measures to a group measure—e.g., biometric fusion. To ascertain the "state" of the social and physical environments (which will be modified by the system IF group operating states are outside of the normal rang), two additional sets of measures are obtained: 1) physical environmental measures obtained through building sensors (standard and enhanced IoT/building automation systems that can be located within and/or outside of buildings in communities—for example, a camera on street light post) and 2) self-reported user ratings required to assess group perceptions and attitudes of the social environment (culture) and physical environment at any given point in time. In some embodiments, the self-reported measures contribute to the group stress determination. In some embodiments, only the physiological measures taken from the on-the-body and the off-the-body sensors contribute to the group stress determination. In all, the four broad measurement inputs—"remote-from-the-person" ("off-body") group-stress measures, "on-the-person" ("on-body") group stress measures, traditional IoT building automation sensors, and self-reported user ratings are communicated from the respective user device(s) and/or building sensors via the communication interface to the intervention system/server over a network (wired or wireless) in accordance with the different core processes outlined previously. The intervention system/server receives the values (and conducts biometric fusion, if necessary) and sends them to the information determiner that assesses if the group has achieved a crisis state by comparing the values it receives against a predetermined baseline or threshold value established using historical data established during the training period for the present computerized system and continually updated and optimized via machine learning. If the intervention determiner detects a crisis state (i.e., above the threshold), it will apply DUAL INTERVENTION methods—conscious (perceptible) and unconscious (imperceptible)—to diffuse the crisis state and return the group operating state to normal. If the intervention determiner does not detect a crisis state (i.e., below the threshold), no intervention occurs and, in some embodiments, a positive intervention is optionally applied. Once the intervention determiner makes a crisis/no crisis determination, the data/values are transmitted to the database for storage and subsequent processing and retrieval; and it sends data back to the user device(s) and building sensors via the communication interface. In some embodiments, the intervention determiner utilizes artificial intelligence and/or machine learning and/or other computational methods and algorithms (e.g., Gaussian Mixture Models, Artificial Neural Networks, Fuzzy Expert Systems, Support Vector Machines, and the like) to arrive at a multimodal biometric system and group measure, and to compare input data and parameters and composite values to historical values stored in the database to make the system's automatic determination of the group operating state. Based on the assessment, the system determiner may or may not implement an intervention. In some embodiments, artificial intelligence and/or machine learning are used in the overall assessment, interventions, and continuous feedback by which the system initially "learns" to determine group-crisis states and appropriate group interventions, and then later continuously improves itself over time.

In some embodiments of the disclosed technology, a crisis threshold is obtained for the group based on one or two individuals in the group, not the entire group, while in other embodiments, a crisis threshold is obtained for the group based on a sensory measurement of the group—taking a "group temperature" of the whole via the whole (e.g., off-the-body measures such as group vocal speed, pace, and volume; increases in group movement; increasing room temperature). In other embodiments, a crisis threshold for the group is obtained by taking measures of individuals and translating individual measures to the whole via biometric fusion or aggregation. For example, heart rate speed and variability, mental distraction, or decrease in skin temperature obtain via on-the-body and off-the-body sensors. In some embodiments, microphones and cameras assess the group operating state, for example. In other embodiments, light detection and ranging lasers do so by measuring human traffic speed. And in still other embodiments, mass spectrometry may be used to detect increases in metabolism or changes in cortisol concentration. When all or most of the measures are materially elevated across the board (across all people) due to a threat (such as a culture shock due to a corporate merger or acquisition, or the risk of unemployment driving a culture of extreme fear and personal survival at all costs) or a toxic social environment that is escalating further due to the powerful interplay between stress and toxicity, and where a group-stress response is triggered, the disclosed technology is used to detect the elevated group operating state and to provide interventions to positively influence the physical environment, the social environment (culture), or both environments in an effort to de-escalate high group operating crisis states that, if left alone for a sustained period of time, can lead to harmful and/or irreparable damage as a result of irrational behaviors or difficulty making well-reasoned choices under extreme environmental stressors. Stress exposure influences basic neural circuits which can influence reward processing and learning, bias decisions towards habit, and modulate our propensity to engage in risk-taking—all of which can yield undesired outcomes.

In some embodiments, machine-learning (ML) algorithms and/or deep learning are applied for biometric fusion to arrive at a multimodal biometric system and group measure, and to improve the system's accuracy in detecting crisis states and determining which interventions are optimal for de-escalation under specific (physical and social) environment parameters and under specific (human) physiological and behavioral parameters. Deep learning is a subset of machine learning in artificial intelligence (AI) that has networks capable of learning unsupervised from data that is unstructured, also known as deep neural learning or deep neural networking. In some embodiments of all the intervention servers described herein, thousands or hundreds of thousands of parameter combinations are presented to the machine-learning algorithms, wherein each one of the combinations is indicated as "group-crisis state" or "group-normal-operating state" and the algorithm automatically performs its own analysis on order to learn which combinations of parameters would be a group-crisis indicator. Further, based on self-report data from users (both before a system intervention is applies and afterwards) as to which situations were crisis state and which interventions were successful, the algorithm improves over time as to the algorithm's accuracy in detecting crisis states, and in which interventions worked to improve the group operating state and which are contra-indicated. In some embodiments, ML algorithms include, e.g., Gaussian Mixture Models (GMMs), Artificial Neural Networks (ANNs), Fuzzy Expert Systems (FESs), and Support Vector Machines (SVMs.)

Accordingly, the disclosed technology utilizes a dual intervention approach to apply both imperceptible (or barely perceptible) sensory-based interventions (called "unconscious" feedback herein) for example, modifying the physical environment by increasing (day) light, reducing the room temperature or emitting a favorable noise or aroma as well as modifying the social environment (culture) via perceptible interventions (called "conscious" feedback herein) such as recommending a group-stress-reducing "app" (software application) to mitigate the stress response, restore the normal state range and corresponding healthy productivity and engagement levels associated with normal, non-elevated, group-operating states. One or more additional advantages of the disclosed technology can be recognized as described throughout this disclosure.

BRIEF DESCRIPTION OF THE DRAWINGS

FIG. 1 is a table that illustrates personal, physical environment and social environment factors affecting individual and group stress (also often clinically referred to as collective stress), according to some embodiments of the disclosed technology.

FIG. 4 is a block diagram of a structure involving the detection and intervention of a human crisis state, when this technology is utilized at the group level, according to some embodiments of the disclosed technology.

FIG. 5 is a diagram of a process involving the communications process and transmission of data between the user device(s), the building sensor(s), the users, and the intervention system/server, according to some embodiments of the disclosed technology.

FIGS. 6A-B are diagrams of a process for determining the group baseline operating state, according to some embodiments of the disclosed technology.

FIG. 7 is a block diagram of a dual-intervention system, according to some embodiments of the disclosed technology.

FIG. 8 is a block diagram of an unconscious group-intervention system and method, according to some embodiments of the disclosed technology.

FIG. 9 is a block diagram of a conscious group-intervention system and method, according to some embodiments of the disclosed technology.

FIG. 10A is a block diagram of an automated unconscious physical-environment intervention system for group-stress intervention, according to some embodiments of the disclosed technology.

FIG. 10B is a block diagram of a controlled conscious social environment (culture) intervention system for group-stress intervention, according to some embodiments of the disclosed technology.

FIG. 15 is a block diagram of system that gathers self-reported data from individual users for group interventions, according to some embodiments of the disclosed technology.

FIG. 18 is a table that indicates examples of how group stress is measurable, according to some embodiments of the disclosed technology.

FIG. 20A is a table that lists types of physical environment sensors used to obtain parameters of the physical environment affecting the collective stress of a group of persons, according to some embodiments of the disclosed technology.

FIG. 20B is a table that lists types of remote (off-the-body) sensors used to obtain collective-stress parameters of the group of persons, according to some embodiments of the disclosed technology.

FIG. 20C is a table that lists types of on-the-body (on-the-skin) sensors used to obtain individual physiological parameters of the persons in a group affecting that group, according to some embodiments of the disclosed technology.

FIG. 21A is a conceptual diagram that illustrates types of physical environment output actuators used to modify parameters of the physical environment affecting a group of persons, according to some embodiments of the disclosed technology.

FIG. 21B is a table that lists types of physical environment factors that affect stress in a group, according to some embodiments of the disclosed technology.

FIG. 23 is a table that lists communications interfaces useable by various systems of the disclosed technology.

FIG. 24 is a description that illustrates types of harmful collective behaviors that arise when group stress levels are elevated.

FIG. 25 is a description that illustrates the social environment (cultural) ingredients that transform behaviors from positive to negative when group stress is elevated.

DESCRIPTION OF PREFERRED EMBODIMENTS

Figure 2A:
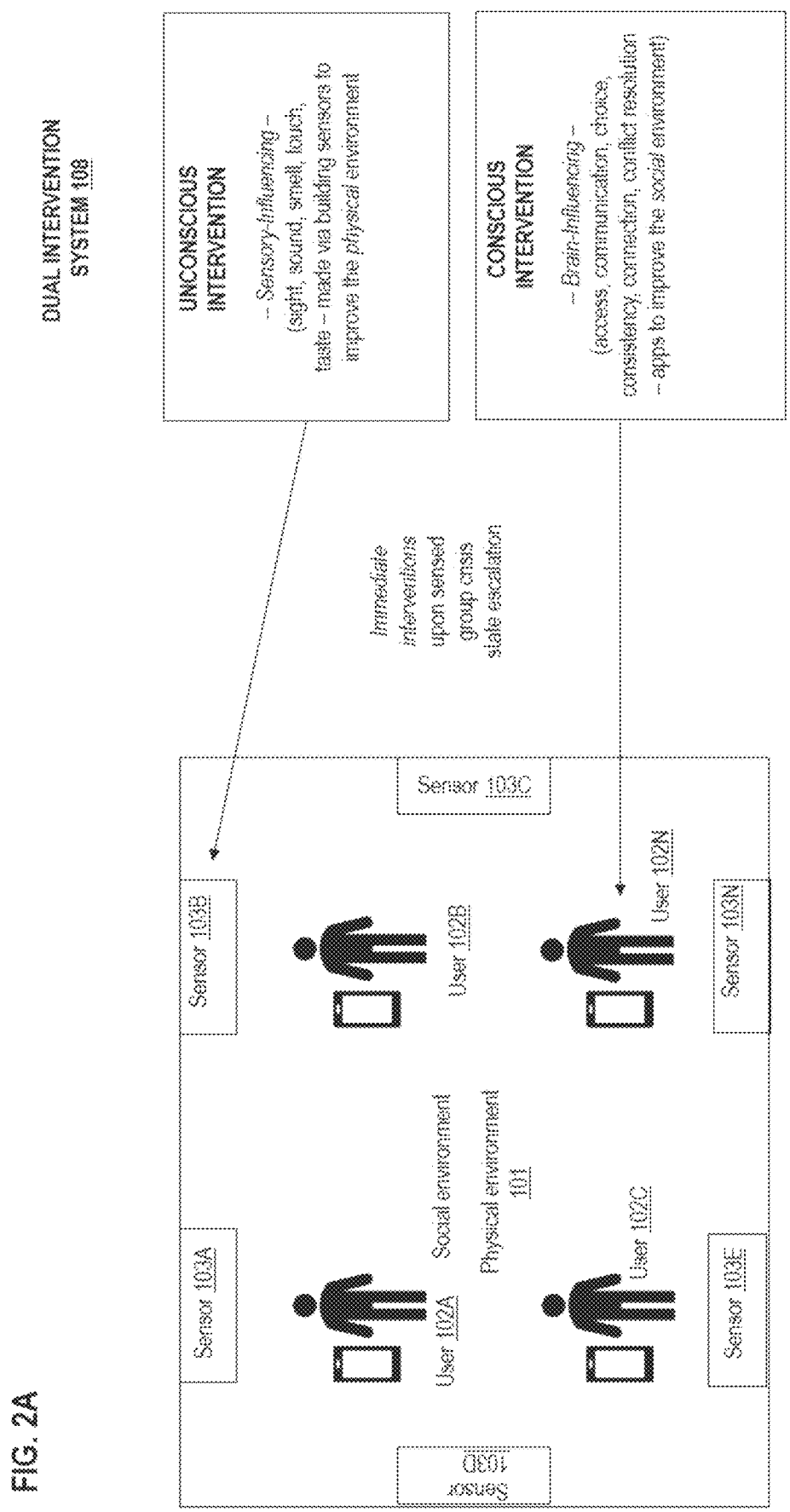
FIG. 2A. is an overview of a dual intervention system as described herein.

Although the following detailed description contains many specifics for the purpose of illustration, a person of ordinary skill in the art will appreciate that many variations and alterations to the following details are within the scope of the disclosed technology. Specific examples are used to illustrate particular embodiments; however, the disclosed technology described in the claims is not intended to be limited to only these examples, but rather includes the full scope of the attached claims. Accordingly, the following preferred embodiments of the disclosed technology are set forth without any loss of generality to, and without imposing limitations upon the disclosed technology. Further, in the following detailed description of the preferred embodiments, reference is made to the accompanying drawings that form a part hereof, and in which are shown by way of illustration specific embodiments in which the disclosed technology may be practiced. It is understood that other embodiments may be utilized, and structural changes may be made without departing from the scope of the disclosed technology. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In the description that follows, the disclosed technology will be described with reference to acts and symbolic representations of operations that are performed by one or more computers, unless indicated otherwise. As such, it will be understood that such acts and operations, which are at times referred to as being computer-executed, include the manipulation by the processing unit of the computer of electrical signals representing data in a structured form. This manipulation transforms the data or maintains it at locations in the memory system of the computer, which reconfigures or otherwise alters the operation of the computer in a manner well understood by those skilled in the art. The data structures where data is maintained are physical locations of the memory that have particular properties defined by the format of the data. However, while the disclosed technology is being described in the foregoing context, it is not meant to be limiting as those of skill in the art will appreciate that various of the acts and operation described hereinafter may also be implemented in hardware.

Crisis states are precipitated by the human stress response. Stress is a biological and physiological response experienced on encountering a threat that we feel we do not have the resources to deal with. A stressor is the stimulus (or threat) that causes stress. Sudden and severe stress generally produces: Increase in heart rate and strength in heartbeat, Shifts in blood flow, Changes in speed and depth of breathing (lungs dilate), Increase in sweating, Increase in bodily movement, Vocal distress, Decrease in digestive activity, and Liver releases glucose for energy.

The human body determines whether a situation is stressful. The decision is made based on sensory input and processing, and on stored memories. If the situation is judged as being stressful, the hypothalamus is activated. The hypothalamus in the brain oversees the stress response. When a stress response is triggered, it sends signals to two other structures: the pituitary gland and the adrenal medulla.

When the pituitary gland is stimulated, it secrets adrenocorticotropic hormone (ACTH) which stimulates the adrenal glands to produce the hormone corticosteroid. Cortisol enables the body to maintain steady supplies of blood sugar to help a person cope with the stressor and return to normal.

The hypothalamus also activates the adrenal medulla, which is part of the autonomic nervous system (ANS.) The ANS is part of the peripheral nervous system that acts as a control system, maintaining homeostasis in the body. The activities are performed without conscious control.

The adrenal medulla secretes the hormone adrenaline. This hormone gets the body ready for a fight or flight response, which is ascertained by measuring one or more of the biological and/or physiological reactions detailed above.

Adrenaline leads to the arousal of the sympathetic nervous system that creates changes to the body thereby leading to a "crisis state." There is considerable variation in the level and type of hormones released by different people in response to different stressors, thereby warranting a computer-driven, multisensory, conscious and unconscious approach to crisis state detection and intervention.

There are several types of situations that can be considered human-crisis situations and/or lead to crisis operating states in humans. People in these situations or suffering from these conditions can feel accelerated and/or elevated states of arousal that includes agitation, restlessness, fatigue, muscle tension, sleep disturbances, panic attacks and more. A crisis state can cloud human judgement, feel highly uncomfortable and stressful, and induce erratic, unanticipated and/or unexpected behaviors. These behaviors can have detrimental or deadly consequences for oneself and others; one's life and livelihood and that of others. Human crisis-state drivers can include: Family Disruption or Disturbance—e.g., divorce, death, accident, Natural Disasters—e.g., flooding, tornadoes, any situation created by a weather disorder, Assaults on Humanity—e.g., acts of terrorism, mass shootings, robbery, prolonged bullying, Suicide, Economic Changes—e.g., loss of job, medical bills, theft of identity or wallet, Life Events—e.g., death of a loved one, birth of a child, any disturbance to daily activities, Mental Disease or Disorder—e.g., anxiety disorders, bipolar disorder, and Organizational Factors—e.g., culture shock due to merger, risk of unemployment, friction inside the community.

The foregoing situations each align with one of three broad areas that affect human stress levels: 1) Personal Factors (e.g., mental disease or disorder,) 2) Physical Environment Factors (literally, the spaces that contain us,) and 3) Social Environment Factors (e.g., organizational culture). We tend to think of stress and anxiety—the precursor to crisis situations—as an individual phenomenon. Group stress is also a very real—but underrecognized—phenomenon.

Human adaptation strategies to difficult and harmful social (cultural) environment conditions can be individual in nature (i.e., each individual thinks and acts independently) or they can be "collective" in nature meaning that individuals think and behave as a group instead of as independently thinking and behaving individuals that comprise the group. In high stress environments, these collective coping behaviors can be particularly damaging. In some instances, these socially-driven behaviors include, diffusion of personal responsibility, blind obedience to authority, uncritical conformity to group norms, and passive tolerance of damaging or cruel behaviors through inaction or indifference. With group stress comes herd behaviors. Herd behavior is a phenomenon in which individuals act collectively as part of a group, often making decisions as a group that they would not make as an individual. In short, herd behavior is about making a decision based in part on the behavior/choices of others. Dysfunctional social environments (cultures) can lead to dysfunctional group behaviors because the social contexts in which humans operate (home, workplace, community) influence our interpretation of the emotional "tune" of a situation—e.g., "is it a threat or not?" Furthermore, the behaviors of others in the environment influence—and can even dictate—how individuals respond to a perceived "threat", and how they are supposed to act to be in alignment with prevailing group thinking and behaviors. Social environments—and humans' fundamental desire to fit into them—have tremendous power to alter the mental representations and behaviors of both individuals and groups. Certain organizational cultures create conducive environments for dysfunctional individual behavior and group behavior such as unhealthy collective stress responses, including inaction.

Harmful collective-coping and herd behaviors materialize when group stress is elevated and escalating toward crisis levels, which occurs most in overly stressed environments or full-on "toxic" social environments which are environments that are ineffective as well as destructive to its members, and include the possibility of escalation to violence. Common dysfunctional collective coping behaviors that can cause damage to self and others include: Conflict tolerance, Intention to change the situation without any action to support change, Changing the interpretation of the situation—i.e., to make "sense" of it through misguided storytelling to bring order and understanding, Rationalization attempts, Projection of the undesirable behaviors of oneself onto others, Resignation—i.e., psychological disengagement, Immobilization—i.e., doing nothing to intervene, Minimizing the problem—especially when only one person is hurt, and Redefining the meaning of the situation to make it more acceptable. In the case of "rationalization" behaviors by a group of employees, for example: One employee may be repeatedly bullied by a small group of colleagues such as project teammates. Other colleagues in the company who witness the group behaviors over time may rationalize them as "okay" because they tell themselves that the bullies are "teaching him a lesson" when in fact, the behavior is detrimental to the person at best, and potentially inhumane at worst. Rationalizing harmful behavior is a common collective-coping mechanism in environments where collective stress is high. Many people have been a part of a dysfunctional, or at its most extreme, "toxic," culture at some point (school, church, organization, etc.), and so they understand the idea of a negative organizational "culture"— perhaps more so than the idea of a negative "social environment"—even though as used herein, they mean the same thing.

"Toxic" is the name given to social environments where group stress has escalated to such a severe level that the environment is deemed to be ineffective as well as destructive to people. For example, toxic workplace environments are a leading cause of workplace violence such as physical assaults and threats of assault, directed toward persons at work or on duty, and include verbal violence (threats, verbal abuse, hostility, harassment, and the like) that can also cause significant psychological trauma and stress, even if no physical injury takes place.

Group stress and toxicity feed each other. Although operating in a toxic environment can be a major source of stress in itself; group stress also feeds toxicity in the environment. The interaction between stress and toxicity can create a damaging cycle if left unchecked. One way to break that cycle is to reduce group stress levels.

Collective stress and/or the collective stress response emerges as a response to two types of "threats" to the group: (1) an attempt to adapt to a social environment that is imperfect or experiencing tremendous change and transformation (risk of unemployment, continuously changing customer or stakeholder needs that are impossible to meet, poor client satisfaction, culture shock due to a merger or acquisition, work overload, pressure toward more autonomy), or (2) friction inside the community (toxic leadership, undervaluation of a group of employees, "penal colony" behaviors used to physically or socially exile individuals and separate them from the larger group.).

Like the social environment, the physical—or built—environment can enhance or hinder wellbeing. A literature review of fifty research papers examining the relationship between office space features on employee health and wellbeing found that environmental aspects that encourage physical activity, enable (day) light, allow individual control, and incorporate green and blue spaces are positively related to health and wellbeing. Similarly, negative physical environment attributes such as loud noise, crowding, low mobility and poor lighting, to name a few, negatively impact mental health. Yet these environmental characteristics are commonplace in myriad organizations and group settings today. In fact, known best practices are rarely incorporated into workplace design and, today, any modifications to physical environments (through IoT) are driven by cost and efficiency factors. Social environmental (culture) factors—and the rising and falling group stress levels they induce—are not priority considerations in setting a physical environment. This is a monumental gap because social and physical environments that are stabilized and calibrated to enable groups of people to function within their normal operating state range enhances employee physical and mental health, reduces collective stress responses, mitigates crisis encounters such as workplace violence, and increases productivity and innovation.

Recall that three factors affect human stress levels: personal factors, physical environment factors, and social environment factors. The interplay among them is powerful. Organizations cannot change people; they can, however, change the social and physical environments that contain the people and shape their thinking and behaviors. This is the fundamental idea behind the group-crisis-state intervention system of the disclosed technology.

Automated interventions, like those outlined here, that positively reduce collective stress thereby reducing harmful collective coping behaviors and herd behaviors by modifying the social and physical environment, mitigate injurious crisis outbursts and outcomes that are a byproduct of illogical, unfocused individual and group thinking and behavior when the group stress response has been triggered.

In some embodiments, the disclosed technology is focused exclusively or primarily on detecting group stress and on activating a sensory-type response that is directed at the group as a whole by making tangible changes to the physical environment, such as improving light intensity or color of the light in the building, increasing natural air flow by opening windows, activating the movement of a wall partition up or down and the like. In other embodiments, the disclosed technology, when individual data is not aggregated and anonymized, also includes activating responses that are customized and directed toward different individuals differently, such as personalized modifications to workspaces or providing apps from the app sub-collections that are tailored to the user based on his/her self-report.

In contrast to other systems that use wearable devices only—the disclosed technology utilizes both wearable devices (on-the-body) and non-wearable devices (off-the-body and building and other surveillance technology) to determine a crisis state of the group or an individual in a group. The disclosed technology does not infer a state of mind, and does not attach any judgement to it—i.e., good, or bad. In the system of the disclosed technology—through on-the-body sensors, off-the-body sensors (and, in some embodiments, user self-reports)—the body of the group "speaks" (via physical, behavioral, and/or cognitive indications) and if the group's "body" indicates that it is outside of the normal range, then an intervention occurs. The person also weighs into the disclosed technology—for initial training of the system purposes, for ongoing system calibration to identify any changes to the normal and/or elevated group-crisis state, and for the user self-reporting mechanism. The disclosed technology does not apply an "antidote"—there's no "medicine" administered to counteract a mind state. The disclosed technology implements an intervention that is either conscious (applied to influence the social environment) or unconscious (applied to influence the physical environment, such as changing a thermostat, sending instructions to a system that changes automated doors, walls, and/or windows.) The conscious intervention drives a behavioral response by the individual or group, which they may choose or not choose to engage with.

Some prior systems categorize mind states into three distinct categories, for example Sinking, Mindful, and Scattering, that are detected as individual phenomena and that are addressed on an individual basis. In contrast, the disclosed technology just identifies an elevated human-stress response—from the individual and/or group—and determines COLLECTIVE STRESS phenomena, and then addresses the intervention on a group basis. Again, the disclosed system does NOT infer a state of mind like prior systems. Further, some embodiments of the disclosed technology do not ignore the normal state, but instead optionally provide positive reinforcement—e.g., an "atta girl", or "atta boy!"

In some embodiments, the disclosed technology provides a group report reflecting aggregated data of the group. Any individual data utilized to determine the group state is anonymized and is not stored or identifiable in any way, in order to encourage individuals to present accurate self-reported data to the group-intervention server so that appropriate feedback and interventions can be presented to the group. In some embodiments, the group-intervention servers of the disclosed technology use artificial intelligence, machine learning, and/or deep learning to continuously obtain data and/or user feedback to improve the system's determinations of, and interventions for, collective stress.

FIG. 1 lists the three drivers of human stress. The SOCIAL ENVIRONMENT and PHYSICAL ENVIRONMENT Factors are addressed by the disclosed technology herein.

Figure 2B:
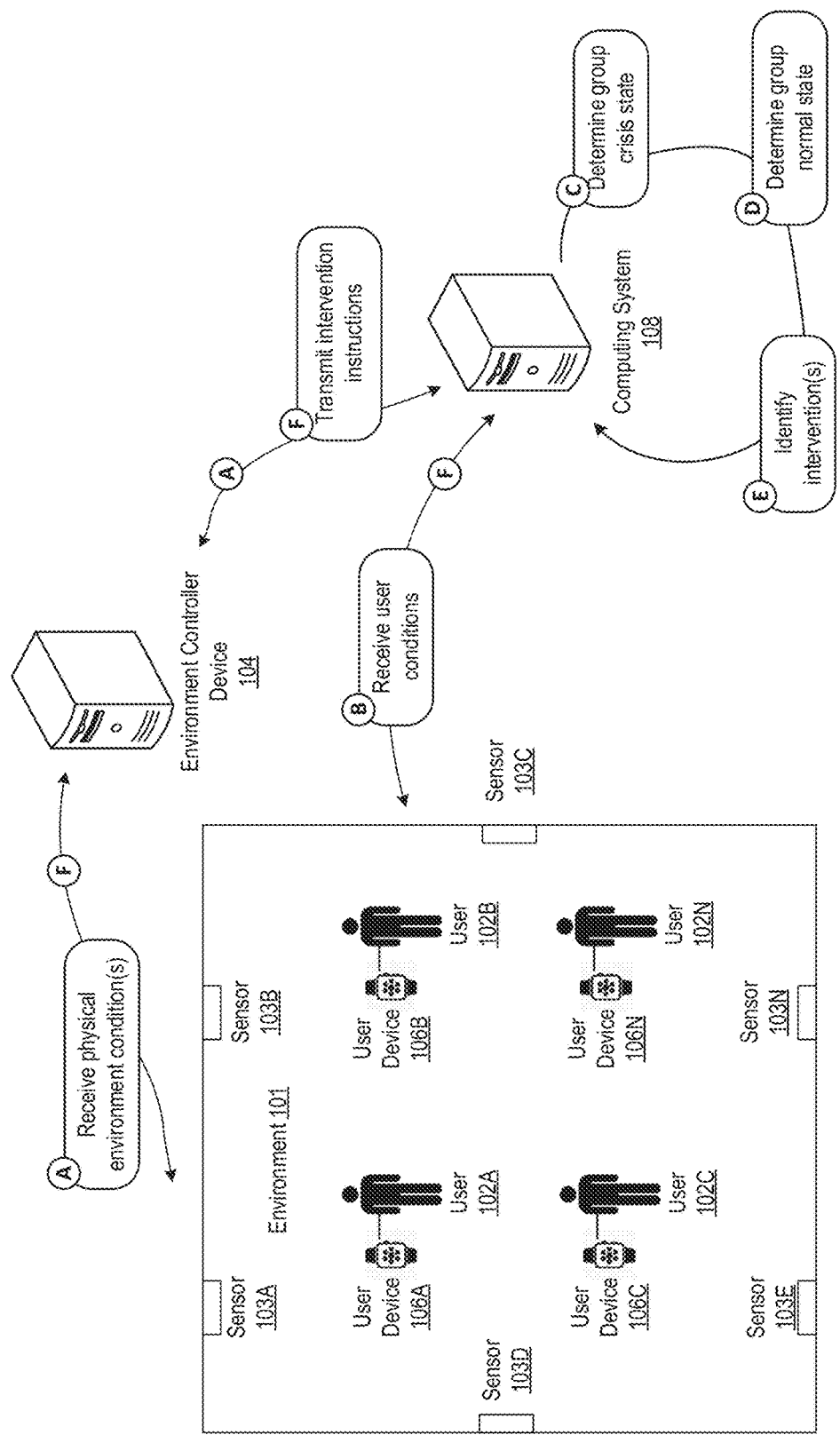
FIG. 2B is a block diagram that represent some embodiments of the disclosed technology.

FIG. 2A is a visual depiction of the overarching system structure and approach to group crisis state intervention that includes both PROCESS #1 and PROCESS #2. FIG. 2B is a block diagram that represent some embodiments of the disclosed technology. Referring to both FIGS. 2A-B, human crises states—the human stress response—is an insidious invader to human health that sneaks in and takes over hundreds of different mind and body pathways if we aren't vigilant. Bringing a group (or individual) down from an elevated state of physiological distress can require a full-on attack that involves constant control over human HEADS (COGNITION) and human BODIES (SENSES—PHYSIOLOGY). The disclosed technology can ambush group crisis states via a multiplicity of UNCONSCIOUS (e.g., sensory-based physical changes to the built environment) and CONSCIOUS (e.g., interactive software applications) interventions delivered IMMEDIATELY through myriad user and building devices at an ongoing basis to improve environmental factors, stop rising physiological stress levels, and return the group to their normal operating state. Multiple devices can be used in the system because, depending on where the devices are placed on the human body, or in the built environment, and/or the role the devices play, each device can allow for sensing different physiological attributes that drive the human stress response, different sensory attributes that contribute to a positive or negative physical environment, and different cultural attributes that contribute to a positive or negative social environment or "organizational culture." In addition, these devices allow for many different types of interventions—and combinations of interventions—both CONSCIOUS and UNCONSCIOUS. The DUAL INTERVENTION system can provide for enhanced system efficacy. UNCONSCIOUS interventions can be largely imperceptible and include SENSORY-TYPE interventions—sight, sound, taste, touch, smell—made via the building sensors to tangibly modify the built or physical environment. CONSCIOUS INTERVENTIONS have a different job. CONSCIOUS INTERVENTION activities described herein can be software applications that consume and engage the users in the group by offering another, different form of IMMEDIATE intervention. The app collection can be comprised of six app sub-collections each aligned with a different proven social environment enhancer that diffuse crisis states (e.g., Access, Choice, Consistency, Connection, Communication, Conflict Resolution.) Just like there are multiple devices and device combinations enabled by the system to sense rising stress levels and intervene, there can also be many different immediate intervention types made possible by the five or more broad types of sense-influencing UNCONSCIOUS interventions and six or more broad families of cognitive-influencing CONSCIOUS interventions. The interventions delivered and described herein can be IMMEDIATE by design. Individuals in a crisis state need IMMEDIATE interventions to help them manage the critical MOMENT of heightened physiological arousal. Because groups are comprised of individuals, our interventions can be centered on swift, effective, IMMEDIATE de-escalation techniques, however, because group stress is a complex function of the individuals in the group, and we know that not all users will engage or de-escalate at the same time despite the immediacy and mass release of the intervention, we know that there can be a lag in response time between when the intervention is applied and the time that a favorable reduction in group stress will be achieved. So, while IMMEDIACY is equally as important to the group crisis state intervention system as to individual crisis state intervention system, the impact of a group intervention is less immediate than the impact of an individual intervention simply because of the inherent complexity of group stress.

FIGS. 2A-B depict users 102A-N in a physical environment 101. The users 102A-N can be employees and the environment 101 can be an office or workspace. Each of the users 102A-N can have user devices 106A-N. The user devices 106A-N can be wearable devices, such as smart watches, and/or mobile devices (e.g., smartphone, tablet, laptop, computer). The physical environment 101 can also include one or more sensors 103A-N. As described throughout this disclosure the sensors 103A-N can be configured to measure real-time conditions of the physical environment 101, including but not limited to room temperature and/or user movement.

A computing system 108 can be in communication (e.g., wired and/or wireless) via a network with the sensors 103A-N and/or the user devices 106A-N. The computing system 108 can be configured to determine group stress levels and interventions to reduce group stress in the environment 101, as described herein. The computing system 108 can also be in communication with an environment controller device 104. The device 104 can be configured to monitor and/or control the sensors 103A-N. Moreover, the device 104 can be configured to control and monitor operations and/or conditions of the physical environment 101.

The user devices 106A-B and the sensors 103A-N can sense real-time conditions of the users 102A-N and/or the environment 101. The computing system 108 can receive sensed physical environment conditions in step A and/or sensed user conditions in step B. Steps A and B can be performed in any order and/or at different times. The computing system 108 can determine a group crisis state based on the received conditions in step C. The computing system 108 can also determine a group normal state in step D. In some examples, the normal state can be determined based on historic information that is collected and stored about conditions in the environment 101. Moreover, step D can be performed at any time. The computing system 108 can identify one or more interventions in step E. The interventions can be intended to lower the collective of users 102A-N from the group crisis state identified in step C. Next, instructions to implement the interventions can be transmitted to the environment controller device 104 and/or the user devices 106A-N. The environment controller device 104 can then prompt one or more of the sensors 103A-N to perform actions that change certain characteristics of the environment 101, as described further below. The steps A-F can be continuously performed or until the computing system 108 determines that the group of users 102A-B lowered from a crisis state to the group normal state.

Figure 3:
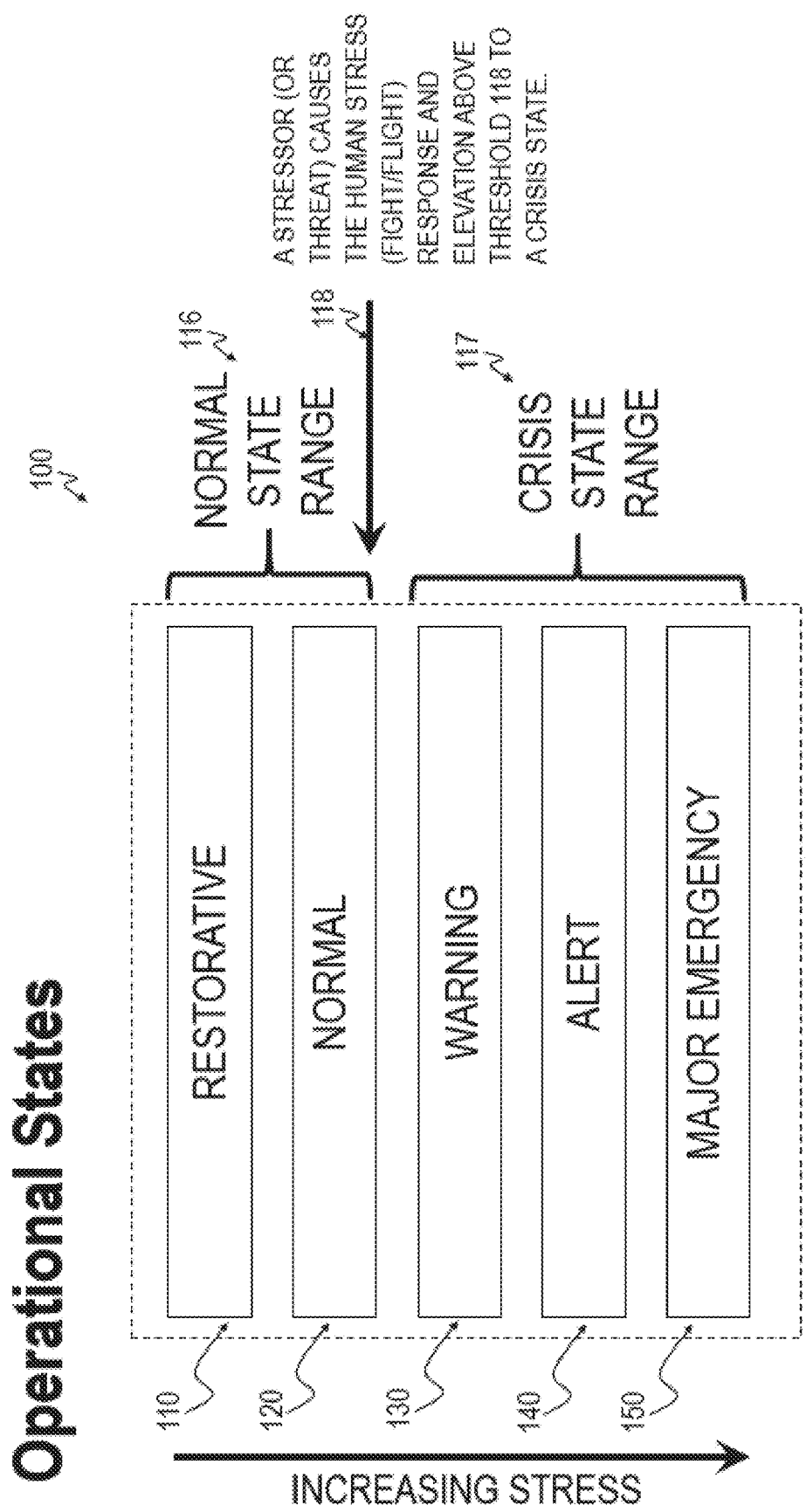
FIG. 3 is a is a process for determining operational states.

FIG. 3 is a block diagram that represents a categorization 100 of operating states, according to some embodiments of the disclosed technology. In some embodiments, categorization 100 includes restorative state 110 (representing the state whereby an individual or the group is capable of restoring and/or attaining restorative benefits; a relaxed, calm state of being), and normal state 120 (representing the regular, natural state that conforms with the median or average standard of the individual or the group; the baseline), wherein, at a high level, restorative state 110, and normal state 120 are considered to be the "normal state range" 116, in that the person or the group of persons are coping well in their environment; their thinking and behavior is reasonable, logical, and abstract. In some embodiments, categorization 100 also includes warning state 130 (representing the state immediately following a threat that triggers the group stress response; agitation results, indicating a possible or impending danger, problem, or other unpleasant situation), alert state 140 (representing a state of escalation and acceleration; agitation is progressing to aggression), and major-emergency state 150 (representing the peak crisis state where thinking and behavior are concrete, illogical and unfocused; the risk of outburst is high), wherein warning state 130, alert state 140, and major-emergency state 150 form a range of crisis states 117 that would benefit from the detection and intervention systems and methods of the disclosed technology.

In other words, FIG. 3 represents a basic categorization 100 of operating states on a continuum containing five core states RESTORATIVE 110, NORMAL 120, WARNING 130, ALERT, and MAJOR EMERGENCY 150. These states further combine into two higher order operating states. Restorative 110 and Normal 120 combine to form a NORMAL STATE RANGE 116, and Warning 130, Alert 140, and Major Emergency 150 combine to form a CRISIS STATE 117. The crisis state 117 can be characterized as such because, in this state, the group of persons are experiencing accelerated and/or elevated states of arousal brought on by a stressor or stimulus (or threat) that caused the human stress response or flight/flight response or because of a hyper-stressed social environment that has elevated to a harmful, toxic state. Since a crisis state 117 can induce erratic, unanticipated and/or unexpected behaviors, the disclosed technology is designed to intervene as soon as a group of persons transitions from their baseline NORMAL STATE 116 to their CRISIS STATE 117. By design, the computer-implemented system does not intervene with a crisis intervention when the group is their NORMAL STATE RANGE 116 as there is no risk of damage or danger to self or others. The system may, however, intervene with a positive—conscious or unconscious—reinforcement or reward, for example, delivered via the building sensors (e.g., open a sliding door to an outdoor common picnic area) or interrupt app engagement with an AI/Smart Coach-based positive affirmation if the persons are able to sustain a normal state range for an extended period of time.

People want to be free from crisis operational states. Crisis states are precipitated by the human stress response, disrupt normal physical and behavioral functioning, and drive unintended/undesired actions that can result in irreparable damage to oneself or others' physical health and wellbeing and/or overarching life or livelihood.

As shown in FIG. 3, individuals and groups of persons embody a range of operational states at any given time from a Restorative State, to a Normal State, a Warning State, an Alert State, and finally a state of Major Emergency. When a person or group of persons are in an elevated state, i.e., that which is beyond their baseline individualized or collective normal state range 116, and instead in the crisis-states range 117 (including warning state 130, alert state 140, and emergency state 150), they may find themselves out of control and/or unable to cope or make decisions in a manner that leads to their own or others' best interests. Crisis states 117, for many members of the population, are often prolonged and/or recurring, and can lead to harm to self and others, including acts of violence.

FIG. 4 is a block diagram of a system 202 involving the detection and intervention of a group-crisis state, when this technology is utilized at the human-group level, according to some embodiments of the disclosed technology. In some embodiments, system 202 includes a user device 210, a building sensor/device 261, and a group-intervention server system 260 that communicate with each other via network 299 (which includes wired and/or wireless communications). In some embodiments, each user device 210 includes a communications interface 211 (such as a cellular phone interface that sends data to and receives data from server system 260, and/or Ethernet, Modbus, TCP/IP, or Bluetooth technology that connects devices and servers), and one or more input sensors 212. In some embodiments, input sensors 212 include on-the-body sensors for heart rate, perspiration, skin resistance, physical movement and/or orientation, speed and depth of breathing, blood flow, vocal changes, muscle tension, metabolic responses and the like. In other embodiments, input sensors include off-the-body sensors for group vocal speed, collective physical movement and/or concentration of people, for example, as well as direct user input/self-reporting as it relates to the current state and effectiveness of the social and physical environment. In some embodiments, server system 260 includes one or more group-specific databases 261 that store past group symptoms and responses and thresholds, and proposed or predetermined responses for a group based on sets of symptoms. In some embodiments, each user device 210 also includes an output and/or alert system 213 for alerting a group of persons via delivery of a group stress-mitigating app to modulate the social environment, while in other embodiments, output and/or alert system 213 is one or more building devices to improve the physical environment (for example, a smart HVAC (heating, ventilation, air conditioning) system that modulates room temperature or ventilation, LEDs mounted on a wall that provide overt visual feedback (such as symbols, colors, intensity modulation (flashing), text and/or other visual indications) to the group, LED room lighting systems that adjust the brightness and/or color temperature of the room lighting to provide subtle or barely perceptible feedback to the group, aroma, scent, perfume, and/or odor emitters (e.g., or as conditionally activated scent-emitters in wirelessly-connected room air "freshener (s)" coupled to an "internet of things" (IoTs), wherein they are activated by heat to emit a predetermined perfume odor) that provide smell feedback to the group. In some embodiments, the one or more input sensors 212 are also in a separate device, such as a camera or other off-the-body device, that is part of an overarching building automation system that serves as the communications interface 211 and evaluates group stress levels by obtaining a group physiological measures. Thus, in some embodiments, user device 210 is implemented as a multi-part system of building sensors (remote-from-the-person) and wearable device portions (on-the-person) that include one or more building or wearable sensors 212, one or more building or wearable alert/output devices 213, and one or more communications interfaces 211, wherein these communicate data among themselves and to and from server 220. In some embodiments, building sensors take biometric measures ("off-the-body" sensor), and in other embodiments building sensors are utilized only to evaluate the state of the physical environment. In all embodiments, there is an element of self-reporting/user-generated inputs captured via user devices created expressly for that purpose. In some embodiments, one or more portions of the intervention server 220 is implemented as software that executes within a user's personal computing device (such as a smart cell phone, personal computer, or tablet), and the communications interface to a wired or wireless network is eliminated for such functions. In some embodiments, a smart building hub serves as the communication interface 211 between one or more input sensors 212, such as a camera or microphone and output alert/output devices 213 that comprise building and IoT-enabled devices and systems, including entertainment systems, smart sensors on thermostats, lightbulbs, outlets and switches, door locks and sensors, security system, fans, window treatments/coverings, and the intervention system/server 220. In some embodiments, one or more portions of, or the entirety of, the intervention server 220 is implemented as software the executes within the smart hub which also serves as the communications interface 211. In some embodiments, the group-intervention server 220 uses artificial intelligence, machine learning, and/or deep learning to continuously obtain data and/or user feedback to improve the system 220's determinations of, and interventions for, group stress.

The disclosed technology provides a computer-implemented method and system 202 for detecting and intervening to correct or improve group-crisis states. System 202 of the disclosed technology includes a plurality of components, connected by a computer network which may be wired or wireless. The core of system 202 is the intervention system/server 260 which can be a cloud-based server, the same server as the user device (i.e., a program running and using a database within the user's device), or another server. Intervention system/server 260 has a processor, memory and a communication interface that allows intervention system/server 260 to transmit data and values to/from other components in the system 202. Importantly, the intervention system/server 260 also includes the intervention determiner, which receives data from the user device(s)—"on-the-body" (and/or "under the skin"), "off-the-body," and remote sensors—e.g., the building sensors, and directly from users who provide periodic, ongoing evaluations of the social and physical environments. The combination of biometric measures (on-the-body and off-the-body) and the user self-report on the social and physical environments are processed by the intervention determiner using one or more computational methods to ascertain the group stress level. If group stress levels exceed the normal operating state, the system implements a dual intervention by modifying the physical environment via building sensors and presenting users with a group intervention app aligned with one of six positive environment-promoting and engaging software applications.

In addition, the intervention system/server, where needed, translates individual biometric measures captured to group measures via the use of machine learning algorithms that are applied for biometric fusion to arrive at multimodal biometric system and group measure. ML algorithms include, among others, Gaussian Mixture Models (GMMs,) Artificial Neural Networks (ANNs,) Fuzzy Expert Systems (FESs,) and Support Vector Machines (SVMs.) In addition to the algorithms used for biometric fusion, the current system uses methods to structure and group the data into distinct groups (e.g., kmeans), for supervised learning (e.g., k-nearest neighbor), and/or for model learning/rule learning from aggregated data (e.g., AQ algorithm). In some embodiments, artificial intelligence and/or machine learning are used in the overall assessment, interventions, and continuous feedback by which the system initially "learns" to determine group-crisis states and appropriate group interventions, and then later continuously improves itself over time. In some embodiments of all the intervention servers described herein, thousands or hundreds of thousands of parameter combinations are presented to the machine-learning algorithms, wherein each one of the combinations is indicated as "group-crisis state" or "group-normal-operating state" and the algorithm automatically performs its own analysis in order to learn which combinations of parameters would be a group-crisis indicator. Further, based on self-report data from users regarding the overall and current state of the physical and social environment (both before a system intervention is applies and afterwards) as to which situations were crisis state and which interventions were successful, the algorithm improves over time as to the algorithm's accuracy in detecting crisis states, and in which interventions worked to improve the group operating state and which are contra-indicated.

The intervention system/server also transmits data to and from the database(s) that capture and store group-specific data and values. The database(s) are part of the overarching system and function primarily for data storage and retrieval of group information and values. These values are captured and reported to all users in the group in the form of a software application data dashboard that allows them to review, monitor and act upon/influence the current state of the social environment, the physical environment, and the variables that influence each—for example, via real-time conscious intervention apps aligned with one of six social environment (culture) boosters (Access, Choice, Consistency, Connection, Communication and Conflict Resolution) or by modifying aspects of the physical environment such as the temperature in the workplace or moving a wall partition to reveal green/blue spaces outdoors that are natural stress reducers. Users are not given carte blanche to make sweeping changes to the overarching physical environment; they are empowered to control their immediate surroundings/workspace and can make suggest changes to the built environment that cannot be implemented immediately. Administrators have broader responsibility to influence the organizational physical environment.

Another component of the system are the user device(s) 210, such as shown in FIG. 4. In some embodiments, these devices 210 are multifunctional. They have a communication interface 211 that allows them to communicate with the intervention system/server 260 and database(s) 261 via the network. The user device(s) 210 (on-the-body and off-the-body) also operate as input sensor(s) obtaining group biometric values to assist with determining the operating state of the group along with the user self-reports. In addition, the user device(s) 210 function as output device(s), alerting the group that the crisis threshold 118 has been surpassed which triggers the delivery of a conscious crisis state app intervention and data dashboard. This alert system and the conscious (social environment influencers) and unconscious interventions (physical environment influencers) are the mechanisms that diffuse group crisis states and stop crisis escalation to circumvent catastrophic crisis-driven outcomes.

In some embodiments, the system 202 utilizes one or more user devices/input sensors 212 to monitor, measure, and detect the collective operating state of a group of persons, via obtaining measurements/values of physical (e.g., heartrate, blood flow, breathing, bodily secretions, muscle tension, body metabolism) and/or behavioral (e.g., movement, voice) indicators, or any combination thereof. These measurements can be taken via "under-the-skin"/"on-the-skin"/"on-the-body" or remote/"over-the-skin"/"off-the-body" input devices. These biometric values obtained by sensors 212 are communicated from the user device(s) via the communication interface to the intervention system/ server 260 over a network 299 (wired and/or wireless.) In addition to the biometric values obtained, the group intervention system is powered by two other inputs: 1) traditional IoT/building automation sensors which keep track of the status of the physical environment so that if the group operating state is determined to be elevated, it can be modified and 2) user input in the form of ongoing, periodic self-ratings of the social and physical environments which are aggregated and utilized along with biometric values to determine the overall group stress level.

In some embodiments, the intervention system/server 260 receives numerous values at various points in the process from all four input areas and sends them to the internal intervention determiner 224 (in some embodiments, a program running in processor-memory 222) that assesses whether the group has achieved a crisis state by comparing the values it receives against a predetermined baseline or threshold value established using historical data and stored in database 221. If the intervention determiner 224 detects a crisis state 117 (i.e., above the threshold 118), intervention determiner 224 will apply DUAL INTERVENTION methods—both methods referred to herein as "conscious" (software intervention providing group feedback that is readily perceptible by the group), and "unconscious" (sensory changes to the building that are barely perceptible or not perceptible by the group)—to diffuse the crisis state 117 by improving the physical and social environments and returning the operating state to a normal state range 116. If the intervention determiner 224 does not detect a crisis state 117 (i.e., a state below the threshold 118), then, in some embodiments, no intervention occurs.

Once the intervention determiner 224 makes a crisis/no crisis determination, the data are transmitted to the database 261 for storage and subsequent processing and retrieval; and 260 sends data back to the user device(s) via the communication interface 211. The intervention determiner 224 in group-intervention server 260 also transmits data to the user device 210 expressly for reporting purposes so that individual members of the group can review, monitor, and act on the social and physical environment data for which they permission and access to do so. In some embodiments, the intervention determiner 224 utilizes artificial intelligence and/or machine learning and/or other computational methods and algorithms to compare input data/values from the user device(s) 210 to historical values stored in the database 261 to make its determination and/or to transform individual biometric values to group biometric values. Based on the assessment, the intervention determiner 224 may/may not implement an intervention.

In some embodiments, the present technology imparts no crisis intervention, alert or action when the collective operational state of a group is determined to be within their non-crisis, normal state range 116 (which includes both normal state 120 and restorative state 110)—a range 116 that is determined by the intervention determiner 224 at a collective/group level by an initial computational training phase of system 402 that is calibrated and updated on an ongoing basis, in some embodiments, via systematic processes using Artificial Intelligence, Machine Learning, and/ or other computational methods and algorithms, as well as user-driven or administrator driven readings and refinements. The present technology optionally imparts positive feedback to the group of users if operating in a sustained normal-state range in the form of, in some embodiments, a positive change to the physical environment (sight, sound, smell etc.), or a positive action aligned with one of the system's apps that are part of an overarching collection of apps designed to improve the social environment (culture) based on six proven culture-enhancing areas.

When the intervention system/server detects a transition from the normal state range 116 (which includes normal state 120 and restorative state 110) to a state in the crisis state range 117 (which includes alert state 130, warning state 140 and major emergency state 150), the intervention system/ server 220 communicates via the network 299 to the user device(s) 210 and the building devices transmitting data that triggers, in some embodiments, the alert system 213 to activate the DUAL INTERVENTION method: (i) The first intervention emitted by the user device(s) is UNCONSCIOUS (barely or not perceptible) to the user/users and involves a modification to the physical environment that is calibrated to the group's collective physical and/or behavioral indicators and current collective operating state and is designed to unconsciously modulate the collective crisis state and the related physical and/or behavioral responses via direct sensory/physical environmental feedback delivered through the IoT/building automation sensors. For example, shifts in environmental/situational factors are often imperceptible to human beings—a shift in lighting, a change in background music, emission of a pleasing aroma—yet these situational factors have tremendous impact on a person's or group of person's physiological operating state. The primary benefit and characteristic of unconscious interventions is that they work in mitigating crisis states without distracting or overwhelming the group of users—i.e., they do not have to DO anything or STOP anything for the intervention to fulfill its purpose. (ii) The second, concurrent intervention, delivered through the same or different user device (which may or may not be wearable), is CONSCIOUS to the persons and involves an alert and/or prompt inviting individuals that are part of the group to engage with and/or deploy a recommended app from a collection of software intervention applications based on prior system application and efficacy. The software apps are specifically designed as social environment/culture boosters (or "improvers") that also serve as crisis state mitigators by providing individuals within the group powerful elements of personal control, or enabling them to connect meaningfully with others, and/or increasing overall organizational psychological safety, for example. In some embodiments, the intervention app collection includes several themed sub-collections each with a history, scientific research, and a practical track-record of success improving social environments/organizational culture, performance, and diffusing physiological stress responses and include tools that improve individual/group (e.g., as of an employee) Access, Choice, Consistency, Connection, Communication, and Conflict Resolution.

The efficacy of the apps—and the organizational (individual and group) behaviors they induce digitally—directly reduce collective stress and positively influence the social environment (culture.) Myriad research shows that the same factors that drive collective stress are also the barriers that preclude organizational innovation and productivity, for example, lack of communication and idea sharing, not enough flexible working technologies, physical layout that supports hierarchy, lack of a systematic/consistent process, no reward and recognition programs, constantly shifting priorities, politics—efforts to sustain the status quo to support entrenched interests, and many more.

A physical environment also influences human physiological stress response. Lighting, sound, and aroma were mentioned previously but there are myriad levers to alter one's current environment or change to an entirely different environment. For example, access to green spaces and being exposed to natural environments, among other positive environmental factors, can be beneficial in reducing physical stress levels.

It is important to note that in some embodiments of the present system, while it is the users in a group of users that must perform some system-recommended activity, it is the computer system that prompts and suggests the optimal activity to a group of users based on historical usage, performance, and efficacy of mitigating the group-crisis state. And, although the alert and/or suggestion is systematically driven by the technology to the user and group, upon receipt of the alert, any one user may choose or not choose to act upon the alert by deploying the intervention. In summary, with the conscious intervention method, while the technology makes a recommendation based on biometric values, environmental assessments, user feedback, and computational processing and algorithms, it is the user that ultimately controls activation of the intervention.

Each user can choose from among many software interventions aligned with his/her preferences. Or—because the system is powered by artificial intelligence, machine learning and/or other computational methods and is continually learning and optimizing interventions at the individual or group level—they may allow the system to recommend an optimal software application or interventional tool or experience.

The CONSCIOUS, person-driven software applications and interventions of the disclosed technology induce the person or persons to engage in one of six social environment/cultural promoting areas or categories that directly or indirectly diffuse the collective crisis state via a change in the social environment ("culture.") The crisis mitigation areas deliver crisis relief via one or more intervention app sub-collections which may include, among other themed sub-collections, access/transparency, choice, consistency, connection, communication and conflict resolution—all of which are proven to positively impact the health of the social environment (culture).

The present technology is group adaptive because the intervention system/server, the user device(s), the building sensors, and the user-feedback mechanisms are repeatedly and/or substantially continually transmitting, evaluating, and sharing data via the network (wired or wireless). This ongoing iterative, evaluative communication and data sharing process between core system components allows for adjusting or modifying interventions and/or recommendations, if applicable, to group needs, and the severity, frequency, and duration of their collective crisis states. In addition, the transmission of data to the database(s), importantly, enables a group-portrait that is shared to all members of the group via the system dashboard periodically and consistently for review, monitoring and manipulating, and the data is stored for subsequent manipulation, analysis, or reporting.

The DUAL INTERVENTIONS may occur concurrently or independently, situationally determined by the user, user group or administrator. The intervention system/server, because of its multifunctionality, may use one or more applications or other software to record the timing, duration, and the characteristics of the crisis state, and the group's response to the interventions collectively deployed, and transmit this data to the database(s) for storage, manipulation and/or subsequent processing or retrieval. It should be noted that, in some embodiments, identifiable, individual data is not maintained by the system; rather individual data is utilized to create group values and recommend group interventions. Self-reported feedback on the social and physical environments is utilized to customize and recommend interventions including software applications to each user, in some embodiments, based on their specific feedback.

In some embodiments, the present technology is a learning system on two levels. The first level is computer-driven via simple feedback (such as which response stimulation(s) were provided to the group in response to detection of a given set of physiological symptoms, and how well did those response stimulation(s) work to return the group to a normal collective operating state range), as well as artificial intelligence, machine learning, deep learning, neural networks and/or other computer methods and algorithms that are part of the intervention determiner. The intervention determiner uses one or more of these technologies to learn, over time and training, what interventions perform swiftly and effectively to diffuse the crisis state and return the persons to their Normal State Range as well as for purposes of biometric fusion.

The second level is human driven in that after the intervention determiner concludes that a CONSCIOUS intervention is needed and communicates this to the user device(s) to ultimately reach the users, the person (in some embodiments) or persons implements a chosen method or path. Their action then drives a corresponding physical and/or behavioral response, which the user(s) are no doubt cognitively aware. This user-driven action-response sequence will cause the person/persons to self-assess and/or evaluate the efficacy of the chosen intervention on their crisis state which, in turn, will create greater self and group understanding and drive subsequent intervention best practices and positive collective behaviors. In summary, like the primary computer-driven system, a secondary human-driven system trains the person or persons to learn what interventions perform optimally in each situation, circumstance, environment, operational state and severity thereof.

The DUAL-INTERVENTION system, underscoring the disclosed technology that includes a system and methods, directly and indirectly influences and modulates the collective human stress response.

Still referring to FIG. 4, the disclosed technology comprises components including an intervention system/server 260, which includes a processor 222, memory 222, communication interface 223 and an intervention determiner 224; user or group specific database(s) 261; one or more user device(s) 210, building sensors 251, and user-generated feedback 262-263, which is captured and transmitted via the communication interface 211 over a network 299 (wired and/or wireless) to the intervention system/server 260. The user device 210 further includes one or more input sensors 212 and/or output mechanisms 213 that operate as an alert system.

The present technology uses at least one sensor 212 to read and monitor one or more physical or behavioral indicators (measured remotely from the user's body or "off-the-body," "over the skin," or "on-the-body," "on-the-skin" or "under the skin"), one or more building sensors 251 to monitor the state of the physical environment, and the disclosed technology also elicits user input 262 and 263 to periodically evaluate the general "health" of the social and physical environments. Input devices 212 may be combined or packaged independently or collectively; they may be wearable such as a watch, smart clothing, earphone, or other product, or they may be stationary devices, physically independent from the human body, that are taking biometric measures remotely from the user's body, such as a camera or microphone. Likewise, output devices 213 may be combined or packaged independently or collectively; or they may be wearable or non-wearable such as building devices including entertainment systems, automated window or wall mechanisms, or an HVAC system, device, or sensor. While the number of devices may vary by user and user group, the devices and sensors, in concert with the intervention system/server and database(s) perform the present technology together.

One or more user device(s)/input sensors are designed to read and measure one or more physical or behavioral indicators. In some embodiments, measurements are taken from sensors in contact with the user's body, such as measures of a user's heart rate and strength (via heart rate monitor, electrocardiogram "ECG" or "EKG", electromyograph "EMB"), blood flow (via heat sensors, skin sensors), breathing (via thoracic and abdominal sensors), secretions (via GSR, electrodermal activity "EDA") or "remotely" such as movement (via accelerometer, camera), and voice (via microphone), among other variables and determinants of crisis states. For example, a heart rate monitor may be used to ascertain heart rate variability (HRV); galvanic skin response (GSR) technology may be utilized to ascertain bodily secretions, or a camera may be utilized to determine concentration levels. The computer-implemented system utilizes one or more biometric and other measures and sensors for readily measuring physical and/or behavioral indicators. When these measures are determined to be outside of the normal range, the system implement interventions to positively influence the social and/or physical environments which have a direct impact on the collective stress level.

Once these measures are taken by the user device(s), the data are transmitted via the communication interface 211 over the network 299 (wired or wireless) to the intervention system/server 260. The intervention system/server can be a cloud-based server, can be the same as the user device(s) (i.e., the intervention server being implemented as software that executes within the user's device(s)), or another server. The intervention determiner 224 is designed to ascertain a group stress or operating level; specifically, if the group has collectively transitioned into a crisis state. The determiner 224 does this by comparing input data from the user devices (s) 210 to historical data and a threshold value in the database 261 using computational measures and methods, which may include one or more means such as statistical methods, artificial intelligence, knowledge base, vector space model and any combination of these and/or other methods. The system 260 can use algorithms to translate individual values to a group value for determining a group operating state.

When the intervention system/server 260 determines, via the processor 222 and intervention determiner 224, that the group has shifted into a crisis state, the intervention system/server 260 transmits data via the communication interface 223 over the network 299 to the user device 210/output/alarm system 213 to the building actuators 264 and user devices 265 (e.g., in some embodiments, via an app that elicits and receives anonymized user input (self-reported data) and/or outputs one or more interventions to each person in the group) to deploy dual interventions (i.e., conscious and unconscious) through one or more user and/or building output devices 265. By transmitting data to/from the user device(s), building system, and by capturing inputs from the user directly, intervention system/server, and the database(s), the core system may enable data tracking, data capture, reporting, data analysis and synthesis to optimize user and group performance, and performance of the system and methods. Reporting and sharing of group data is a critical element of the system and essential to ensuring healthy social and physical environments through engagement and empowerment. This functionality is enabled through the system dashboard and provided to members of the group.

The entire systems process—from user device(s)/input sensor(s) (on-the-body and off-the-body) that measure physiological and biological indicators, to the building sensors that keep tabs on the physical environment, to the ongoing user feedback on the health of the social environment (culture) and physical environment that contribute to the overall group stress assessment, to the intervention system/server that receives and processes the data from the input devices and applies computational methods and algorithms to determine crisis levels, to the user device(s) and output mechanism that receive data, alert the user and deploy the dual interventions—is iterative and ongoing.

FIG. 5 is a diagram of a communications process including transmission of data between user device(s) 310 (both remote-from-the-person and on-the-person sensors), building sensors 331 (standard IoT/physical environment evaluation—i.e., other than taking biometric measures), user self-reporting mechanisms 341, (the inputs used by this process for various purposes 302) and intervention system/server 360 (which processes the inputs that are used to determine group stress and an appropriate intervention), according to some embodiments of the disclosed technology. As depicted in reference to FIG. 5, in some embodiments, process 302 includes sensing biometric values 311 from user devices 310 that, in some embodiments, are wearable (such as a smart watch, smart clothing, earphone, belt, necklace or headset on the body of the person) or non-wearable (such as tablet, microphone, camera, smart phone, smart speaker, HVAC system remote from contact with the body of the person). In some embodiments, the user devices 310 may serve the function as an input device (such as sensors 311), output device (such as actuators 361 for group interventions), or, in some cases, such as the case of a smart phone (i.e., conscious app intervention), both input device and output device. In some embodiments, the group-intervention system/server does one or more of the following: elicits and receives 312 biometric values from on-the-body sensors 311, elicits and receives 322 person-indicative values from off-the-body sensors 311, elicits and receives 332 environmental-indicative values from building sensors 331 to assess the state of the physical environment, elicits and receives 342 person self-reported parameters from user devices 341, and then analyzes the data from on-the-body and off-the-body inputs married with user self-reporting to determine a group-operating state that is compared to threshold values 352, and if above a threshold value then transmits 325 and intervention-actuation notification or command to actuators 361 that, based on the command, actuate the indicated intervention by modifying the physical environment via changes to the building sensor settings and influencing the social environment via distribution of a conscious app intervention (e.g., sending instructions to a building system to change automated walls, ceilings, windows, doorways, visual screens, blinds, lights etc.). Else, if the group-operating-state rating is not above the threshold value at 326, the system returns to eliciting and receiving data in block 360 on a continuous or repeated basis to intervene when needed. In some embodiments, the output actuator 361 is used to activate group interventions, and/or building sensors 331 may serve also as such an output device, such as a motor to move wall partitions left or right and/or up or down, a remotely activatable switch to turn an electric device such as lighting or a fan on or off; a multi-color LED to shine light or images against walls, or a dimmer to control lighting. In other embodiments the building actuators 361 also include sensors that serve the function as an input device to provide optional feedback to the output actuators 361, such as a photometer to measure light intensity or a carbon dioxide ($CO_2$) meter to measure air quality or an olfactometer to detect aroma/odor dilution. In some embodiments, the intervention system/server 360 includes, or connects to, a physical device 361, such as a smart speaker, or connects over the network to a server on a different, remote device or in the cloud.

FIG. 5 depicts a subset of the overarching system, specifically, the communication process and transmission of data between the user device(s), the building sensors, the user self-reported ratings, and the intervention system/server. The input/sensor elements of the user device(s) are designed to sense/read biometric values that may be off-the-body ("over the skin) or on-the-body ("under the skin.") For example, an on-the-body breathing rate may be taken from a thoracic or abdominal sensor; or sweating may be ascertained from a GSR sensor embedded into a smart watch. These biometric values are transmitted via the communication interface over the network (wired or wireless) to the intervention system/server which receives the biometric values, converts individual values to a group value, and compares them to historical values and the threshold value in the database. Via a computational assessment process that occurs in the intervention determiner, the intervention system/server ascertains if the new value is above or below the group's crisis state threshold value.

If the value is below the threshold value—i.e., the value at which group shifts from a normal state range 116 to a crisis state range 117, the intervention system/server concludes that the group is operating within their normal collective-operating-state range 116 and signals to the user device/output device and the building sensors—by sending data via the communication interface over the network—that no intervention is needed, in some embodiments. It also sends the values to the database(s) to be stored and to another user device for reporting purposes. If, however, the biometric value is above the group's threshold value, the intervention system/server concludes that the group has shifted into a crisis state. In this case, the system responds by transmitting data to the user device/output device and the building sensor(s) which then actuates one or both dual interventions—conscious (i.e., intervention app to influence the social environment) or unconscious (e.g., sensory changes improve the physical environment—depending on the user or administrator settings/instruction for doing so. All data transmitted to the user device(s) are also sent to the database(s), and used for reporting back to the users in the group and to the administrator via the system dashboard.

Figure 6B:
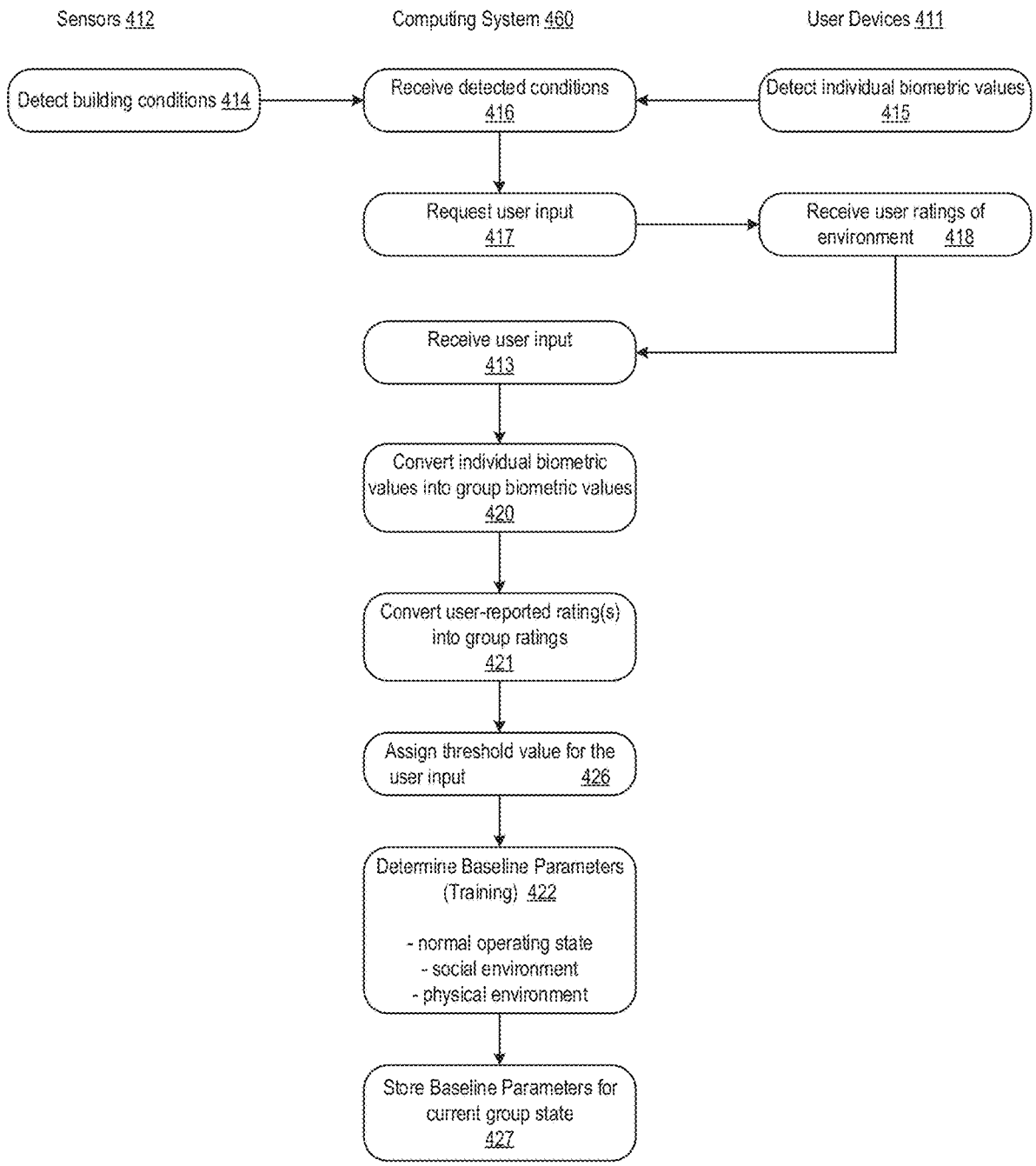

FIGS. 6A-B are diagrams of a process for determining the group baseline operating state, according to some embodiments of the disclosed technology. As depicted in FIG. 6A, in some embodiments, process 402 includes user devices 411 that function as input devices, sensing biometric values, such as heart rate strength or variability via a smart watch, or vocal speed, pace or volume via a microphone in a smart phone. In some embodiments, building sensors 412 include a microphone in smart speaker or a wall-mounted audio/recording device to detect vocal speed, pace or volume, or cameras, ultrasonic or other motion sensors, or FLIR (forward-looking infrared) sensors to sense a change in group velocity or individual speed differences or temperatures of persons. In some embodiments, process 402 requires user and group administrator evaluation and input, and in some embodiments, this can be executed via a smart phone, tablet, or desktop computer. These user values are transmitted via the network to the server 460 and stored into database 461 that holds historical group-specific parameters, as well as system-determined trends in such parameters. In some embodiments, a machine-learning algorithm 480 is used in or with server 460 to learn and improve the software's accuracy in determination of group stress and the effectiveness of group-stress interventions provided by the intervention server 460.

FIG. 6A is a block diagram that represents the training process 402 of determining the group's Normal State Range 116. This process is necessary because every collection of persons has a distinctive set of "normal" physiological parameters or parameter ranges (analogous to a "normal temperature" of 37 C) at which they operate optimally. This Normal State Range can be slow and peaceful for some groups and fast and dynamic for others. This present technology uses methods (e.g., computational algorithms, statistical analysis, database, knowledge base, machine learning) to ascertain the Normal State Range of a group of persons and takes this baseline into account to set the group-crisis-level threshold. The process 402 begins with the user device(s) 411/input sensor(s) which sense the biometric values and transmits the data via the communication interface over the network to the intervention system/server 460. Likewise, the building sensors 412 sense and evaluate the current state of the physical environment and transmit these data to the intervention system/server 460. The intervention system/server 460 sends a signal 413 to the user device(s) 99 (via an app that is part of the system dashboard) prompting the users and administrator to evaluate the social and physical environments and the current operating state—i.e., would they characterize the current state as an elevated state or a normal state? 419. During this training period, the user or administrator enters their response into the appropriate user device, which then communicates the response to the intervention system/server 460, where the set of all such responses is used to set-up and periodically thereafter to calibrate and adjust the threshold level that is used to evaluate symptoms (one or more sets of physiological parameters) that are to be evaluated—either one at a time (moment-by-moment evaluations, each of a single set of parameters) or across a period of time (determining changes in the sets of parameters over one minute, five minutes or an hour, for examples) 480. The user's (administrator's) evaluations initially set the threshold level for the set of physiological parameters or for changes in the physiological parameters, thus training or guiding the intervention system/server 460, which then uses the training data to determine the group's crisis state parameters and threshold level. The system is configured to conduct periodic operating-state measurement, calibration, and reclassification efforts to ensure the crisis state parameters and threshold values are and remain current. Via an on/off switch or other such mechanism, the human user or administrator controls whether these periodic, ongoing threshold training efforts are conducted manually via user or administrator input or are systematically driven utilizing the intervention determiner and its powerful computational functionality.

FIG. 6B is a flowchart of the process 402 as described in reference to FIG. 6A. Sensors 412 can detect building conditions in step 414. User devices 411 can detect individual biometric values in step 415. Computing system 460 (e.g., the intervention system/server 460 in FIG. 6A) can receive the detected conditions in step 416. The system 460 can also request user input in step 417. The user devices 411 can prompt the users (e.g., employees) to rate the physical environment and social environment (culture.) The user devices 411 receive user ratings of the environment (e.g., including a physical environment, such as office and workplace, and a social environment, such as culture) in step 418 and transmit those rating to the system 460. The computing system 460 can receive the user input in step 413.

The system 460 can convert the individual biometric values into group biometric values in step 420, as described throughout this disclosure. The system 460 can also convert the user reported ratings into group ratings in step 421. As a result, the system 460 can assign a threshold value for the user input (e.g., user reported ratings) in step 426. Then, training can be performed by the system 460 in step 422. The training can be performed to determine and adjust baseline parameters for the group. Some of these baseline parameters can include a normal operating state of the group, a social environment of the group, and a physical environment for the group. The system 460 can then store these determined baseline parameters as a current (or baseline) group state in step 427. The baseline parameters can be stored in the database 461, as depicted in FIG. 6A.

FIG. 7 is a block diagram of a dual-intervention system 502, according to some embodiments of the disclosed technology. In some embodiments, process 502 includes user devices 511 that sense biometric parameters 522 such as heart rate (on-the-body) or vocal attributes in individual users, rising vocal speed, pace, or volume in a group of users (off-the-body), building devices 512 that sense building parameters 523 such as temperature, humidity, $CO_2$ levels, sound levels and the like, and devices that elicit and receive self-reported social and physical environment parameters from human users. In some embodiments, process 502 also includes building devices 514 (which may or may not be merged with the same devices as devices 512) that provide unconscious sensory feedback 514 by modifying the physical environment such as outputting a subtle aroma emitted via a building ventilation system, imperceptible audio feedback via an audio system (such as infrasound with frequencies less than 20 hertz), or direct changes to the physical environment such as the automatic opening of windows or the movement of walls or partitions up or down, open or closed while providing conscious feedback to shift social environmental factors 515 in the form of an intervention app presented to the user or group of users with which to engage through a second device such as a smart phone, tablet, smart watch, headset, desktop or other user device. In some embodiments, a machine-learning algorithm 580 is used in or with server 560/565 to learn and improve the software's accuracy in determination of collective stress and the effectiveness of group-stress interventions provided by the intervention server 565. Moreover, as described throughout this disclosure, the server 560/565 can determine whether to provide unconscious and/or conscious interventions 514 and 515 based on receiving the sensed biometric values, physical environment values, and environment (e.g., physical and/or social) ratings (collectively known as received conditions 517) 521, converting received individual values into group values 525, and determining whether the group values are below a threshold value 526. Where the group values are above the threshold value, one or more of the interventions 514 and 515 can be applied.

FIG. 7 represents an exemplified and non-limiting overview of the dual intervention system 502—conscious and unconscious. These dual interventions address the problem of operating state crisis from different angles and apply distinctive solutions and approaches to improve the social and physical environments thereby compounding the impact of the system and the efficacy for the group of users. The dual intervention system is actuated only when the group is deemed by the intervention system/server 565 to have exceeded their threshold level. Without exception, system 502 automatically actuates the unconscious intervention 514, or changes to the physical environment, if the group's biometric values exceed the threshold. The system 502 also takes into account self-reported ratings 524 to implement changes. To actuate the unconscious intervention 514, the intervention system/server 565 sends data via a communication interface over a network to building devices instructing them to emit sensory feedback (taste, touch, sight, sound, smell) calibrated to the physical or biological indicator under measure. The process is generally unconscious to the user and group and is designed to not distract or disrupt their current activity. Instead, it is designed to unconsciously and unobtrusively modulate and mitigate the physical environment thereby mitigating the group crisis state.

Unlike the unconscious intervention system 514, the conscious intervention system 515 has an element of user or administrator control. Specifically, the user or administrator determines, at initial system set-up, if they prefer the conscious intervention to be user-directed or system-directed. If the user or administrator chooses to control the conscious intervention when the threshold level is reached, the user or administrator will be notified by the user device(s)/output device(s) and asked to select one of many conscious interventions/apps from the stress reducing themed app sub-collections. If the user chooses the system to control the conscious intervention automatically when the threshold level is reached, the system will make an app intervention recommendation from the collection based on prior learning of efficacy under similar circumstances. In some embodiments, unconscious interventions 514 are applied primarily to the physical environment and conscious interventions 515 are applied primarily to the social environment.

In some embodiments, even if the person or group of persons relies on system-generated recommendations for software application intervention, the user (or administrator) can override the system to self-select intervention applications.

FIG. 8 is a block diagram of an unconscious intervention system 650 and method 602, according to some embodiments of the disclosed technology. The feedback is designed to modify the physical environment and can be largely imperceptible such as a shift in the color of room lighting, change in background noise or music made possible via a smart entertainment system, or the infusion of fresh, outdoor air brought inside via an intelligent ventilation system.

FIG. 8 represents an exemplified and non-limiting overview of the unconscious intervention 650. This intervention process is automatically actuated if the intervention system/server 565 receives (521) a set of biometric values 517 from the user devices 511/input sensors of the group, wherein the group values combine to a group value that is above the crisis-state-threshold level for the group (522, 525, 526). The set of biometric values 517 also includes social and physical environment ratings received from user devices 513 (524) and physical environment conditions sensed from building sensors 512 (523). In some embodiments, to mitigate the crisis state, the intervention system/server 565 transmits data to the building sensors(s) 512/output mechanism which then provides sensory feedback in the form of modifying the physical environment of the organization and return the group to their normal state. The sensory feedback can be in the form of touch, sight, sound, smell, or taste, depending on the IoT/building automation system of the organization, its sensors, actuator devices and their purpose.

FIG. 9 is a block diagram of a conscious intervention system 750 and method 702, according to some embodiments of the disclosed technology. In some embodiments, system 750, and method 702 includes a plurality of user devices 710 that sense/read 517 biometric values for the group (see FIG. 5 described above) and transmits the values 521 to intervention system 760. In some embodiments, intervention system 760 includes group-intervention system/server 765 that receives 522 the biometric parameters from the group's user devices 710, and optionally receives 524, from users 713, the user-reported social-environment values 521, 515, converts (and optionally anonymizes) the individual user data into group data 525 and determines 526 whether the group values are below the group threshold value—if so, then the group is operating within the normal state range and no intervention is needed. If the values are not below the group threshold value, and if the automated system is active, then a recommendation for a social environment (culture) intervention app (and/or a presentation of dashboard results) is/are sent to one or more user devices (in some embodiments, all group interventions are sent to all users). If the automated system is not active, the app collection (and/or a presentation of the dashboard results) is sent to the user(s) for them to select the app from the collection that is best-aligned to their needs. In some embodiments, when the received biometric values are NOT below the threshold value (i.e., the values are at or above the threshold indicating the presence of a group crisis state), intervention system 760 causes the user device 710 to present to the user an application ("app") recommendation.

FIG. 9 represents an exemplified and non-limiting overview of the conscious intervention system 702. The conscious intervention system is designed to deliver software application interventions aligned with one of six factors proven to reduce collective stress levels elevated by negative social environmental (culture) characteristics. These interventions are also known to improve organizational productivity and innovation. The factors include but are not limited to Access, Choice, Consistency, Connection, Communication, Conflict Resolution. The system is scalable in that there is no hard limit to the number of the software applications that can be developed, included, and offered in each of the crisis-intervention app sub-collections. This scalable feature enhances the overall efficacy and applicability of the basic system for diverse populations, individuals, and groups.

The conscious intervention system has two-modes, user-directed and system-directed. In the system-directed scenario, in some embodiments, the user device(s)/input sensor reads the biometric values, takes a measure of the physical environment via sensors, elicits user input, and transmits the values via the communication interface over the network to the intervention system/server which, via its intervention determiner, senses the values, compares them to historical values and the threshold values stored in the database(s), and makes a group crisis state determination. If a crisis state is ascertained, the intervention system/server will transmit data via the communication interface over the network to the user device(s)/output mechanism recommending a specific software application from the collection that has demonstrated efficacy in mitigating previous group crisis states with similar characteristics. The user(s) may choose to deploy the recommended software application or select another from the software collection.

If the user or group administrator, prefers to maintain control of the conscious intervention/software application selection, the only difference is that when the intervention system transmits data to the user device(s)/output device(s), a pre-selected intervention solution/software app will not be offered. Instead, the user or administrator will receive a notification and will be prompted to make a software intervention app selection on their own. In some embodiments, the user or administrator will receive access to the entire app collection from which to make their intervention selection.

In some embodiments, the recommendation is for an app that prompts the user to act on the social environment by engaging with another in a positive way (such as providing recognition or reward). In other embodiments, the intervention could be an app that promotes knowledge sharing (such as offering key data to a team member that could benefit from it) or the intervention could directly influence any one of the six proven social environment (culture) improvers—access, choice, consistency, connection, communication, and conflict resolution.

In some embodiments, each of the processes 202, 302, 402, 502, 602, and 702 represent exemplified and non-limiting overviews of the group-crisis-detection and interventions systems and methods of the disclosed technology.

FIGS. 10A and 10B are block diagrams of PROCESS #2 outlined earlier. Process #2 can be comprised of two core processes—one of the processes is entirely automated; the other process includes some human intervention. Process #2 includes reading physiological parameters from a group of persons using on-the-body sensors and using off-the-body sensors, anonymizing and combining these on-the-body and off-the-body data to determine the group stress level from physiological-type measures. IF group stress is elevated outside of the "normal" range, the system then reads data from building sensors to: (First) determine the current state of the physical environment by reading physical-environment parameters from traditional building IoT sensors, and (second) output an (UNCONSCIOUS) automatic adjustment to the PHYSICAL ENVIRONMENT to favorably influence the group stress level by creating a more positive space for individual and group activities to be carried out. Once the on-the-body and off-the-body sensors determine a crisis state, and after the physical environment has been modified via the building sensors, then the system requests self-reported feedback from persons in the group (via the dashboard application) to ascertain the health of the SOCIAL ENVIRONMENT (CULTURE) factors and their impact on collective stress levels. The employee data request can include requests for feedback on the health of the current state of social environment and the current state of the physical environment. These two inputs combined provide a self-reported group stress measure (e.g., not biometric-based.) If the intervention system/server determines that SELF-REPORTED group stress is elevated, and if individual data is not anonymized in step two, then it can implement three distinct interventions designed to positively impact the social environment—e.g., current cultural tone of the organization—thereby reducing the group stress level. First, the system can distribute a software app optimally selected for each individual from one of the sub-collections to the users based on their user feedback. Second, individual workspace office sensors can be adjusted to the personal needs of users as reported in the feedback and, finally, users can receive the data dashboard providing robust data and visualizations of the overall organizational health and key metrics underscoring it, including their personalized data and history, in some embodiments.

In some embodiments, after the SYSTEM automatically adjusts the PHYSICAL environment, then all individuals/users in the group are automatically provided a dashboard app that indicates that group stress is elevated, and in the dashboard app is a request-for-feedback form that elicits and receives from each user their evaluation of the SOCIAL environment. If the system determines that social-environment stress is elevated, then ALL USERS RECEIVE THE SAME SOCIAL- (CULTURAL-) INTERVENTION APP BASED ON INDIVIDUAL DATA THAT HAS BEEN AGGREGATED TO A GROUP LEVEL. In other words, in this embodiment, ALL users receive the SAME intervention app designed to improve the social environment from the stress-reducing app collection. In some embodiments, for example, All users are provided with the SAME app because the self-reported individual feedback, when aggregated, indicates one primary or common social environmental driver to group stress so, a common intervention is provided to all individuals in the group. In some embodiments, where individual data is captured and not anonymized, the system provides a tailored intervention to each individual—e.g., each user receives a social environment intervention app aligned with one of six collective stress mitigating areas that is MOST relevant to the collective stress drivers impacting that user: Access, Choice, Consistency, Connection, Communication, Conflict Resolution. In some embodiments, no individual data is captured as being identifiable as coming from a particular user nor stored in a user-identifiable format, and no personalized social environmental optimizing app recommendations are made, and every user gets the same intervention to reduce group stress with a GROUP INTERVENTION to preclude the possibility of retaliation toward any one individual by anonymizing individual data. In some embodiments, each user can choose not to accept the system-provided group intervention and can then privately choose an alternative from the six social-environment-optimizing app sub-collections, or to have their personal physical workspace environment adjusted to be, for example, warmer than the group space, if that setting helps them operate optimally. In some embodiments, the foregoing process can be reversed. Specifically, after combining self-reported data to determine a set of social-environment parameters, and then combining these data to obtain self-reported group-stress-level parameters and IF group stress is present, then the system can deploy a trio of individualized social environment interventions: an appropriate app from the collections, a personalized sensory-based physical workspace adjustment, and the dashboard with data visualization, analysis, and reporting capabilities. Once the social environment has been addressed, then the system turns to address the physical environment by reading data from the building sensors (e.g., temperature, air quality, CO2 level and the like, which communicate, for example, as an internet-of-things (IoT) system) to determine a set of physical-environment parameters. In addition, the system takes a reading of the on-the-body and off-the-body physiological attribute-sensing sensors. If group stress is determined to be elevated, then the building sensors can make adjustments to improve the health and comfort of the organization's physical environment.

FIGS. 11-15 detail various sub-processes of the overarching system PROCESS #2 outlined in FIGS. 10A and 10B for identifying and intervening in group stress.

Figure 11B:
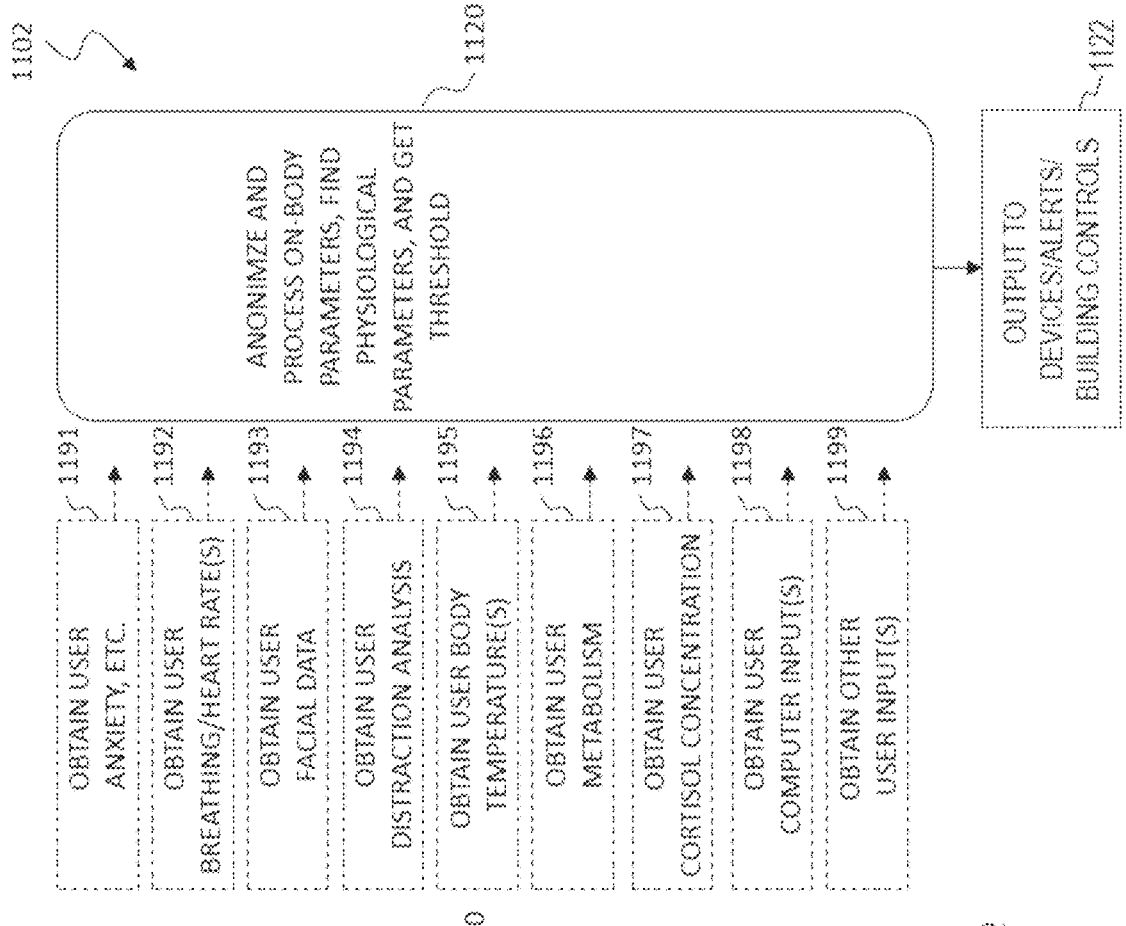
FIG. 11B is a block diagram of system that gathers data from on-body sensors for group interventions, according to some embodiments of the disclosed technology.
Figure 11A:
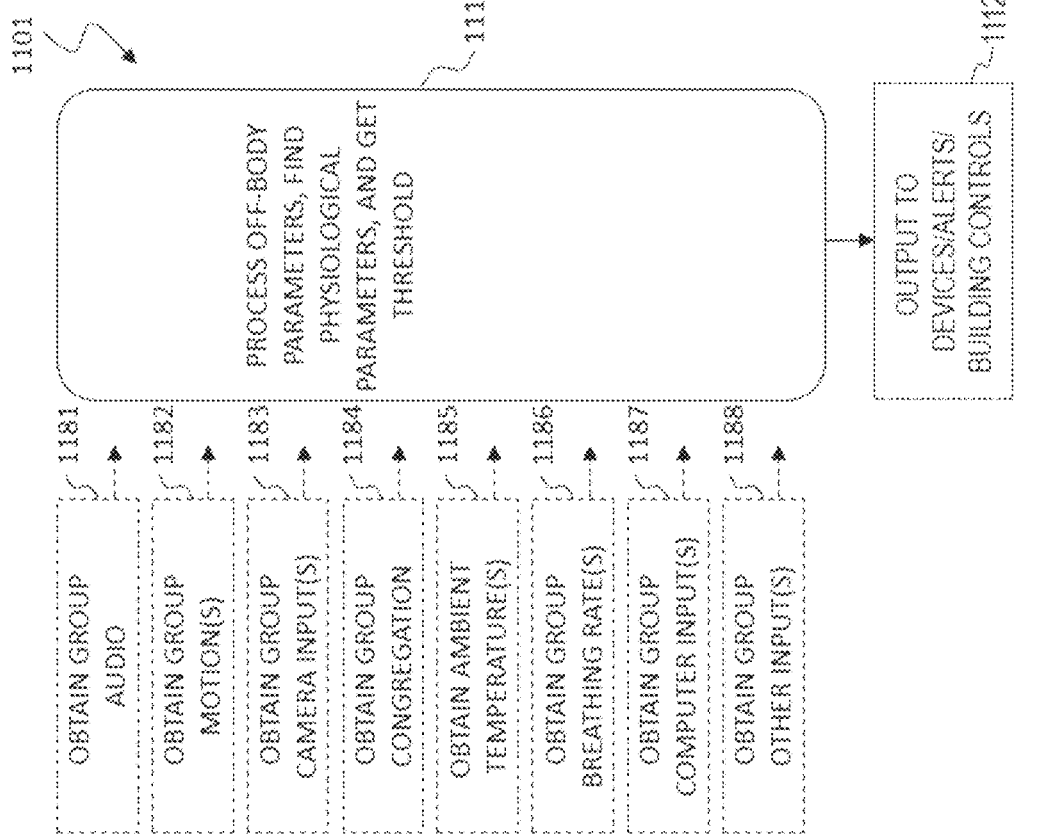
FIG. 11A is a block diagram of system that gathers data from off-body and building sensors for group interventions, according to some embodiments of the disclosed technology.

In some embodiments, such as in FIGS. 11A-B, measurements are taken to determine group stress levels. Group stress is measurable, in some embodiments, through off-body and on-body sensors.

FIG. 11A is a block diagram of system 1101 that gathers data from off-body and building sensors for group interventions, according to some embodiments of the disclosed technology. In some embodiments, system 1101 includes a plurality of off-body sensor systems such as audio sensor 1181 that obtains group audio data, motion detector 1182 that obtains group motion information, camera 1183 that obtains group image and/or motion information, congregation detector 1184 (such as an infrared sensor that images an area to determine how many persons are present and how far apart they are spaced), ambient temperature sensor 1185 that measures the room temperature, breathing rate detector 1186 (such as a camera and machine-vision system that measures the breathing of a plurality of persons, or a CO2 detector), a computer-interaction detector 1187 that measures the interactions of a group of persons with their personal computers, tablets, or smart phones, and other group-measurement devices 1188. In some embodiments, the data from the above-listed off-body devices is collected by processor 1110 and the output is used to control a plurality of user devices, alert devices, and/or building controls 1112 to achieve intervention for the group of persons.

In terms of off-body sensors as shown in FIG. 11A, in some embodiments, the sensors include one or more of the following for INPUT #1 OFF-BODY SENSORS—e.g., SURVEILLANCE:

One or more audio and/or recording devices affixed as a standalone device to an office wall or embedded into hardware such as a desktop computer, tablet, smartphone, recorder pen, recorder inside a power bank, key chain recorder, Micro Stick Voice activated recorder, flash drive recorder and other audio recording devices can be used to track increases in vocal speed of the group or increased vocal pace or volume of the group or of individuals that comprise the group to arrive at an aggregated group measure. Increases in these variables outside of the normal range are indicators of rising group/collective stress levels. The recording devices act as a passive measure—e.g., measurements are taken automatically when groups of people are within range of the audio sensor.

Motion sensors provide a way of measuring group stress levels in an environment and in some embodiments, include one or more gyroscope sensors and/or accelerometers (such as are found in most current smart phones) to track movement of a group of people. Increases in the velocity or speed of a group of people relative to a baseline speed indicate increased group stress levels. In addition to measuring speed, in some embodiments, a motion sensor is used to measure body movement (e.g., aggressive arm movement, fidgeting) and body position (e.g., forward leaning indicating flight; backward leaning indicating retreat.)

Cameras are another type of sensor for detecting increases in group movement, which indicate rising group-stress levels. Whether embedded throughout an organization's walls (or outdoor campus) or part of a larger security system or myriad other hardware devices, cameras are effective at monitoring increased levels of fidgeting (indicating nervousness) or, cameras embedded into a desktop computer or other personal hardware device can monitor and detect increased lack of concentration (e.g., distraction) via increasing, erratic eye movement (e.g., via smart glasses), head movement (i.e., continuous assessment of surroundings/lack of focus on work at hand.) Collective increases in movement against a baseline indicate increased group stress. Like audio, cameras can be included in many different types of off-body devices including clocks, flash drives, thermostats, smartphone cases and more.

In some embodiments, cameras are also used to assess individual and thus, group breathing rates. Rising breathing rates, evidenced by quicker movement up and down of the chest, is an indicator of rising stress. Using a camera affixed to the wall(s) of a room to track the movement of the chest up and down is a popular means today to monitor baby breathing while sleeping and to avoid sudden infant death syndrome.

Related to changes in movement as a group stress measure is monitoring the location—or mass movement—of people within an environment. For example, are people congregating in a specific area, or moving en masse to a certain location? Mass-movement levels indicate rising stress as groups move from one area to another perceived as safer, or more peaceful. Indoor positioning systems (IPS) are a tool/sensor for monitoring shifts in people's movement within an organization and/or on its campus or grounds. Trackers calculate speed using algorithms in the Kalman filter. In some embodiments, receivers compute speed by a combination of movement per unit time and computing the doppler shift in the pseudo range signals from the system.

In some embodiments, temperature sensors (such as long-wavelength infrared sensors or FLIR cameras) measure rising temperature as yet another way of ascertaining rising stress levels. As stress increases, the human body responds by increasing the body temperature of an individual. Collectively, as individual body temperatures rise due to stress, this causes the room temperature that includes the individuals to rise as well. Compared to a baseline, an elevated room temperature is an indicator of increased group stress.

In some embodiments, computer activity monitors provide another way of measuring group stress by monitoring content created by individuals and entered into their organizational desktop, laptop, or mobile device. Increases in anxious-indicating content such as a rise in online escapism activity, use of certain apps, and/or usage of powerful or distressful words in communications to others is an indicator of rising stress levels at the individual level. Aggregated increases of this type of activity against a baseline is an indicator of rising group stress levels. These types of activities can be monitored via content monitoring on organizational devices.

FIG. 11B is a block diagram of system 1102 that gathers data from on-body sensors for group interventions, according to some embodiments of the disclosed technology. In some embodiments, system 1102 includes a plurality of on-body sensor systems such as anxiety sensor 1191 that obtains individual person's heart rate, skin resistance or the like, breathing-rate heart-rate sensor 1192 that obtains individual person's heart- and breathing-rate information, camera 1193 that obtains individual person's facial-expression information, distraction detector 1194 (such as camera that determines a person's gaze or use of their cell phone), body temperature sensor 1195 that measures the person's temperature, metabolism sensor 1196 (such as a chemical-detection system that measures the chemicals in a person's breath, or a CO2 detector), a cortisol sensor 1197 that uses infrared light of a plurality of specific wavelengths and ratios to measure the cortisol level in a person's blood (in a manner similar to the devices that measure oxygen level), user's on-body computer devices 1198 such as smart watches and fitness sensors, and other group-measurement devices 1199. In some embodiments, the data from the above-listed off-body devices is collected by processor 1120 and the output is used to control a plurality of user devices, alert devices, and/or building controls 1122 to achieve intervention for the group of persons.

In some embodiments, the on-body sensors of FIG. 11B include many types of wearable devices that enable anxiety and stress detection. Mass-marketed wearable devices today include, in various forms of development: smart glasses, smart watches, smart clothing (e.g., shirts, socks, hats, pants, shoes), Bluetooth key trackers, accessories and jewelry (e.g., belts, rings, bracelets), ear buds, SGPS/GPRS body control, and additional "under the skin" measures that are used today predominantly in the medical arena, but which are moving increasingly to broader markets.

On-the-body sensors offer an additional level of accuracy and reliability to measuring group stress levels. In the system outlined here, individual biometric data is captured, then machine-learning algorithms are applied for biometric fusion to arrive at multimodal biometric system and group measure. In some embodiments, machine-learning algorithms to achieve this include Gaussian Mixture Models (GMMs), Artificial Neural Networks (ANNs), Fuzzy Expert Systems (FESs), Support Vector Machines (SVMs) and the like. In addition to the algorithms used for biometric fusion, the system of the disclosed technology uses other methods to process, manipulate and analyze data including clustering methods (e.g., kmeans) to investigate the structure of the data by grouping it into distinct subgroups; supervised learning (e.g., K-nearest neighbor, neural networks, and/or support vector machines) when data has been aggregated in order to maintain privacy; model learning from aggregated data (e.g., AQ algorithm approach to learning); and the like.

In some embodiments, on-the-body sensors for, such as wearables, include:

Breath Sensors: The presence of anxiety or the human fight-or-flight response increases one's metabolism, at least temporarily. Breath sensors such as gas condensers, equipped gas chromatography, mass spectrometry (GC/MS) identify increases in an individual's metabolism. Aggregated to the group level, these data are powerful indicators of group stress. In addition, air exhaled by humans contains volatile organic compounds (VOCs) that are associated with metabolism, facilitating measurement via organizational air quality sensors as well Breathing and Heart Rate Sensors: Increased breathing rate and heart rate are associated with anxiety and rising stress levels and there are numerous sensors to measure these. Today, some smartphones have the capability to process video streams from both the front- and rear-facing cameras simultaneously. This enables new monitoring methods for simultaneous estimation of heart and breathing rates using dual cameras of a smartphone. These emerging methods enable individual breathing and heart rate measurements which can be aggregated to get at a group stress measure.

Heart-Rate Sensors: Heart-rate monitoring devices in the form of wearables (e.g., watches, fitness chest straps and arm bands) are readily available today. Wearables can offer a solid array of sensors, including an altimeter, accelerometer, NFC, haptic vibration engine, Wi-Fi, a built-in microphone, and, of course, an optical heart-rate monitor. Chest-strap style monitors measure the electric wave of depolarization of the heart muscle as it contracts in the same fashion as an electrocardiogram and are highly accurate. Arm-band/leg-band monitors measure blood flow to track heart rate using the same technology as the finger clamps used in hospitals used to measure pulse and oxygen levels. Accurate systems for monitoring (group) heart rate (during exercise) have been around for many years, but to date have not been widely deployed and used. Participants wear chest strap or arm/leg band monitors which can accurately monitor heart rate and transmit it to a computer, cell phone, or iPad which is then wired or wirelessly connected to the flat screens. Heart rate monitors today are highly effective. The correlation between classic ECG derived HRV and the wearable RV ranged from very good to excellent during rest.

Body-Temperature Sensors: Body temperature increases as anxiety increases, as indicated above, and demonstrated here. Some embodiments of the disclosed technology use one of several commercially available body temperature sensors/products/wearables on the market today including a fever watch, smart bracelet, and forehead thermometers. A fingerprint thermometer of body temperature is a free smart phone android application and is the most accurate temperature rate monitor app today for any Smartphone and it does not need any external hardware. In addition, there are body temperature fitness trackers, digital ear thermometers and more. These individual measures can be aggregated to arrive at a group stress measure and compared to a baseline to confirm high group stress levels. In addition, there are many readily available room thermometers on the market today including Android apps that function as thermometers.

Skin-Temperature Sensors: Skin temperature decreases in acute stress making changes in skin temp a viable stress measure when taken at the individual level and aggregated to the group level. Today skin temperature technology readily available includes paste-on sensors, infrared cameras and next generation temporary tattoo thermometers are looking promising, among other sensor technologies. In the future, thermometers that can wirelessly broadcast their measurements will likely be prevalent.

Cognitive-Distraction Sensors: Mental distraction analysis indicating performance and/or productivity is an emerging area. High mental distraction is associated with high anxiety and stress levels. Measuring distraction has been done using ECG signals. The ECG measures the electrical activity of the heartbeat. ECG is a significant metric in driving distraction measurement. Eye movements and simple measures of performance can be used to detect distraction in real time. Potential devices for doing so include smart glasses, cameras, and adaptive in-building systems.

Cortisol-Concentration Sensors: Cortisol concentration in hair is another emerging measure of stress and anxiety. Hair cortisol concentration (HCC) increased with higher perceived stress indicating a potential measure for crisis state escalation.

Other Stress Sensors: Other factors used to measure the human affective/emotional state (i.e., increases in stress levels) include the combination of electrocardiogram and skin temperature variation plus electrodermal activity, and also electrocardiogram combined with electromyogram, skin conductance and respiration.

Figure 12:
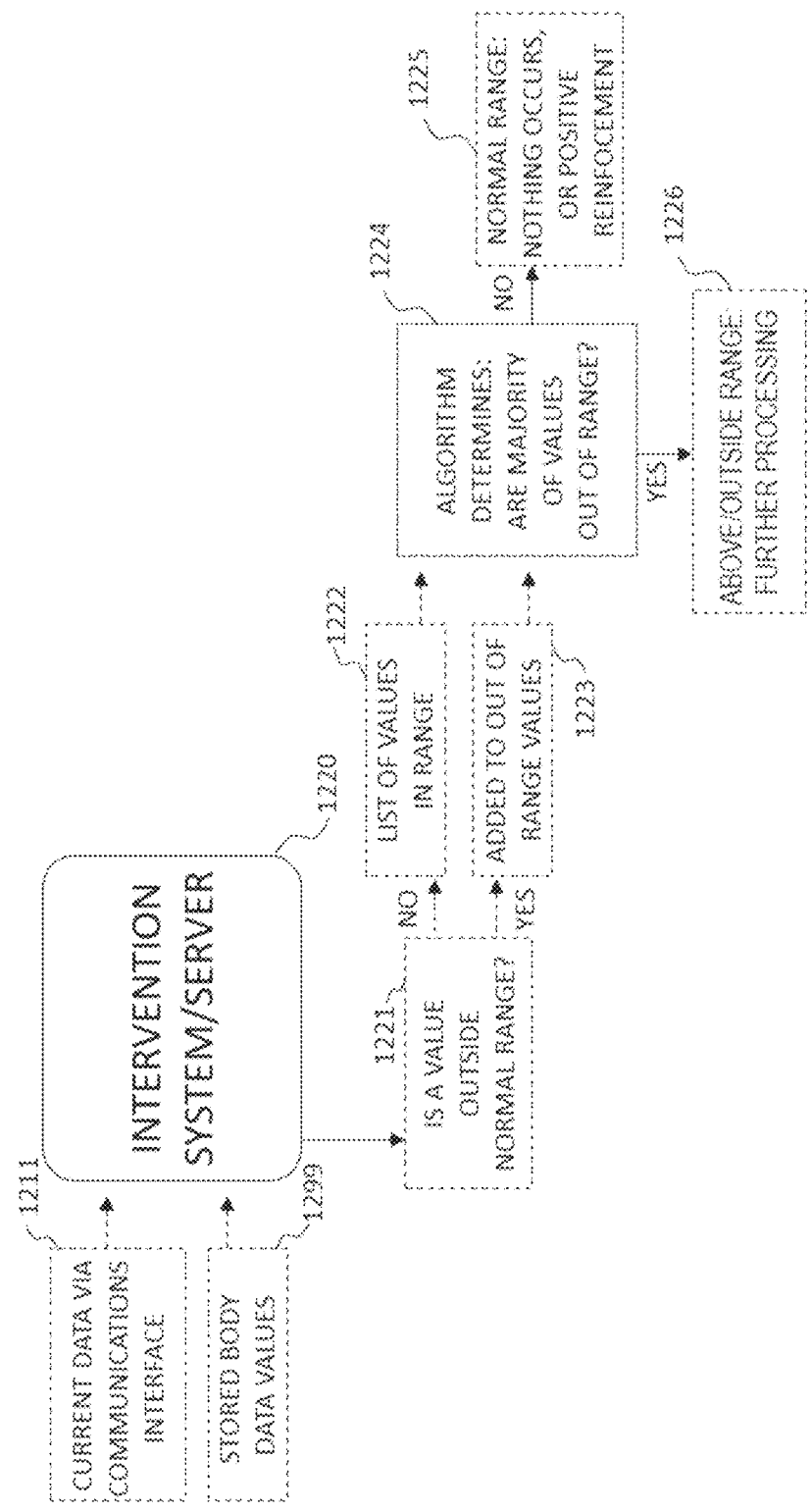
FIG. 12 is a block diagram of a group-intervention system, according to some embodiments of the disclosed technology.

FIG. 12 is a block diagram of a group-intervention system 1200, according to some embodiments of the disclosed technology. In some embodiments, group-intervention system 1200 includes a group-intervention server 1220 that obtains current data 1211 via a communications interface (e.g., wireless communication from a plurality of on-the-body and off-the-body sensors and, in some embodiments, a human-self-report made via input devices) and receives stored body data values 1299 in order to test 1221 whether one or more values are outside a normal range and if so (YES) then the value is added (block 1223) to the out-of-range list of values, and if not (NO) then the value is within the list (block 1222) of values in range of normal. At block 1224, the algorithm determines whether a majority of value (or another suitable number or percentage of values or of important values) are out of range. If not (NO) then at block 1225 the group's values are in the normal range and either nothing occurs, or optionally in some embodiments, a positive reinforcement is occasionally provided, while if a sufficient number of values are above or outside of the normal range, at block 1226 further processing is performed to determine which of one or more appropriate group interventions are to be provided.

Second, as described in reference to FIG. 12, determining group stress levels include capturing and transmitting input-sensor data, processing the data, evaluating the group stress relative to the threshold, and making a group stress determination.

Once measures have been taken from the on-body sensors and off-body sensors, as described in FIG. 11A and FIG. 11B, system 1200 of FIG. 12 determines if the group stress level is elevated, thus requiring an intervention. So, initially, the data is sent via the communications interface (which may include Wired or Wireless such as Ethernet Modbus TCP/IP, I2C, 1-Wire Communication, Controller Area Network (CAN Bus), Bluetooth Low Energy, Near Field Communication, LTE, IEEE 802.11n, IEEE 802, RS485 Modbus, Optical fiber, ARCNET, etc.) to the intervention system/server 1220 which includes the processor and memory and the intervention determiner. The intervention determiner compares the current value for each of the on-body and off-body sensors with their stored values that comprise the "Normal Range" for each sensor/measure. In some embodiments, if a current value is above the "normal range" for that measure, then that value is an indicator of group stress—e.g., outside the normal operating range for the group. After all values are compared to their baseline "normal range", the system makes a group-stress/no-group-stress determination based on how many of the sensor values are outside the normal range. If the majority of values indicate that the group is in an elevated, stressed operating state, an intervention is necessary. If only a few values are elevated, but more values are within the norm, the group is deemed as operating within their "normal range" and no intervention is implemented. In some embodiments, this determination is made by algorithm(s) that specify what variables and how many of them are out of range and by how much out of range.

In some embodiments, individual measures of stress are aggregated and converted to a group measure of stress through the use of algorithms before a group stress determination is made by the system. This process occurs by the processor in the intervention system/server. In some embodiments, the individual data is anonymized, and no identifiable individual data is captured, stored, or used by the system.

If, after this processing, group stress levels are considered inside the normal range, no intervention is actuated, in some embodiments, while in some other embodiments, a positive intervention is optionally or occasionally actuated (since occasional or random reinforcement can be more effective than continuous positive intervention).

If, after the foregoing process, collective (group) stress levels are considered outside or above the normal operating state range, then further processing occurs. In some embodiments, group data that has been aggregated from individual data is further processed, manipulated, and analyzed using algorithms including but not limited to cluster analysis, supervised learning when data has been aggregated to preserve privacy, and model learning from published aggregated data.

Figure 13:
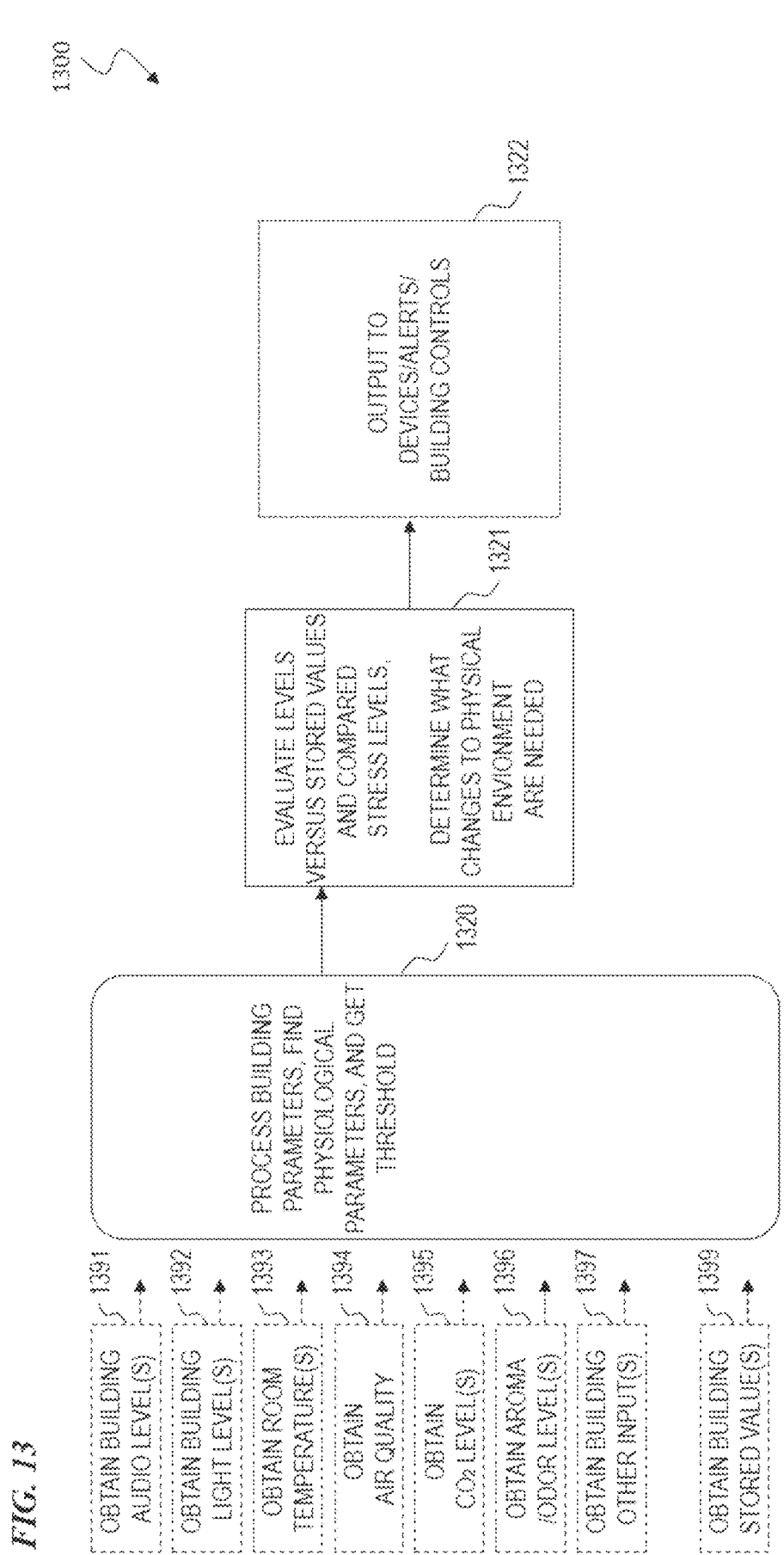
FIG. 13 is a block diagram of system that gathers data from building sensors for group interventions, according to some embodiments of the disclosed technology.

FIG. 13 is a block diagram of system 1300 (e.g., refer to FIG. 10A) that gathers data from building sensors for group interventions, according to some embodiments of the disclosed technology. In some embodiments, system 1300 includes block 1320 that elicits and receives data from block 1391 to obtain building audio levels, data from block 1392 to obtain building light levels and/or light color qualities, data from block 1393 to obtain building or room temperature levels, data from block 1394 to obtain building air-quality values, data from block 1395 to obtain building carbon-dioxide levels, data from block 1396 to obtain building aroma or odor levels, and/or data from block 1397 to obtain any other building parameters. In some embodiments, block 1320 also elicits and receives from block 1399 data regarding historic normal and crisis-state parameters. At block 1321, in some embodiments, an evaluation is performed by the computer system of the presently received values versus the stored values and determines relative stress levels and determines what changes to the physical environment are needed, and at block 1322, output signals are communicated to the relevant actuators to make the desired changes to the physical environment.

Third, as described in reference to FIG. 13, determining what physical environment intervention is needed includes receiving measures of a current state of the physical environment from the building sensors.

First, as depicted in FIG. 13 block 1320, the system instructs the plurality of building sensors that control the physical environment of the building (i.e., traditional IoT building automation sensors) to take a holistic measure of the current state of the physical environment. These building measures (input sensors) vary per embodiment and include sensors such as—Decibel meter/microphone—measures sound level, Photometer—measures light intensity for lighting control, Thermometer—measures room temperature, VOC (volatile organic compounds) sensor—measures air quality, Carbon dioxide meter measures air quality, and Olfactometer—measures aroma/odor dilution.

In some embodiments, the building sensors are used to measure the physical environment only, while other building sensors are optionally also used to measure a group-stress indicator and the building's physical environment.

Second, as depicted in FIG. 13 block 1321, the current values of these physical-environment measures are compared to stored values and compared to the current and historical group stress values to determine the adjustments needed to the physical environment to facilitate the de-escalation of the group stress level. In some embodiments, the system 1300 determines automatically what changes to the PHYSICAL ENVIRONMENT are needed. In other words, the system 1300 determines what modifications to the building sensors need to be made to reduce group-stress levels within the parameters of the normal operating state. In some embodiments, artificial intelligence and/or machine learning are used in the process, providing continuous feedback by which the system initially "learns" to determine appropriate group interventions, and then later continuously improves itself over time.

EXAMPLES OF OUTPUT DEVICES/ALERTS/BUILDING CONTROLS INCLUDE: Dimmer—fan speed, light intensity, Infrared output—send infrared controls/signals (control devices mimicking their remote controls), Multi-color LED—shine light in any color or intensity (room lighting plant growing), Sound—playing sounds (beeps, voice announcement), Switch—switch on an electric device on or off (heater, fan, light), and Valve—open/close gradually (control flow of liquids, gases).

Factors for improving physical environments that mitigate human stress levels and improve well-being can include but are not limited to clutter, crowds and loud noises, green space in relation to mood and mental health, aquariums and fish tanks, aromatherapy and aroma inhalation, lighting, and aesthetics such as natural textures and patterns.

Third, as depicted in block 1322, the system 1300 outputs to device in the building alerts and/or other changes that need to be made to the physical environment.

Figure 14:
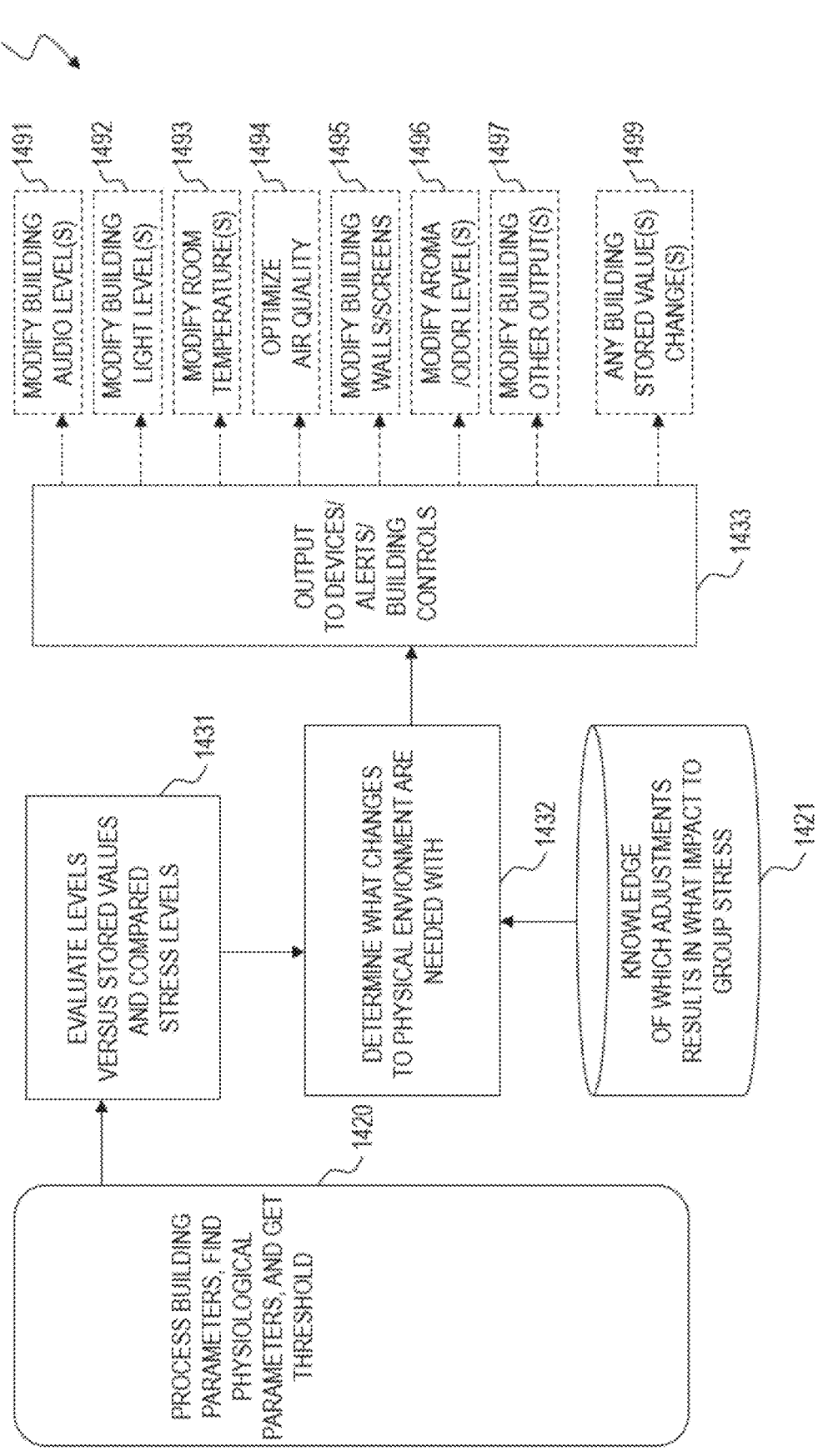
FIG. 14 is a block diagram of an evaluation and output system that processes data from on-body, off-body, and building sensors for outputting group interventions, according to some embodiments of the disclosed technology.

FIG. 14 is a block diagram of an evaluation and output system 1400 that processes data from on-body, off-body, and building sensors for outputting group interventions to improve the physical environment, according to some embodiments of the disclosed technology (e.g., refer to FIG. 10A.) In some embodiments, system 1400 includes block 1420 that elicits, receives and processes data from system 1101, from system 1102 of FIG. 11B, from system 1200, from system 1300 and from system 1500, data obtained from self-reports from users, in some embodiments, and at block 1431, evaluates the group-stress levels versus stored values for normal and stress situations, at block 1432 determines what changes to the physical environment are needed with (at block 1421) knowledge stored as to which adjustments resulted in what impact to group stress in the past) and at block 1433, outputs signals communicated to output devices 1491-1497, and optionally also stores (at block 1499) the current output data to the stored database of output changes and the results obtained from those changes. Block 1491 represents a modification to the building audio output (such as white or pink noise, music or other audio signals, block 1492 represents a modification to the building light levels or the color of the light in the environment, block 1493 represents a modification to the building or room temperature, block 1494 represents a modification to the building air quality, block 1495 represents a modification to the building walls or screens including moving walls or screens, block 1496 represents a modification to the building aroma or odor levels, block 1497 represents a modification to other building actuators or parameters.

FIG. 15 is a block diagram of system 1500 (e.g., refer to FIG. 10B) that gathers self-reported data from individual users for group interventions, according to some embodiments of the disclosed technology. In some embodiments, system 1500 includes block 1510 to gather data, such as, at block 1511, eliciting and receiving from individuals comprising the group (e.g., employees) a self-reported rating of two or more levels of the environment—for example, at block 1512 a rating of the physical environment and at block 1513 a rating of the social environment (culture). At block 1514, a rating of the overall or company-level physical environment and the users immediate and specific workspace is determined by the system 1510. At block 1515, a rating of the social environment (culture) on six variables that mitigate collective stress and align with themed app sub-collections (e.g., transparency, choice, consistency, connection, communication, and conflict resolution) is determined by the system 1510. In some embodiments, the system anonymizes individual ratings to protect users from subsequent retaliation. As results, in some embodiments, system 1500 provides at block 1521, a message from the system to individuals in the group a recommendation to engage with at least one app to download and execute on the users personal electronic device (such as a smart phone), at blocks 1531 and 1541, one or more dashboard reports from the system to the individuals in the group with anonymized and combined scores or ratings, and at block 1551, the system outputs and communicates signals to modify the overall physical environment (e.g., of a company) and/or the individual workplace, and optionally sends a notification to the company administration for any needed changes that are not immediately available for the system to automatically modify. In some embodiments, the system of the disclosed technology stores just enough anonymized information to allow a user to modify the group intervention for that user, but the system does not make that information available to other users in order to preserve anonymity to the extent possible. In some embodiments, the system anonymizes and combines the individual data to provide every user in the group with the SAME GROUP intervention, versus an individualized intervention, to reduce collective (group) stress levels.

As described in reference to FIG. 15, system outputs #1 can include changes to different or multiple building sensors to improve the physical environment. Via ongoing learning, the system calibrates to each group and each physical and social environment—no one group presents collective stress in the same manner as another group nor does any one group react the same to the same interventions. Interventions to mitigate collective stress change over time for any one particular group, as circumstances and individual members in that group change.

In some embodiments, if group stress is elevated, some groups in some environments, may respond to a downward adjustment to the building temperature as a means of reducing group stress. In other environments, poor air quality may be a known stress driver so, the system adjusts windows open for fresh air. Elsewhere, more natural light may be needed so a photometer makes the appropriate adjustment to increase lighting or it instructs the sky window to open to allow in natural sunlight. In other environments, crowding may be a major stress driver, so the system raises the ceilings or opens movable walls that are closed. Yet another environment may benefit from images of the natural world displayed on a screen against a wall if a motion sensor were to sense mass agitation/hyper-stress. There are myriad physical interventions made possible in the built environment via current IoT technologies (and even more in the future) that are known to directly, and indirectly, impact stress levels, some of which are indicated here. In some embodiments, to determine the physical environment intervention required to reduce group stress levels, the system evaluates:

Current Building (Physical) Environment Values—what are the building values currently?—e.g., is the temperature too high, higher than the range known to support the normal group operating state?

Optimal Historical Values—prior knowledge, storage, and determination of optimal physical environment settings. Because the system is a learning system, optimal values are continually reset with more data and more learning over time.

Group Stress Drivers and Mitigators—knowledge of what sensors and what sensor adjustments results in what impact to group stress—which is, again, a byproduct of system machine learning over time.

As described in reference to FIG. 15, additional system output #2 can include alerts to group members that the group stress level is elevated. Feedback can also be obtained from the group members to systematically make adjustments to the social and physical environment of the group. This can include individual interventions, group interventions, or a combination of both in some embodiments.

If group-stress levels are determined to be above the normal range, then the social environment also needs to be modified. In addition, individual workspaces need to be evaluated by each employee and modified to his/her personal needs, if necessary, to improve their personal PHYSICAL ENVIRONMENT. In some embodiments, individuals have control of their workspace environment including variables such as temperature, lighting, desk height, aroma, and/or sound.

In some embodiments, as described herein, the disclosed technology can provide for automatic intervention when a member of the group receives an exceptionally high level of positive or negative feedback from other group members. Too much negative feedback can indicate that the member is struggling in the environment and/or at work, which can cause the employee to be in a state of extreme stress and can lead to extreme behaviors driven by, for example, fear of retribution or job loss. Significant positive feedback can indicate exceptional performance that may or may not get recognized via traditional organizational processes. The automatic intervention can use facts and data as input to assist an organization in determining which employees may need assistance to improve performance and/or may need some power or control taken away due to the negative impact of their behaviors on others. Similarly, the automatic intervention can identify high performers who may not be recognized as such due to subjective, human-led organizational processes. Thus, the disclosed technology can assist in taking away some of the inequities driven by subjective evaluations of employees that may be made by bosses and others who, as all humans are, influenced by bias and subjectivity.

In some embodiments, the intervention system outputs directed at individuals or groups includes the following:

First, still referring to FIG. 15, in 1511, employees are sent the system dashboard software which includes a feedback mechanism for inputting ratings on two levels:

SOCIAL ENVIRONMENT 1513—individuals in the group are asked to rate the current state of the organizational culture on the six variables proven-effective in reducing collective stress 1515:

ACCESS/TRANSPARENCY (sharing information, access to information and tools to do the job), CHOICE (strategy/voice in the solution, balance, self-selected training and development), CONSISTENCY (consistent policy and procedures, same treatment for all, intervention of bad behavior), CONNECTION (service to each other, celebrate, build comradery/friendship), COMMUNICATION (recognition, organizational data/information/strategy and plans, evaluation—top down and bottoms up,) and CONFLICT RESOLUTION (skill building, shift onus from supervisor to third parties, or the like).

PHYSICAL ENVIRONMENT 1512—individuals in the group are asked to rate the current state of the physical environment overall (e.g., the broad built environment and surroundings) and their specific workspace on multiple variables 1514.

Second, individuals in the group are sent a SOCIAL ENVIRONMENT intervention app 1521 to one or more personal devices of their choosing (e.g., laptop, desktop computer, smart phone.) The themed app sub-collections are aligned with the six proven social environment intervention areas. In some embodiments, apps are presented to individuals based on their self-reported ratings. In some embodiments, the system anonymizes and combines the individual data to provide every user in the group with the SAME GROUP INTERVENTION to reduce collective (group) stress levels and preclude subsequent retaliation directed at specific individuals.

Third, all individual scores are combined and then reported to all group members and administrators via the system dashboard in 1531. The dashboard presents an overall organizational health score, a social environment (culture) score, a physical environment score, a group stress sensor score (on-the-body and off-the-body), and detail for each of the input variables. In some embodiments, employees and administrators have transparency to the group/aggregated data, but not individual employee data. In some embodiments, individuals can review and track their personalized data but are excluded from access to others' data. In some embodiments, all individual data is anonymized and captured for group stress assessment only—e.g., not stored, accessible or retrievable in any way.

Fourth, based on individual feedback pertaining to the physical environment, in some embodiments, the system makes automatic changes to each individuals' workspace to align with their feedback in 1551. For example, if an individual reports excessive cold, the system will instruct a thermometer to raise the heat level in their area or a switch will be commanded to turn on a space heater. In some embodiments, the system notifies administrators about new and/or additional physical environment issues or opportunities expressed by individuals in the group so that they may be considered in the future to optimize group operating states. In some embodiments, all individual data is anonymized and captured for group stress assessment only—i.e., no personalized workspace adjustments are made by the system; instead, a common group intervention is applied. In some embodiments, individuals control their workspace environment entirely. In some embodiments, individuals can override group physical interventions that impact their work area.

Figure 16A:
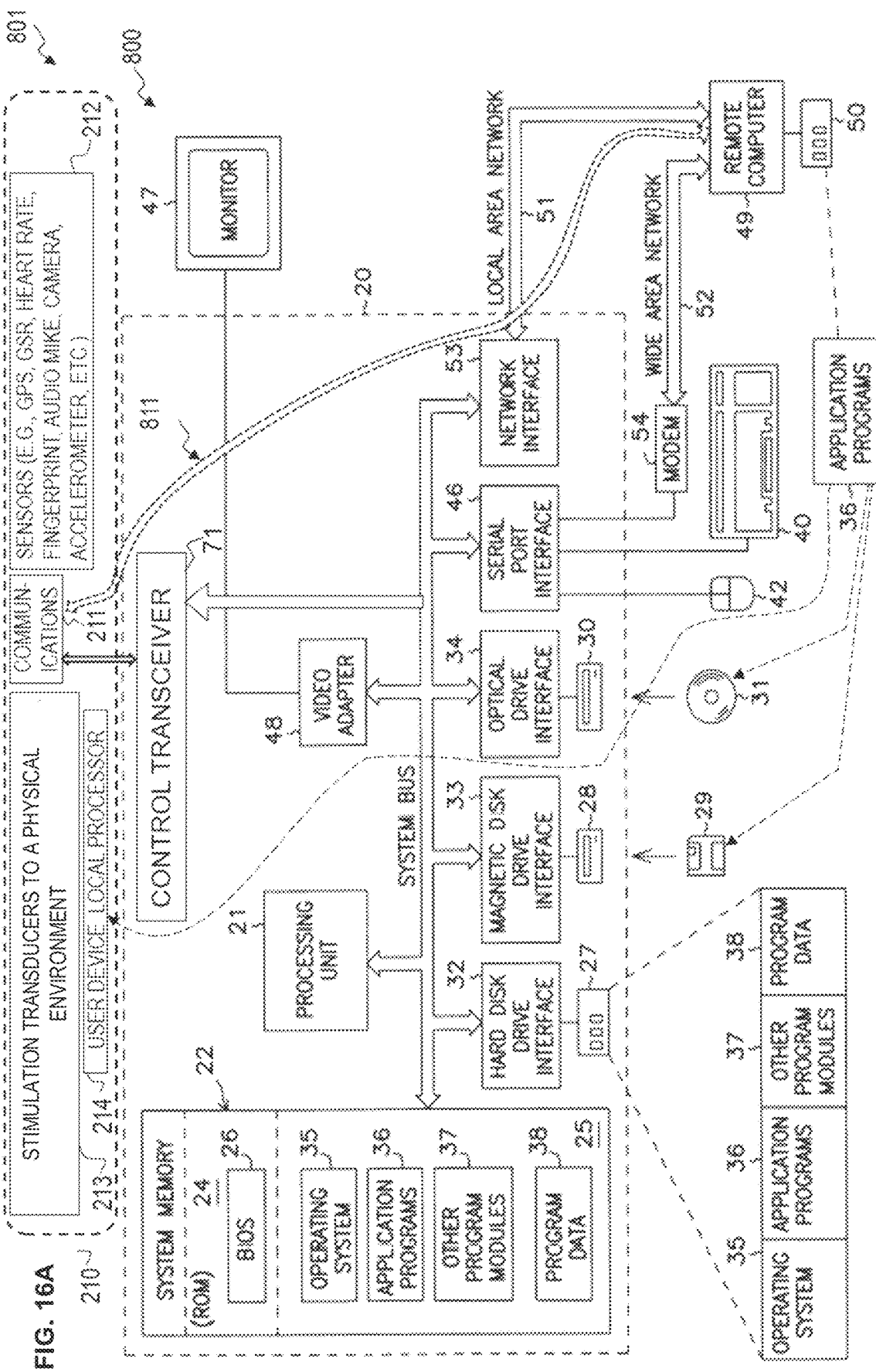
FIG. 16A is a block diagram of an exemplary system for implementing the present invention that includes a conventional general-purpose computing system and one or more user device(s), according to some embodiments of the disclosed technology.

FIG. 16A is a block diagram of an exemplary system 801 for implementing the disclosed technology that includes a conventional general-purpose computing system 800 and one or more user device(s) 210. In some embodiments, conventional general-purpose computing system 800 includes a conventional personal computer 20, including a processing unit 21, a system memory 22, and a system bus 23 that couples various system components including the system memory to the processing unit 21. The system bus 23 may be any of several types of bus structures including a memory bus or memory controller, a peripheral bus, and a local bus using any of a variety of bus architectures. The system memory includes read only memory (ROM) 24 and random-access memory (RAM) 25. A basic input/output system (BIOS) 26, containing the basic routines that help to transfer information between elements within the personal computer 20, such as during start-up, is stored in ROM 24. The personal computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer readable instructions, data structures, program modules and other data for the personal computer 20. Although the exemplary environment described herein employs a hard disk, a removable magnetic disk 29, and a removable optical disk 31, it will be appreciated by those skilled in the art that other types of computer readable media which can store data that is accessible by a computer, such as magnetic cassettes, flash memory cards, digital video disks, Bernoulli cartridges, random access memories, read only memories, and the like may also be used in the exemplary operating environment.

A number of program modules may be stored on the hard disk, magnetic disk 29, optical disk 31, ROM 24 or RAM 25, including an operating system 35, one or more applications programs 36, other program modules 37, and program data 38. A user may enter commands and information into the personal computer 20 through input-devices such as a keyboard 40 and a pointing device 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a parallel port, game port or a universal serial bus (USB). A monitor 47 or other type of display device is also connected to the system bus 23 via an interface, such as a video adapter 48. In addition to the monitor, personal computers typically include other peripheral output devices, not shown, such as speakers and printers.

The personal computer 20 may operate in a networked environment using logical connections to one or more remote computers, such as a remote computer 49. The remote computer 49 may be another personal computer, a server, a router, a network PC, a peer device or other common network node, and typically includes many or all of the elements described above relative to the personal computer 20, although only a memory storage device 50 has been illustrated in FIG. 16A. The logical connections depicted in FIG. 16A include a local area network (LAN) 51 and a wide area network (WAN) 52. Such networking environments are commonplace in offices, enterprise-wide computer networks, intranets and the Internet.

When used in a LAN networking environment, the personal computer 20 is connected to the local network 51 through a network interface or adapter 53. When used in a WAN networking environment, the person computer 20 typically includes a modem 54 or other means for establishing wireless and/or wired communications over the WAN 52. The modem 54, which may be internal or external, is connected to the system bus 23 via the serial port interface 46. In a networked environment, program modules depicted relative to the personal computer 20, or portions thereof, may be stored in the remote memory storage device. It will be appreciated that the network connections shown are exemplary and other means of establishing a communications link between the computers may be used.

In some embodiments, each user device 210 includes a communications interface 211 (such as Bluetooth®, Wi-Fi and/or cellular telephony or the like), and a plurality of sensors 212 (such as global-positioning system (GPS) sensors for location, spatial orientation, speed, etc., galvanic skin response (GSR) sensors, heart-rate sensors, fingerprint sensors (for device activation, authorization or locking), audio microphone(s) for voice and ambient noise evaluations, camera(s) for analysis of hand gestures, posture, facial expressions, and the like, accelerometers, gyroscopes and/or magnetometers for determining orientation, speed, acceleration and the like, and other sensors as may be needed to help determine a group's collective state. In some embodiments, each user device 210 also includes a local processor and its database and programs that are used to determine the user's or group's state and, based on that determination, send one or more commands to intervention actuators 213, which in various embodiments herein include one or more of the following: touch stimulation, scent emitters for sense-of-smell stimulation, salt, sweetness, or citric-acid sources or the like for taste stimulation, and/or electrodes and micro-current drivers for electrical stimulation or other stimulation to the user in the related disclosed technology; or transducers to modify a physical environment disclosed herein. In some embodiments, the data from the sensors 212 and the data to the interventional actuators 213 are streamed from and among apps or other software modules executing in individual parts of user device 210 and/or server 220.

In some embodiments, each of the intervention actuators 213 is programmable to provide a range of stimulation types and stimulation intensities in order to provide interventions that are either unconscious (imperceptible to the group) or conscious (perceptible to the group).

Figure 16B:
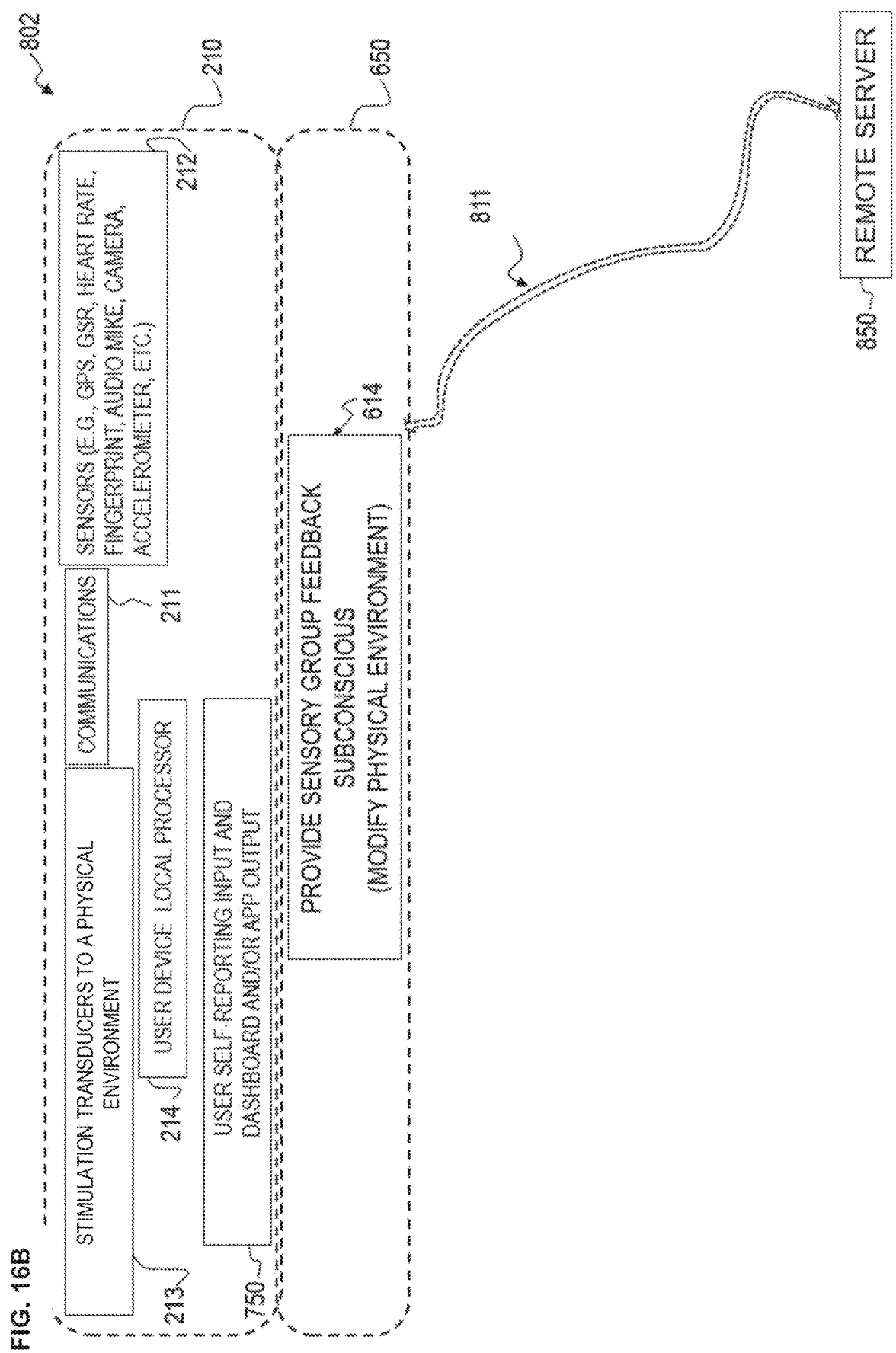
FIG. 16B is a block diagram of a simplified exemplary system for implementing the present invention that, in contrast to system of FIG. 16A, includes much or all of the functionality of conventional general-purpose computing system instead implemented in a smart-phone system of wearable devices in one or more user device system(s), according to some embodiments of the disclosed technology.

FIG. 16B is a block diagram of a simplified exemplary system 802 for implementing the disclosed technology that, in contrast to system 801 of FIG. 16A, includes much or all of the functionality of conventional general-purpose computing system 800 instead implemented in a smart-phone system of wearable devices in one or more user device system(s) 210, according to some embodiments of the disclosed technology. In some embodiments, user-device local processor 214 includes all of the parts and/or functionality of intervention server 220 and database 221.

For example, as depicted in FIG. 16B, the user device system(s) 210 can include stimulation transducers to a physical environment 213, a communication interface 211, one or more sensors 212, local processor(s) 214, and a user self-reporting input and dashboard and/or application output 750. The unconscious intervention system 650 (e.g., refer to FIG. 8) can also have module 614 configured to provide group feedback, as described herein. One or more of the systems 210 and 650 can be in wired and/or wireless communication 811 with a remote server 850. The remote server 850 can be an intervention system as described throughout this disclosure.

Figure 17B:
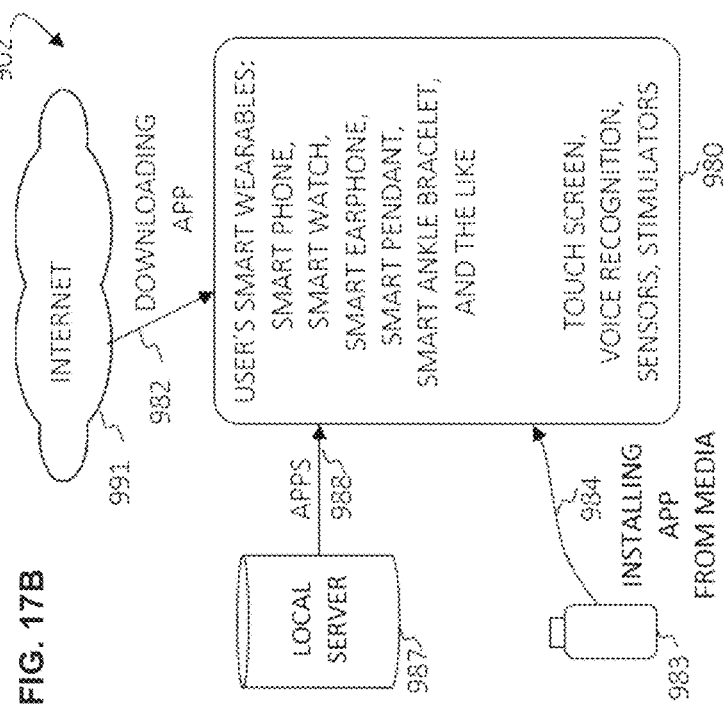
FIG. 17B is a block diagram of a process for dispensing programs into a personal computer or similar information-processing device.
Figure 17A:
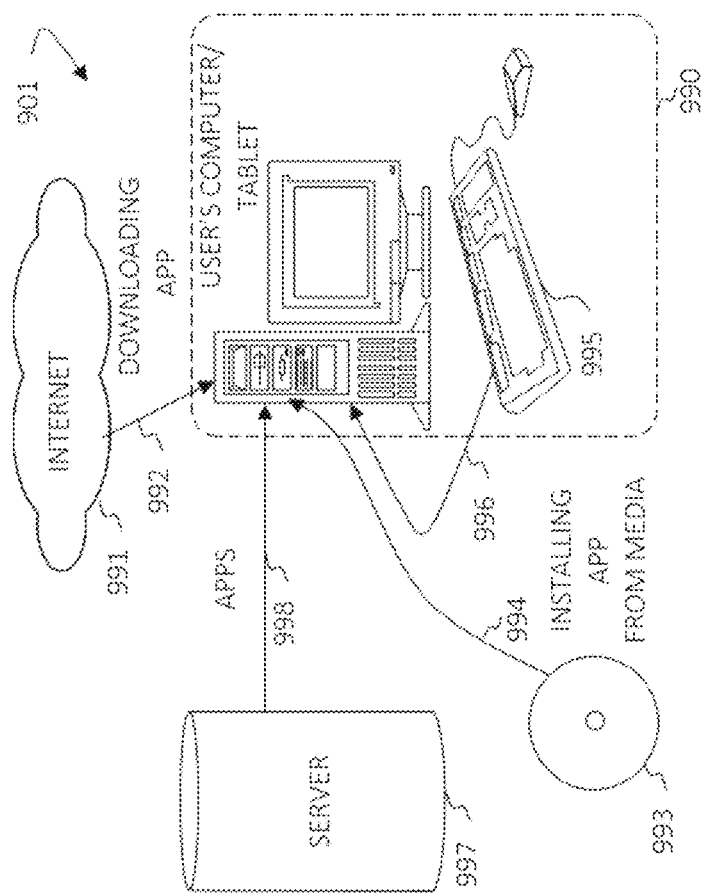
FIG. 17A is a block diagram of a process for dispensing programs into a personal computer or similar information-processing device, for example, a new user device being purchased by its initial user.

FIG. 17A is a block diagram of a process 901 for dispensing programs into a personal computer 990 or similar information-processing device, for example, a new user device being purchased by its initial user. Conventional methods for dispensing software into a personal computer 990 occasionally include downloading 992 of software from a network 991. For example, network 991 could be a manufacturer's internal network used to preload programs and audio-visual interventions (software) into a user device being assembled. Further, software. videos and music are commonly available for purchase (or even for free, in some cases) and immediate download from the internet 991 via a process of "downloading." Further, some software is available as downloads from proprietary wireless networks 991 (such a corporation's internal network), or external networks such as those operated by cell-phone carriers. In some embodiments of the disclosed technology, loading methods also include uploading, media-installing 994 of software from physical media 993 (e.g., USB FLASH memory, and the like), sometimes also requiring substantial amounts of manual input 996 from a user via an interactive input device 995 (such as a manual keyboard). It takes a considerable amount of the user's time and mental energy (the drain on the user from the concentration needed to perform the various unfamiliar tasks, as well as the boredom from waiting for the process to complete), as well as power from the electrical grid needed to download and install a large selection of software from the internet 991, or to install software from media 993 and/or input device 995.

In contrast, as shown in FIG. 17B, one aspect of the set up process 902 of the disclosed technology provides loading 988 of software and/or training data and personal data, wherein training and personal data are derived from the user's past activities and kept on a user's storage medium 987 that is operatively coupled to computer 980 (e.g., in some embodiments, the user device 210 of FIG. 2), in order that the user's personal data are loaded onto the user's device 980. In some embodiments, the crisis detection and intervention programs and more-universal human and group data and thresholds are downloaded 982 from server(s) on the internet 991. In some embodiments, the disclosed technology includes a non-transient computer-readable medium having instructions stored thereon that, when executed by a computer that includes at least one database, cause the computer to perform any one or more of the methods herein.

FIG. 18 is a table 1701 that indicates examples of how group stress is measurable, according to some embodiments of the disclosed technology. For example, one or more tools/sensors can be used on-the-body or off-the-body to measure different conditions of the person. Traditional surveillance tools (e.g., audio, camera(s)) can be used off-the-body (e.g., placed in a physical environment). These tools can include but are not limited to a recorded power bank or a flash drive. Using such tools, group vocal speed, pace, and volume can be measured and analyzed. For example, an increase in vocal speed, pace, and/or volume can indicate vocal distress, which is indicative of anxiety or other forms of stress.

IPS and/or GPS cameras can also be used off-the-body to measure peoples' walking speed and movement to different specific locations. These tools can be portable (e.g., worn by a person) or stationary (e.g., placed throughout a building or office space). A faster walking speed can indicate anxiety or stress. Specific locations can be identified as "safe" zones. If a person moves towards a safe zone, it can indicate that the person is trying to escape a stressful or toxic environment/ situation.

Body temperature sensors can be used on-the-body via wearable devices (e.g., smartwatch). Increases in body temperature can indicate that a person is getting anxious or stressed. Room temperature sensors can also be used off-the-body (e.g., placed throughout the office space) via thermostats. Room temperature and body temperature information can be combined to determine group stress. For example, an aggregate group body temperature can have an impact on an overall room temperature. The higher individual body temperatures, the higher the overall room temperature, which can indicate that the group is experiencing some form of stress.

Heart rate monitoring sensors can also be used on-the-body via wearable devices. Individual heart rates can be analyzed and aggregated to determine overall increases in heart rates and strengths of heart beats. Overall increased heart rates and heartbeat strengths can indicate that the group is experiencing some form of stress.

Figure 19:
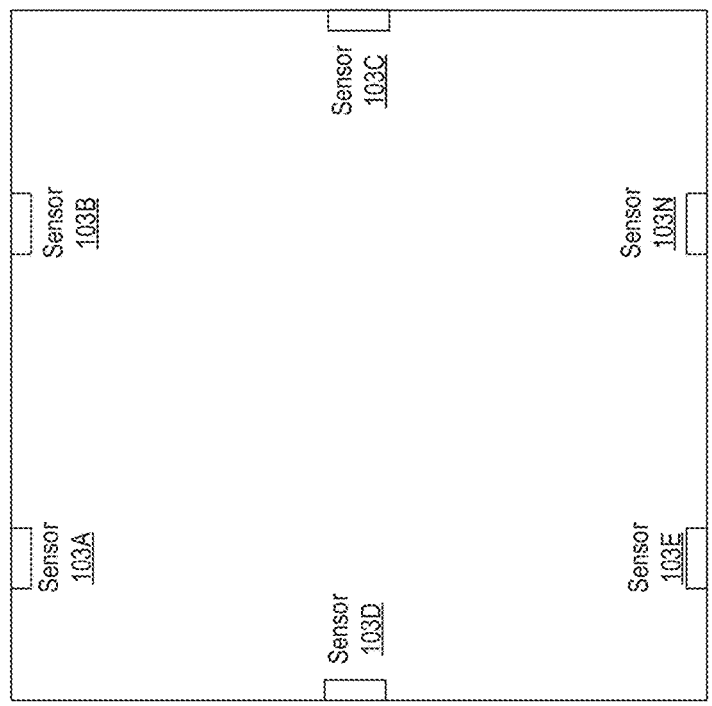
FIG. 19 is a physical environment that illustrates types of physical environment sensors used to obtain parameters of the physical environment affecting the collective stress of a group of persons, according to some embodiments of the disclosed technology.

FIG. 19 is a physical environment 1702 that illustrates types of physical environment sensors used to obtain (1) parameters of the physical environment affecting a group of persons and (2) off-the-body sensors used to assess group stress physiological parameters, according to some embodiments of the disclosed technology. Sensors 103A-N can be used to measure physical status of the environment (e.g., building). Sensors 103A-N can also be used, additionally or alternatively, for measuring group stress. In some embodiments, sensors 103A-N may not be used to assess the group operating/stress state; they can be used to measure the current status of the building physical environment. The sensors 103A-N can take a read on the current physical environment 1702. If the group operating state is determined to be above the threshold (e.g., a physical environment intervention is necessary), then the system can influence the physical environment by adjusting the physical environment sensors illustrated to bring the group stress level within the normal operating state range. A current state of the physical environment 1702 can be the baseline to modify. Furthermore, the sensors 103A-N can collaborate/communicate with one or more group stress sensors described throughout this disclosure (e.g., off-the-body and on-the-body sensors) to identify optional physical environment settings that are aligned with the normal group stress levels (e.g., normal operating state range).

FIG. 20A is a table 1703 that lists types of physical environment sensors used to obtain parameters of the physical environment affecting the collective stress level of a group of persons, according to some embodiments of the disclosed technology. For example, decibel meters and/or microphones can measure voice sound levels. Photometers can measure light intensity for a lighting control. Thermometers can measure room temperature. VOC sensors can measure air quality. Carbon dioxide meters can also measure air quality. Olfactometers can measure aroma and/or odor dilutions. One or more of these sensors can be used in combination for monitoring conditions within the physical environment. One or more other sensors not listed in the table 1703 can also be used to measure conditions in the physical environment.

FIG. 20B is a table 1704 that lists types of remote (off-the-body or over-the-skin) sensors used to obtain group-stress parameters of the group of persons affecting that group, according to some embodiments of the disclosed technology. In some embodiments, these sensors are sensors designed to measure and identify escalated group stress levels. In some embodiments, they may serve the twin purposes of ascertaining stress and evaluating the current status of the physical environment. In some embodiments, these sensors along with the on-the-body sensors described below are designed to measure overall the group operating state together.

Exemplary sensors listed in the table 1704 include audio and/or recording devices, which measure group vocal speed, pace, and/or volume. Computers and/or smartphone activity monitoring and recovery stick sensors can measure aggregated increases in anxious-indicating content (e.g., visiting non-work-related websites, checking personal emails, escapism, distress texts). Cameras can measure increases in movement (e.g., fidgeting, nervousness) and increases in lack of concentration (e.g., distraction). Motion sensors (e.g., gyroscope accelerometer) can be used to measure changes in velocity or speed. Room temperature sensors can be used to measure increases in body temperatures that raise the overall room temperature. Indoor positioning systems (IPS) can also be used to measure location and/or movement of people and objects within the physical environment.

FIG. 20C is a table 1705 that lists types of on-the-body (on-the-skin) sensors used to obtain individual physiological parameters of the persons in a group contributing to the collective stress level of that group, according to some embodiments of the disclosed technology. In some embodiments, there is a distinction between these on-the-body sensors which are on-the-person versus the remote or off-the-body sensors which are largely traditional surveillance and in-the-building devices. In some embodiments, the on-the-body sensors are largely taking individual biometric measures that are subsequently anonymized and aggregated to a group measure. The disclosed technology here is taking individual measures to get at group stress/collective stress by aggregating the individual data. The disclosed technology herein is focused on addressing "collective stress" as a phenomenon that exists on its own. Collective stress drives collective dysfunctional behaviors, just like individual stress drives individuals to behave dysfunctionally. Thus, the stress that is detected and to which the intervention is directed is referring to the actual phenomenon of group stress, also known as "collective stress." In some embodiments, machine-learning (ML) algorithms are applied for biometric fusion to arrive at a multimodal biometric system and group measurement. In some embodiments, machine learning algorithms include, e.g., Gaussian Mixture Models (GMMs), Artificial Neural Networks (ANNs), Fuzzy Expert Systems (FESs), and Support Vector Machines (SVMs.).

Exemplary on-the-body sensors, as depicted in table 1705, include but are not limited to breath sensors (e.g., gas condenser, mass spectrometry—GC/MS) that measure increases in metabolism. Body temperature sensors (e.g., fever watch, smart bracelet, ear or forehead thermometers) can measure increases in body temperature. Skin temperature sensors (e.g., paste-on sensors, infrared cameras, tattoo thermometers) can measure decreases in skin temperature. Heart rate monitors (e.g., FITBIT, APPLE watch, chest strap, arm/leg band, smartwatch) can measure electric waves of depolarization of the heart muscle (e.g., via the chest strap) and blood flow (e.g., via the arm/leg and). Eye movement sensors (e.g., smart glasses, cameras) can measure mental distraction (e.g., performance, productivity). Mass spectrometry (MS) and/or chemoluminiscent immunoassay analyzers can be used to measure cortisol concentration in a person's hair (e.g., proxy to total HPA activity in the preceding months). Moreover, electrocardiogram sensors can be used to measure human affective and/or emotional states. One or more other under the skin sensors not depicted in table 1705 can be used to achieve similar results as described throughout this disclosure.

Figure 20D:
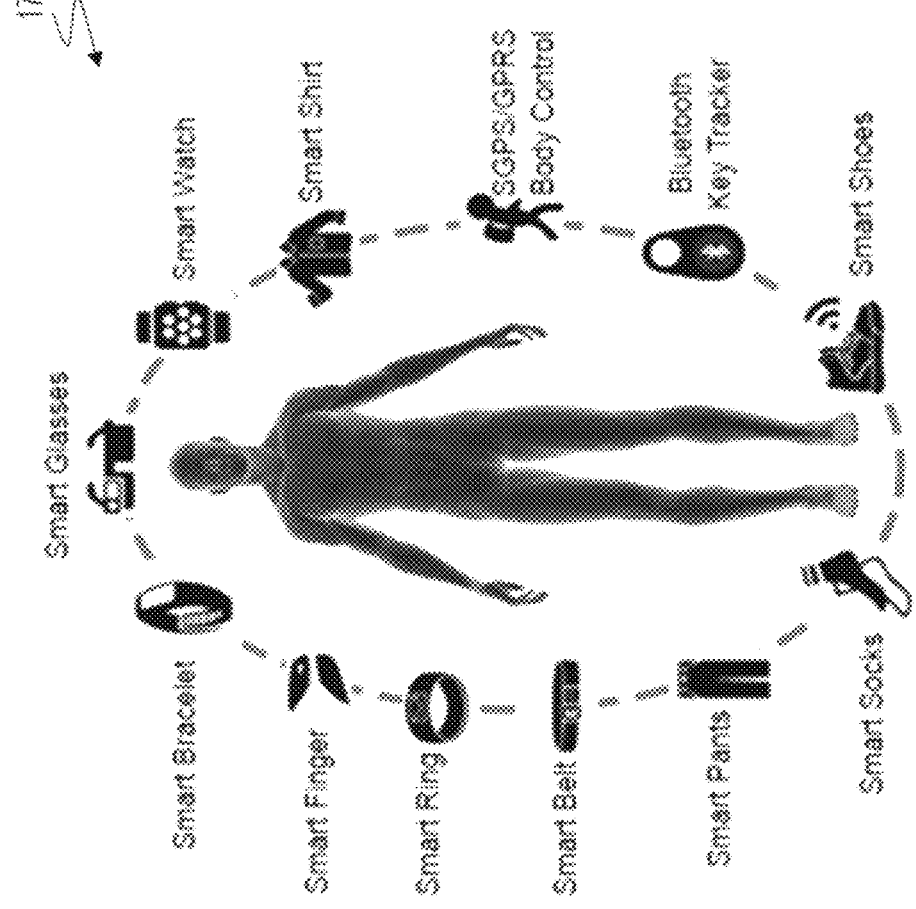
FIG. 20D is a graphical presentation that illustrates types of on-the-body (on-the-skin) sensors used to obtain individual physiological parameters of the persons in a group affecting that group, according to some embodiments of the disclosed technology.

FIG. 20D is a graphical presentation 1706 that illustrates types of on-the-body (on-the-skin) sensors used to obtain individual physiological parameters of the persons in a group affecting the collective-stress level of that group, according to some embodiments of the disclosed technology. Body temperature increases with anxiety. Consequently, increasing body temperatures increase the overall room temperature, both of which can be measured via different means. Group heart rate is another stress indicator that can be obtained by aggregating individual measures. Accurate systems for monitoring (group) heart rate during exercise have been around for many years, but to date have not been widely deployed and used.

There are a variety of wearable technologies that enable anxiety and stress detection. For example, these can include smart glasses, smartwatch, smart shirt, or other clothes, SGPS/GPRS body controls, BLUETOOTH key trackers, smart shoes, smart socks, smart pants, smart belt, smart ring, smart finger, and/or smart bracelets. On-the-body (on-the-skin) sensors offer an additional level of accuracy and reliability if employees consent to wear a company-provided device. As described herein, individual biometric data/values can be captured using on-the-body sensors, then machine learning algorithms can be applied for biometric fusion. In so doing, a group measure of stress can be generated. One or more exemplary machine learning algorithms used include Gaussian Mixture Models (GMMs), Artificial Neural Networks (ANNs), Fuzzy Expert Systems (FESs), and Support Vector Machines (SVMs).

Figure 20E:
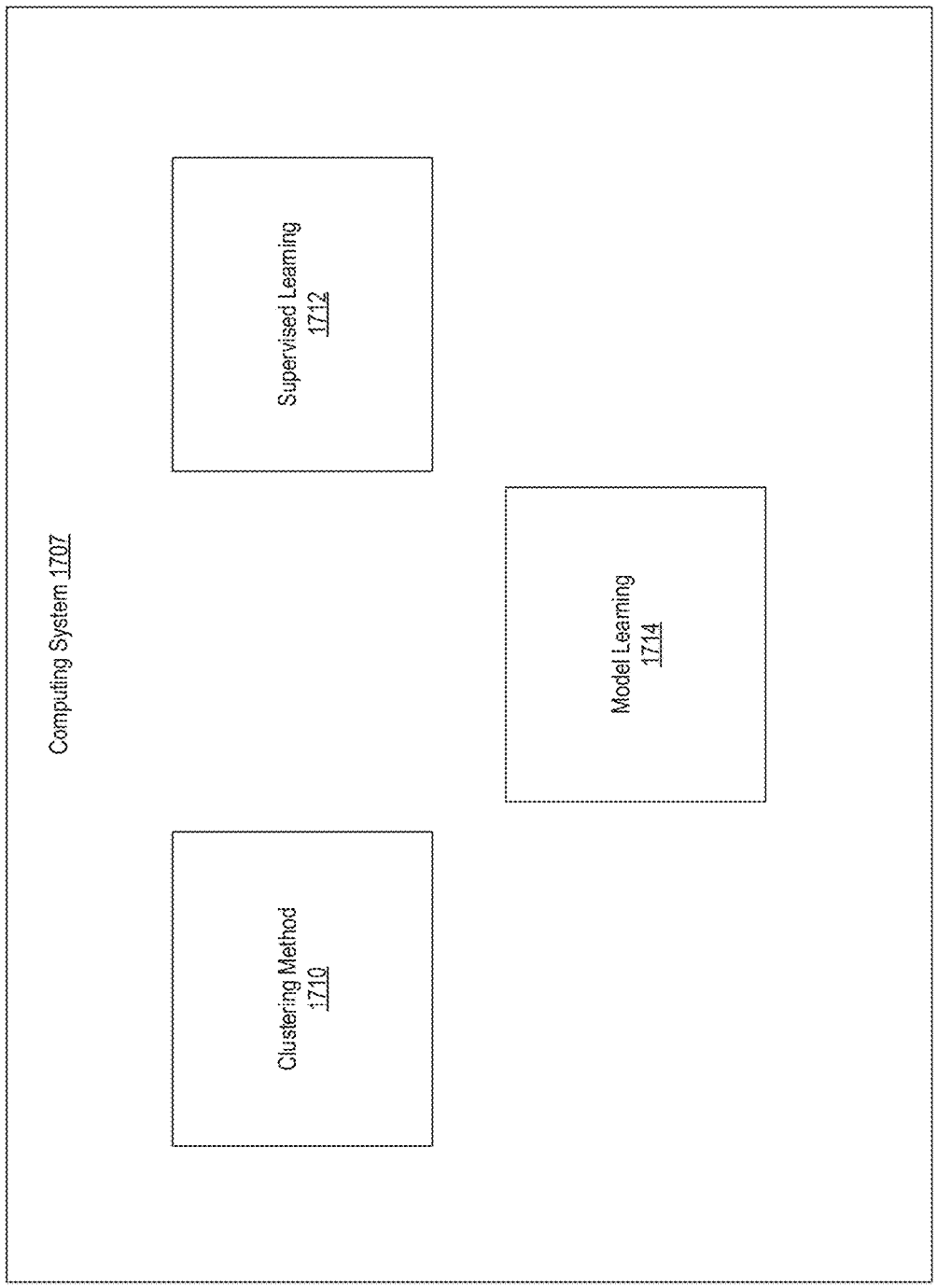
FIG. 20E is a computing system that illustrates algorithms for processing, manipulating and/or analyzing group data that has been aggregated from individual data, according to some embodiments of the disclosed technology.

FIG. 20E is a computing system 1707 that illustrates algorithms for processing, manipulating, and analyzing group data that has been aggregated, in some embodiments. In some embodiments, clustering analysis method 1710, supervised learning 1712 with data that has been aggregated and anonymized to preserve privacy, and/or model learning 1714 from published aggregated data can be used to perform the techniques and methods described herein. As previously mentioned, one or more other algorithms can be used for biometric fusion, including GMM, ANN, FES, and/or SVM.

The clustering method 1710 can be kmeans, which can be used to investigate structures of data by grouping the data into distinct subgroups. Analysis can then be performed on the subgroups to glean patterns and insight into group stress. The supervised learning 1712 can be performed on aggregated data, such as data that has been grouped using kmeans techniques. Exemplary techniques include k-nearest neighbor, neural networks, and support vector machines. The model learning 1714 can include further analysis into aggregated data, including techniques such as AQ algorithms and approaches to rule learning.

Figure 20G:
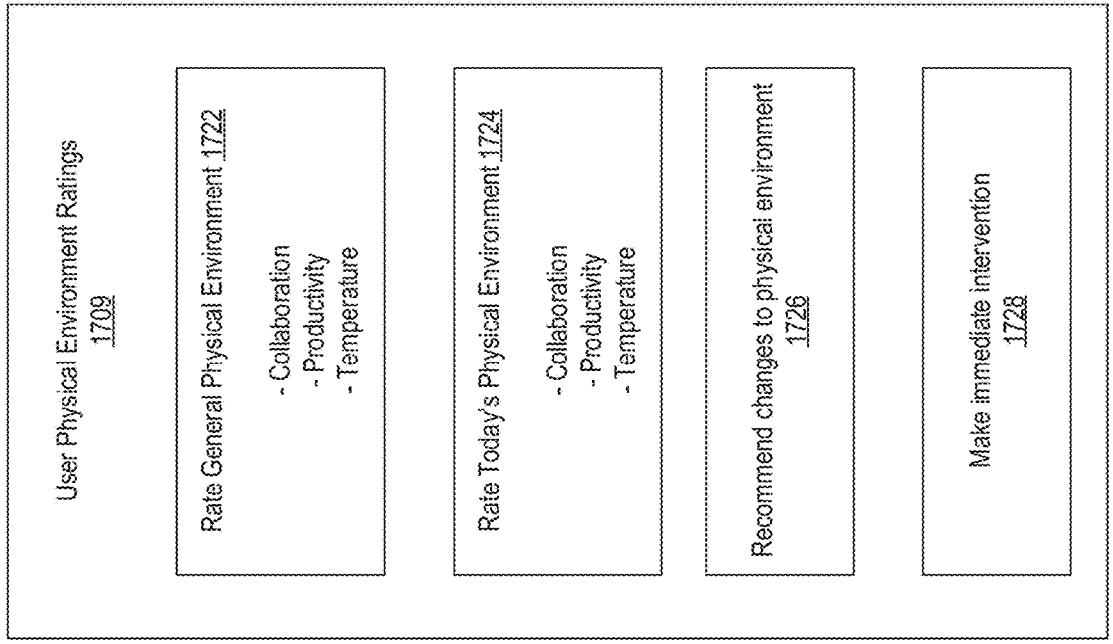
FIG. 20G is a user interface that illustrates a user-feedback app that elicits and receives self-reported data regarding physical-environment factors that affect group stress, according to some embodiments of the disclosed technology.
Figure 20F:
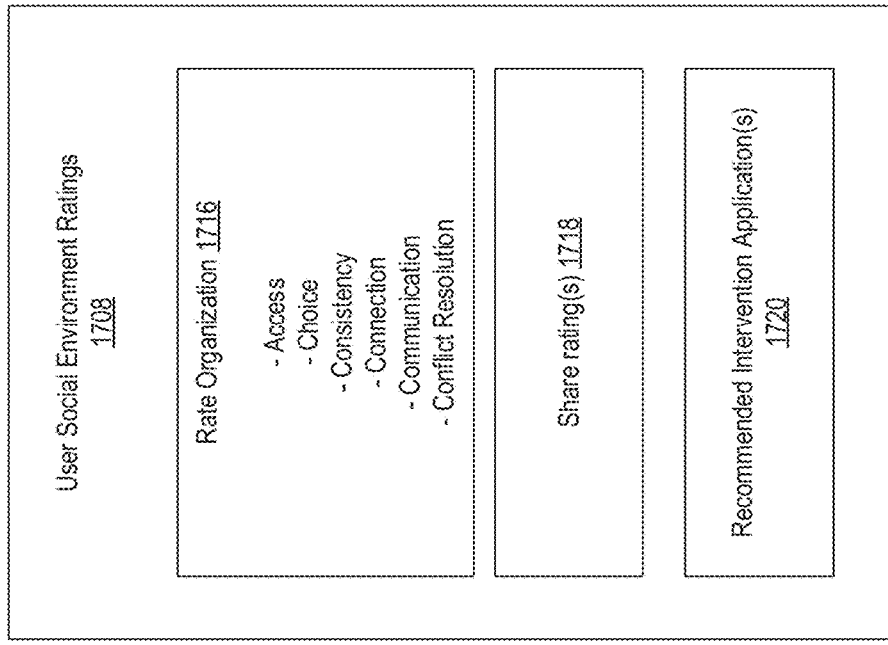
FIG. 20F is a user interface that illustrates a user-feedback app that elicits and receives self-reported data regarding social-environment factors that affect group stress, according to some embodiments of the disclosed technology.

FIG. 20F is a user interface 1708 that illustrates a user-feedback app that elicits and receives self-reported data regarding social- and/or physical-environment factors that affect collective stress, according to some embodiments of the disclosed technology. An employee rating system is critical to put power in the employees' hands. Employee feedback both tempers and gives richness and meaning to social environmental data (e.g., sensed off-the-body and on-the-body), which is automatically collected. For example, the system can prompt a user self-evaluation of social and physical environments after or concurrent with the group stress physiological readings obtained from off-body and/or on-body hardware sensors. The user feedback can be combined to determine at an overall group health score, as described throughout this disclosure. If the score is greater than a normal range for the group, then the system can recommend an application intervention based on prior efficacy of such applications in order to mitigate group stress. In some embodiments, the system can recommend an application tailored to a particular user. In some embodiments, the user can also select an intervention application.

The user interface 1708 can be presented on one or more mobile devices (e.g., user devices, input devices) of users within a physical environment. The interface 1708 can prompt the user to rate organization 1716. The organization can be rated on several different factors that are intended to measure and reduce group stress, including but not limited to access, choice, consistency, connection, communication, and conflict resolution. The user can be prompted to rate their organization weekly, bi-weekly, or during other predetermined times.

The user can share ratings 1718 across the organization (e.g., with administration, certain groups of people, and/or all employees). Once the group-level ratings are shared, individuals within the organization, such as administration, can take individual action to reduce the group stress. Moreover, intervention can be deployed (e.g., providing interactive applications to one or more mobile devices of users in the physical environment who are affected by the group stress). The user can also receive recommended intervention recommendations 1720. These can be generated by the disclosed technology and intended to be optimal interventions for the individual user in the form of personalized workspace environment adjustments and/or a tailored social environment improving app based on a comparison of a current situation to prior situations in the physical environment.

FIG. 20G is a user interface 1709 that illustrates an employee-feedback app that elicits and receives self-reported data regarding physical-environment factors that affect collective stress, according to some embodiments of the disclosed technology. The user interface 1709 can be presented on one or more devices (e.g., mobile, desktop) of users within a physical environment. The user can be prompted to rate a general physical environment 1722. This can be rating the physical environment on a macro (e.g., overall organizational level) level. In other words, the user can assess/rate how conducive the physical environment is to collaboration and/or productivity. The user can also rate a general physical environment on multiple variables that assess overall comfort and conduciveness to carrying out daily activities well or doing so with exceptionally high performance such as temperature or noise level. The user can also be prompted to rate the state of the current or today's physical environment 1724. The user can rate the current environment based on conduciveness to collaboration, productivity, and related performance-based measures as well as whether the physical conditions are comfortable and conducive to optimal performance. The user can recommend changes to the physical environment 1726. Administrators and/or other officers of the physical environment can make long-term and/or immediate interventions. The user can also make immediate intervention 1728 to improve an immediate comfort level of the physical environment of his/her own workspace, in some embodiments. In some implementations, only the user can see their individual scores, not scores of others.

FIG. 21A is a conceptual diagram that illustrates the types of physical environment output actuators used to modify parameters of the physical environment affecting the collective stress levels of group of persons, according to some embodiments of the disclosed technology. In some embodiments, the disclosed technology provides output devices, alert devices and building controls that include Dimmer—fan speed 1801B, AC or heat controller 1801N, light intensity 1801C; Infrared output—send infrared controls/signals (control devices mimicking their remote controls); Multicolor LED—shine light in any color or intensity (room lighting plant growing); Sound 1801D—playing sounds (beeps, voice announcement); Switch 1801E—switch on an electric device on or off (heater, fan, light); and/or Valve—open/close gradually (control flow of liquids, gases). In some embodiments, the actuators used to modify the building include aspects of the built environment, including movable wall partitions, sky windows, sliding doors opening to the outdoors and more.

FIG. 21B is a table 1802 that lists types of physical environment factors that affect stress in a group, according to some embodiments of the disclosed technology. As previously mentioned, some factors include but are not limited to clutter, crowds and loud noises, green space relating to mood, green space relating to mental health, aquariums and fish tanks, aromatherapy, and aroma inhalation (e.g., Bergamot aroma, Lavender, etc.), lighting, and aesthetics, such as natural textures and patterns. Positive attributes, as listed in the table 1802, can include but are not limited to window views, lighting and day light, signs of other life, ocean and park visuals whether real or not, furniture layout for social interaction, natural textures and patterns, temperature, privacy, wall openings, ceiling surface and height, aroma inhalation, expectancy of calmness, hominess, ability to move freely, green and blue spaces, and individual control of the environment. Negative attributes, as listed in the table 1820, can include but are not limited to clutter, poor lighting, crowding, loud exterior noise, inaccessible architecture, no individual control, no green or blue spaces, and low sound absorption.

Figure 22A:
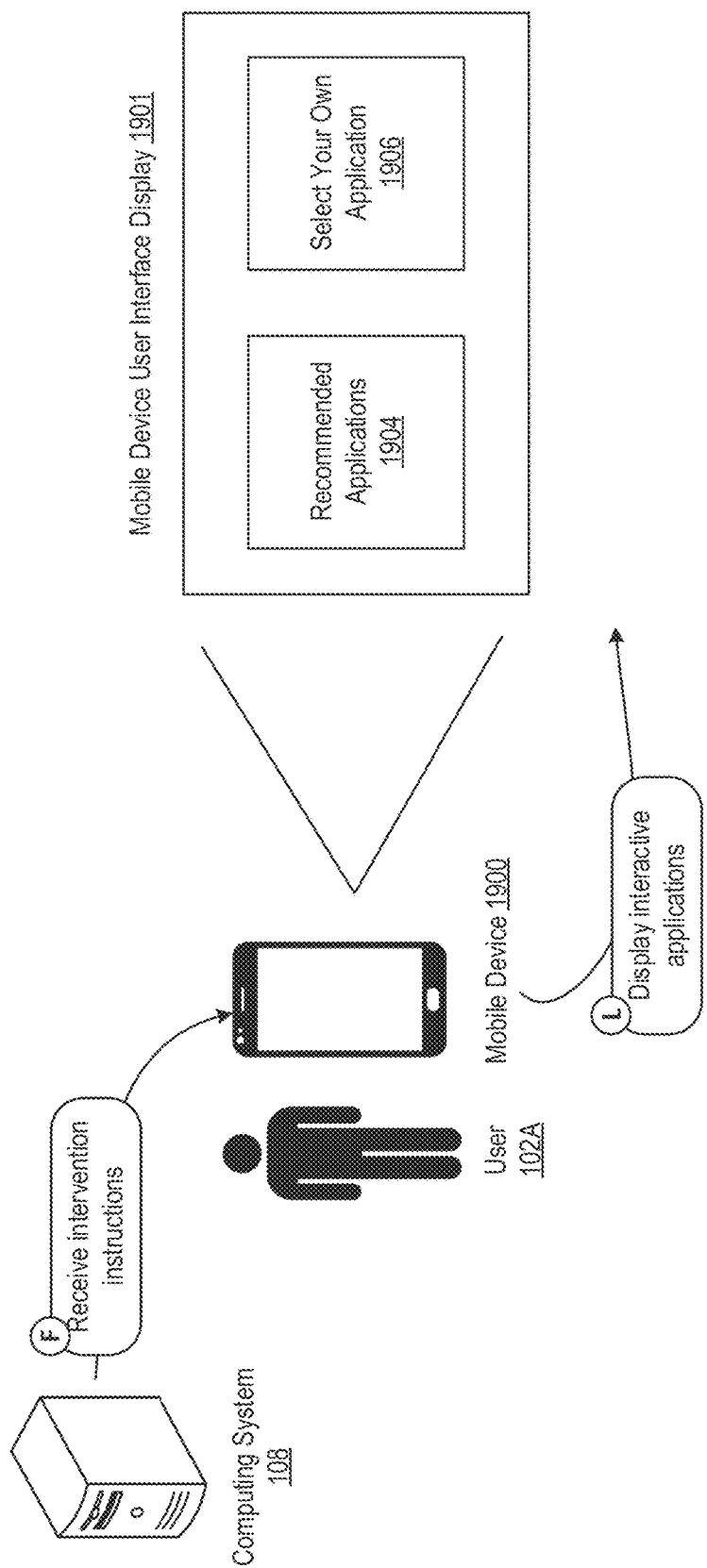
FIG. 22A is a user interface display that illustrates an app for members of a group to address social-environment (culture) drivers of collective stress, according to some embodiments of the disclosed technology.

FIG. 22A is a user interface display 1901 that illustrates an app for members of a group to address their collective stress by improving social environmental factors and processes, according to some embodiments of the disclosed technology. These apps can be designed to influence the SOCIAL ENVIRONMENT (culture) and are CONSCIOUS INTERVENTIONS, whereas the building interventions are designed to influence the PHYSICAL ENVIRONMENTS and are UNCONSCIOUS INTERVENTIONS. As depicted, when mobile device 1900 (e.g., user device) receives intervention instructions from computing system 108 (step F in FIG. 2), the device 1900 can display interactive applications in step L. The user interface display 1901 can include recommended applications 1904 and an option for the user 102A to select their top preferred app from among those available in the app sub-collections 1906. As a result, the user 102A have flexibility to select application(s) they find helpful to reduce collective stress.

Figure 22B:
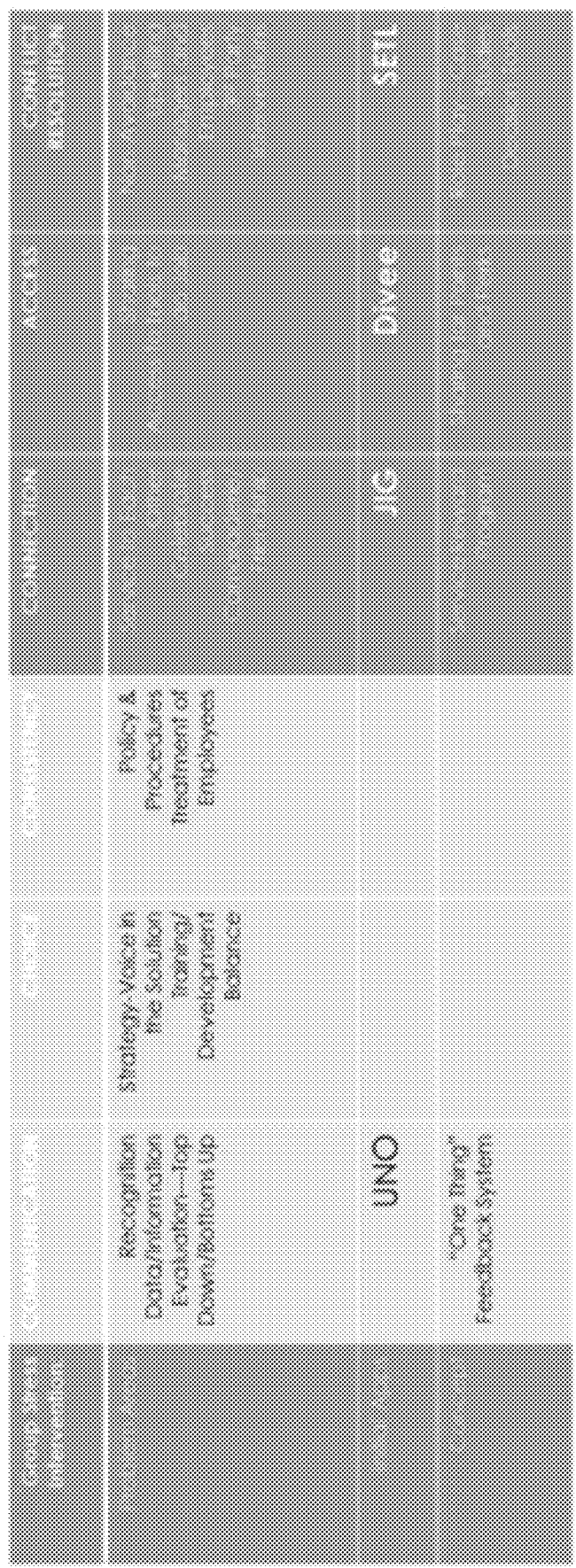
FIG. 22B is a table that illustrates intervention app properties to address collective stress driven by negative social-environment (culture) factors, according to some embodiments of the disclosed technology.

FIG. 22B is a table 1902 that illustrates some example properties of the social-environment-intervention apps designed to improve cultural issues that drive collective stress, according to some embodiments of the disclosed technology. In some embodiments, conscious interventions improve the social environment by providing apps that reduce group stressors. In some embodiments, individuals in the group can choose apps from different exemplary collective-stress-reducing areas, including communication, choice, consistency, connection, access/transparency, and conflict resolution. In some embodiments, apps are determined based on the group stress level and specific stress drivers, and all individuals in the group are presented with the same intervention app automatically by the system.

As depicted in the table 1902, an exemplary application called UNO can foster frequent, open, and honest communications by providing a "one thing" feedback system to users. Another exemplary application called JIG can increases connection and camaraderie among group members by via service rewards and recognition. An exemplary application called Divee can improve information-sharing by reinforcing positive behaviors through points and perks amongst users. An exemplary application called SETL develops conflict resolution skills by providing role play, case studies, and other interactive experiences and decision tools to the users. One or more other applications can be designed to help boost essential cultural skills, improve the social environment, and resolve group stress relating to communication, choice, consistency, connection, access, conflict resolution, and other problem areas that create high stress environments, including toxic environments. The table 1902 is not intended to be an exhaustive list of intervention application.

Figure 22C:
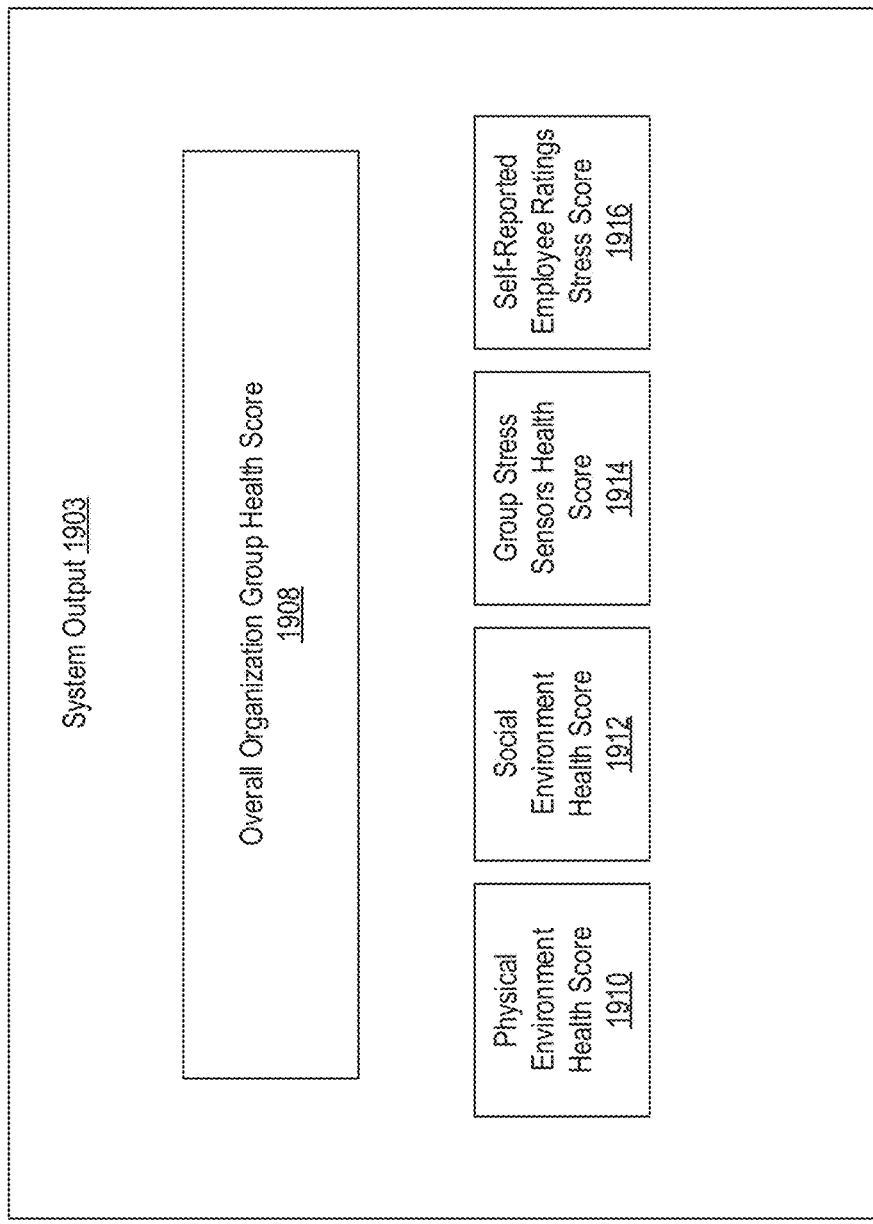
FIG. 22C is a system output that illustrates a system-reporting dashboard and software application for outputting data and enabling analysis and reporting regarding group stress levels, and physical environment and social environment (culture) factors driving elevated collective stress, according to some embodiments of the disclosed technology.

FIG. 22C is a system output 1903 that illustrates a system reporting dashboard and software application for outputting data and enabling analysis and reporting regarding physical environment and social environment factors driving elevated collective stress levels, according to some embodiments of the disclosed technology. In some embodiments, the primary dashboard report provides an overall organization group health score 1908 (which can be aggregated from measures sensed by one or more input sources or sensors, as described herein), a physical environment health score 1910, a social environment health score 1912, group stress sensors health score 1914, and a self-reported employee ratings stress score 1916. For example, the output 1903 can also display a group stress sensors score (e.g., 1914) comprised of on-the-body and off-the-body measures, and a self-reported ratings stress score 1916.

Reporting scores for each input area (e.g., physical sensors in the physical environment, off-the-body group stress sensors, on-the-body group stress sensors (opt-in by users), and self-reported user ratings) can help users and/or the computing system described herein identify where, more specifically, stresses are located outside a normal group stress state/range. The output 1903 can be displayed at one or more user devices (e.g., mobile, desktop) of users in the physical environment. The output 1903 can also be displayed at a computing system that determines collective stress levels and interventions, as described herein.

The dashboard can provide a snapshot of an organization's stress score or overall health, which can be determined using one or more measures taken from different input sources. Exemplary input sources, as described herein, include: physical sensors (e.g., traditional IoT building automation sensors that provide information regarding the current status of the physical environment), "Off-the-Body" group stress sensors (e.g., sensors that are within the environment taking readings to arrive at physiological group stress levels), "On-the-Body" sensors (e.g., "on-the-skin" wearable devices worn by the users that capture individual biometric data or "under-the-skin" sensors, then machine-learning algorithms can be applied for biometric fusion to arrive at a multimodal biometric system and group measure), and self-reported user ratings (e.g., on the social environment and physical environment). One or more different users of the organization can have permission or access to the stress scores and/or overall health scores. One or more users can also have permission to generate reports, share data, and otherwise analyze the data. In some embodiments, users can access and generate reports relating to their individual, personalized data and scores. In some embodiments, the individual data can be aggregated and anonymized to disguise individual data and to provide general group-only data and reporting.

The dashboard can capture and report stress variables that are "out of normal" bounds so that direct, immediate action can be taken (e.g., the system can automatically present an intervention application to all members of the group). In addition, the insights presented in the dashboard can enable an organization to build long-term plans to optimize a built environment and social (cultural) environment to maximize a group's mental and physical health and, as a byproduct, optimize organizational productivity and innovation. Powering the dashboard at an organizational level can be the data. One or more AI or machine learning algorithms can be used to fuse and/or cluster different biometric data in order to understand group stress, recommend, and generate effective intervention solutions. In addition, organizational data can be aggregated to a larger data set that enables data analysis and manipulation, AI, and machine learning to determine best practices to maximize organizational and social impacts.

In some embodiments, through the dashboard, a user can control the physical environment. For example, the user can recalibrate building sensors within their personal workspace to optimal settings. The system can also override the user settings when performing an intervention in order to improve a group health score or reduce group stress.

Referring to FIGS. 22A-C, one or more group intervention applications can be presented to individuals or users in a group setting. The system described herein can collect individual biometric data (e.g., via wearable sensors and/or devices) to optimize on suggesting interventions to the group and, in some embodiments, to the user that is a member of the group via tailored physical environment and social environment recommendations such as automated modifications to the user's workspace or a recommendation for a specific app from the social environment enhancing app-collection that is optimally aligned to the user. In some implementations, where individual biometric data may not be collected, group stress measurements can be captured and determined by sensors in an environment. These measurements can be used to recommend application interventions that can be provided to every member in the group experiencing group stress. Moreover, the system can capture group stress measurements once an intervention is applied to each group member so that the system can train and determine whether it provided an effective group intervention application.

In some implementations, when an intervention application is offered to the group, most of the group members may engage immediately with the application and an impact of their individual engagement on group stress can be ascertainable via a group stress read (e.g., via sensors placed in the external environment). However, in implementations where not all group members engage immediately, there can be a lag between application intervention time and an impact on the group's operating state. Therefore, group stress readings can be taken during and after application intervention to ascertain a change in the group's operating state and to determine intervention efficacy.

The intervention applications described throughout this disclosure can be advantageous to reduce group stress in a social environment, before escalation to a crisis state by improving the skills and efficacy of the individuals who comprise the group. As mentioned previously, there is a complex interplay between individuals and the environments in which they live, work, and play. As humans we are the product of our environment, but we are also parent to it. Our behaviors and the behaviors we allow (and refuse to allow) in others shape our macro environment and the various microcultures in which we spend our lives. The intervention applications in the various app sub-collections are centered on the concept of helping individuals become better group citizens, better leaders and collaborators, and build better skills in the areas that are essential to creating and sustaining the types of social and physical environments that enable individual members to thrive, groups to thrive, and individually and collectively deliver the topmost performance. The areas can be communications, conflict resolution, positive connectivity with others, enabling access to tools and information to be successful, promoting consistency, and empowering individuals by providing elements of autonomy and choice. The applications can provide for improving social environment health and/or reducing or eliminating harmful stressors in the environment that, if left unchecked, can increase the risk and likelihood of crisis situations. As an example, the applications can offer six different types of interventions (e.g., themed app sub-collections) aligned with one or more of six areas for reducing social environmental stressors that drive group stress levels (along with personal workspace and overall physical environment factors). The six areas can include: Access (e.g., transparency, sharing information, tools to do job), choice (e.g., voice in solutions, balance, self-selected training), consistency (e.g., policy and procedures, same treatment for all), connection (e.g., service to each other, camaraderie, celebrate success), communication (e.g., recognition, top down/bottoms up evaluation, data and information on strategy and plans), and conflict resolution (e.g., non-avoidance, upskilling, third-party interventions). The applications can also include methods to capture, report, share, and analyze system performance (e.g., efficacy of a system-selected intervention type). During use of any of these applications, in some embodiments, the system can also monitor biometric values of each participating group member after an app intervention has been applied. Monitoring these values can be advantageous to provide the user with further support in maximizing the benefits to oneself from the app intervention. For example, a user can receive feedback from another group member that is designed to help him/her be a better "culture player" (i.e., person that contributes to a positive social environment) but that the recipient may perceive as negative. The system can determine that the feedback perceived as negative by the user produced an elevated level of stress in the user. Therefore, the system can determine that this recipient should receive coaching intervention to help them process the feedback and insight better, and additional coaching to assist them in skill-building that would reduce or prevent the same type of negative feedback in the future. For example, the system can provide an avatar or AI coach that pops up on the recipient's screen. The avatar or coach can provide coaching in the form of words of encouragement or suggestions to improve positive cognitive processing of the feedback as well as tips and tools to apply the insight to their life and leadership approach to improve their performance and relations with others in the group.

As an example, one application in the collection can provide intervention by improving group member skills in the areas of communication and connection through acts of service. Open, honest communications and positive connectivity and relations among group members is essential to a healthy, productive social environment. This application encourages communications and user connection by encouraging, enabling, celebrating, or recognizing group members for doing something kind—an act of service. An avatar or AI smart coach can populate a screen of group members' devices and provide suggestions of acts of service to perform for other group members who have demonstrated exceptional performance or exemplary positive social-environment enhancing behaviors. These suggestions can be based on group operating state values. For example, if the group is not operating in a normal state, this application can be recommended to the group members as an intervention to improve the social environment. In some embodiments, this application intervention can be recommended to a user or subset of users based on their individual biometric data or self-report data. The AI coach can provide a suggestion to send an act, receive an act, and/or engage in an act.

Another example application in the app collection can provide intervention designed to improve information access by reducing and/or eliminating information hoarding and hiding and increasing sharing among users, while promoting group member connection, and communication This application can utilize the best practices of gaming and principles of behavior modification where employees can be rewarded for reporting and classifying their work output, making it accessible, actively sharing it, and working with others to build upon it. Group members can report positive behavior or actions. In some implementations, the group members can be prompted by an AI coach at predetermined times every week to engage in positive information sharing behavior. When the system receives input about positive behavior, the system can generate celebratory screens and/or points to provide to a group member who engaged in the positive behavior and models it for others. Such positive reinforcement can encourage similar behavior amongst other group members. Moreover, the AI coach can pop up on the user's device periodically and/or at predetermined times to provide words of encouragement or suggestions for how the user can improve their behavior. In some embodiments, the level of support provided to the user by the AI coach can be determined based on user specific data such as self-reported data indicating that this area is an area of need or development for the user. In some embodiments, all users receive words of encouragement and suggestions periodically when engaged with the app to maximize broad-based skill development.

Yet another example application in the app collection can provide intervention designed to improve skills in conflict resolution, while also boosting group communications and empowering the users with aspects of choice and autonomy. Poor conflict resolution is a major contributor to social environments that drive high group stress levels. Few workers agree that their leaders are good at preventing problems (20%), conflict management (25%), or having difficult conversations (28%).

This application can teach managers, future managers, and/or all members of a group critical skills that they need to address conflict with others in the group or lead a team through conflict. This application intervention can influence a conflict via another "system of rule" (e.g., best practices from a classroom, for example), to replace longstanding approaches under the current system of rule that are failing to deliver the desired results. The application can have three communication components. Top down evaluations keep poor leaders in power. A first component can provide for bottom up evaluations. This component can provide a simple notification/note from one group member to another to call out and intervene with early behaviors that can lead to deteriorating the social environment (e.g., passive-aggression, sarcasm, belittling others, lack of sensitivity/diversity). The sender can share the behavior, how it was hurtful, and offer to discuss further. The system can have an AI smart coach that is trained to intervene and help the recipient of the note process the feedback and respond in a healthy way. A second component can provide for positive psychology—a strengths-based intervention design that emphasizes approach versus avoidance goals. This component can allow group members to recognize other group members' abilities, accomplishments, attitudes, and virtues via a communication. A third component can provide for immediate quick-hit bursts of balanced feedback. A sender can quickly and easily share feedback with a recipient, which can encourage frequent feedback and open "low-stakes" communication. Moreover, in some implementations, users of these components can accrue points, which can be used or applied towards training and development, new software or hardware, or tools that can help the user's job, or access to others in the organization. The users can choose rewards that are most valuable to them, where that choice can also indirectly improve the social environment, by improving the skills, and favorable attitudes and perceptions, of the members in that group.

Any one or more of the components or applications described herein can have an AI or smart coach that is trained by the system. This coach can intervene and provide suggestions to members of the group. In some implementations, if the coach provides a number of alerts or suggestions that exceeds a threshold value, human coach intervention can be prompted (e.g., a trusted mentor or anonymous professional). Excessive alerts (whether positive or negative) in three months, for example, can trigger third-party intervention in a form of an Employee Assistance Program or other support, training, and/or other development program that enable free and confidential assessments, counseling, coaching, referrals, and other follow-up services to address employee needs and/or growth or advancement opportunities. Alert systems can be beneficial to raise outstanding employees up though development and promotions or prevent other employees from causing damage to a social or physical environment. The disclosed system and methods can provide for monitoring conditions in group environments and alerting members of activity that can eventually cause stress or high group stress. As a result, the system can assist in preventing group stress and predicting when it may occur.

Moreover, another application can provide intervention in consistency through data access, analysis, sharing, and reporting. For example, a human or AI coach can receive monthly history or data about best practices and issues that may have arose in the group setting. Each group member can be connected with the coach for short coaching sessions geared towards improving insight, confidence, and/or ideas for progress/action. In some embodiments, individual data can also be collected and used to improve discussion topics during these coaching sessions.

Another aspect of the disclosed technology addresses social environment and physical environment-related feedback customized to an individual in response to detected group stress caused by or particularly affecting that individual.

As mentioned, the applications can be designed to align with six effective social environment group stress mitigators. Any one application offered by the system (or selected by the user, where applicable) as an intervention can be evaluated for efficacy in real-time, providing a level of collective feedback, and individual feedback designed to optimize individual user's development and positive contributions to the social environment and physical environments. This feedback can also be used to improve the social environment and/or improve the physical environment. This feedback can fuel subsequent interventions through machine learning that, over time, lead to better and more effective interventions. The disclosed system and applications can provide for a better understanding and analysis of physical and social environmental factors that can exacerbate and also reduce group stress levels. The disclosed system and applications can also provide for identifying interventions that de-escalate group stress in the shortest amount of time.

FIG. 23 is a table 2101 that lists communications interfaces useable by various systems of the disclosed technology. For example, exemplary communication interfaces include but are not limited to AMAZON ALEXA, GOOGLE ECHO APPLY HOME, IFTTT, ZIGBEE, 4-20 MA, RS232, RS485 MODBUS, optical fiber, ARCNET, Ethernet Modbus TCP/IP, 12C, 1-Wite communication, CAN Bus, BLUETOOTH, NFC, LTE, and/or IEEE.

FIG. 24 is a description 2801 that illustrates the collective stress phenomenon as differentiated from individual stress. Strategies of adaptation to difficult and harmful social environment conditions (culture) are partly collective. Collective coping behaviors emerge in environments where collective stress is elevated. In some embodiments, a harmful collective stress response includes inaction via desensitization or conflict tolerance. As depicted, harmful collective behaviors can arise when group stress levels are elevated. In some instances, these behaviors include conflict tolerance, intention to change the situation (without action), changing the interpretation of the situation, storytelling to bring order and understanding, rationalization attempts, projection of the undesirable behaviors, resignation (e.g., psychological disengagement,) immobilization, and minimization (especially when only one person is hurt), and redefining the meaning of the situation.

Collective stress can be differentiated from individual stress. Humans tend to think of stress and anxiety as an individual phenomenon. Group stress is also a very real—but underrecognized—phenomenon that can drive harmful collective behaviors as the group members under high stress conditions seek strategies to help them adapt to difficult and harmful social environment conditions (culture), which may or may not also include poor physical environment conditions exacerbating group stressors overall. Collective coping behaviors emerge in environments where collective stress is elevated. In some embodiments, a harmful collective stress response includes inaction via desensitization or conflict tolerance.

Herd behaviors can also arise from elevated group stress. Herd behavior is a phenomenon in which individuals act collectively as part of a group, often making decisions as a group that they would not make as an individual. Herd behavior is about making a decision based in part on the behavior/choices of others.

Harmful social environments (cultures) can greatly influence or drive collective behaviors when collective stress is high. Social context (e.g., within homes, companies, organizations, or at the community level) influences how one interprets the emotional "tune" of a situation—e.g., "is there a threat or is there not a threat?" and, furthermore, influences—and even dictates—how one is supposed to act to it. Humans are social creatures by nature and have a strong desire to go with the grain, instead of against it. This characteristic of humans can lead to undesirable—and even catastrophic—outcomes when group stress is high and group behaviors and thinking supersede individual behaviors and thinking. Certain organizational cultures create conducive environments for bad behavior—e.g., unhealthy collective stress responses that can lead to devastating, irreversible outcomes including harm to oneself and others.

Social environments (culture) can be powerful to alter behaviors of individuals and groups. Social environments characterized by excessive collective stress (made worse by physical environments that drive group stressors upward) support social processes that grease the slippery slope of harmful behaviors. In some instances, these social processes include, diffusion of personal responsibility, blind obedience to authority, uncritical conformity to group norms, and passive tolerance of damaging or cruel behaviors through inaction or indifference.

FIG. 25 is a description 2802 of the cultural/social environment ingredients that transform human behaviors from positive to negative in dysfunctional and/or toxic social environments where group stress is elevated. In some embodiments, these ingredients include the identifying an acceptable justification for engaging in the undesirable action (e.g., "I'm helping them to become a better X",), insistence on fulfilling a contractual obligation (e.g., "My boss asked me to do this so I must," giving participants meaningful, "esteemed" roles (e.g., teacher,) presenting basic rules that seem to make sense prior to use, but then can be arbitrarily used to justify mindless compliance, altering the semantics of an act or action (e.g., from hurting someone to helping them to learn,), creating opportunities for others to be responsible for the outcome instead of oneself, starting the path towards ultimate acts of harm with a small, insignificant first step only, increasing each level of aggression in gradual steps that do not seem like noticeable differences, gradually changing the nature of the influence authority, and making the "exit costs" high and the process of exiting difficult.

Toxic social environments are common. Toxic workplace environments are a leading cause of workplace violence such as "violent acts, including physical assaults and threats of assault, directed toward persons at work or on duty." Verbal violence (threats, verbal abuse, hostility, harassment, and the like) can also cause significant psychological trauma and stress, even if no physical injury takes place. Verbal assaults and hostility can also escalate to physical violence, in some embodiments. Moreover, there is a direct relationship between stress and toxicity. Although working in a toxic environment can be a major source of stress in itself, stress also feeds toxicity in the workplace. The interaction between the two can create a damaging cycle if left unchecked. A powerful way to break that cycle is to reduce stress.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the disclosed technology should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A system for group-crisis state detection and intervention, the system comprising:
   a plurality of mobile devices collectively configured to:
      detect first biometric conditions specific to individual users of a plurality of users, each of the first biometric conditions identifying a health state of each of the users in the plurality of users; and
      transmit, to a computing system, the first biometric conditions;
   a plurality of sensors positioned in a physical environment where the plurality of users are located, the plurality of sensors being separate from the plurality of mobile devices, and configured to:
      detect group conditions of the plurality of users in the physical environment; and
      transmit, to the computing system, the group conditions; and
   a computing system having one or more processors, the computing system configured to:
      receive, from the plurality of mobile devices and the plurality of sensors, the first biometric and the group conditions;

associate the first biometric conditions and the group conditions as being part of conditions relevant to a group, wherein the association between the first biometric conditions and the group conditions is based on associations between (i) the plurality of users and the plurality of devices, (ii) users of the plurality of users and the plurality of users and (iii) the plurality of users and the physical environment;

identify, using one or more models, a group state of the plurality of users in the group based on the conditions relevant to the group, wherein the one or more models have threshold indicators of different group states of the plurality of users in the group, wherein the different group states include a group crisis state and a group normal state;

generate, based on identifying that the group is currently in the group crisis state, intervention instructions that are configured to be automatically executed by one or more acting devices, the intervention instructions being configured to produce actions on the one or more acting devices to lower the plurality of users collectively from the group crisis state to the group normal state;

transmit, to the one or more acting devices, the intervention instructions, wherein the one or more acting devices are configured to receive the intervention instructions from the computing system, and, in response to receiving the intervention instructions and without permission or input from the plurality of users, to automatically perform the intervention instructions on the acting devices;

receive, from the plurality of mobile devices, user input from one or more of the plurality of users identifying stressors in the physical environment; and modify, based on the user input, the intervention instructions to target the identified stressors.

2. The system of claim 1, wherein the intervention instructions include one or more of (i) adjusting one or more settings in the physical environment, (ii) providing one or more interactive applications to the plurality of users at the plurality of mobile devices, and (iii) activating communication between the plurality of users at the plurality of mobile devices and an interactive coach.

3. The system of claim 1, wherein the intervention instructions include two or more of (i) adjusting one or more settings in the physical environment, (ii) providing one or more interactive applications to the plurality of users at the plurality of mobile devices, and (iii) activating communication between the plurality of users at the plurality of mobile devices and an interactive coach.

4. The system of claim 1, wherein the intervention instructions include (i) adjusting one or more settings in the physical environment, (ii) providing one or more interactive applications to the plurality of users at the plurality of mobile devices, and (iii) activating communication between the plurality of users at the plurality of mobile devices and an interactive coach.

5. The system of claim 1, wherein the intervention instructions cause at least one of unconscious intervention or conscious intervention on the plurality of users.

6. The system of claim 1, wherein the computing system is further configured to determine the group normal state based on one or more historic first biometric conditions, historic group conditions, the detected first biometric conditions, and the detected group conditions being below a threshold value, wherein the historic and detected first biometric conditions include at least one of current physiological conditions, a breathing rate, a body temperature, skin temperature, cortisol concentration, electrodermal activity, a heartrate, a blood flow, sweat, bodily movement, volume of voice, or speaking pace and wherein the historic and detected group conditions include at least one of bodily movement, volume of voice, speaking pace, temperature of the physical environment, noise level in the physical environment, odor, location of group members in the physical environment, quantity of members in the group, or location of objects in the physical environment relative to members in the group.

7. The system of claim 1, wherein the intervention instructions include adjusting one or more settings in the physical environment including dispersing an aroma in the physical environment, adjusting a temperature of the physical environment, adjusting a lighting of the physical environment, or playing calming audio in the physical environment.

8. The system of claim 1, wherein the acting devices are configured to, in response to receiving the intervention instructions, provide a visual alert or an audible alert to the plurality of mobile devices that prompts the plurality of users to perform an action on the plurality of mobile devices, wherein the action is (i) selection of an interactive application presented at each of the plurality of mobile devices or (ii) performing actions in an interactive application that was selected by the computing system based on the group crisis state exceeding a threshold level.

9. The system of claim 8, wherein the computing system is configured to select the interactive application based on determining, from the one or more models, that the group crisis state is above a threshold indicator of a group crisis state.

10. The system of claim 8, wherein the interactive application includes instructions prompting the plurality of users to perform actions at the plurality of mobile devices that are intended to collectively lower the plurality of users in the group from the group crisis state to the group normal state, the actions including (i) engaging in an online conflict resolution application between the plurality of users and an artificial intelligence (AI) mediator, (ii) playing a game with one or more of the plurality of users, (iii) performing an act of service for one or more of the plurality of users, (iv) providing positive feedback to one or more of the plurality of users, or (v) providing negative feedback to one or more of the plurality of users.

11. The system of claim 1, wherein the one or more acting devices are configured to (i) execute the intervention instructions while the detected first biometric conditions and the group conditions exceed a threshold value indicative that the plurality of users in the group are operating in the group crisis state and (ii) terminate the intervention instructions when the detected first biometric conditions and the group conditions are lower than the threshold value.

12. The system of claim 1, wherein the intervention instructions include activating communication between the plurality of users at the plurality of mobile devices and an interactive coach, the interactive coach being an artificial intelligence (AI) coach that is trained, by the computing system and using machine learning, based on historic crisis interventions for the plurality of users in the group.

13. The system of claim 1, wherein the acting devices are configured to, in response to receiving the intervention instructions from the computing system, uniformly execute the intervention instructions at the plurality of mobile devices for the plurality of users in the group.

14. The system of claim 1, wherein the acting devices are configured to, in response to receiving the intervention instructions from the computing system, modify the intervention instructions at each of the plurality of mobile devices for each of the plurality of users in the group based on the first biometric conditions for each of the plurality of users.

15. The system of claim 1, wherein the computing system is further configured to:
predict, using machine learning and the one or more models having threshold indicators of different group states of the plurality of users in the group, when the group will enter the group crisis state; and
generate second intervention instructions that are configured to be automatically executed by the acting devices, the second intervention instructions being configured to produce an action on the acting devices to maintain the plurality of users in the group in the group normal state.

16. The system of claim 1, wherein the acting devices include the plurality of mobile devices, the one or more sensors in the physical environment, and a building computing system, wherein the building computing system is configured to adjust one or more conditions of the physical environment.

17. A system for group-crisis state detection and intervention, the system comprising:
a plurality of mobile devices collectively configured to:
detect first biometric conditions specific to individual users of a plurality of users, each of the first biometric conditions identifying a health state of each of the users in the plurality of users; and
transmit, to a computing system, the first biometric conditions;
a plurality of sensors positioned in a physical environment where the plurality of users are located, the plurality of sensors being separate from the plurality of mobile devices, and configured to:
detect group conditions of the plurality of users in the physical environment; and
transmit, to the computing system, the group conditions; and
a computing system having one or more processors, the computing system configured to:
receive, from the plurality of mobile devices and the plurality of sensors, the first biometric and the group conditions;
associate the first biometric conditions and the group conditions as being part of conditions relevant to a group, wherein the association between the first biometric conditions and the group conditions is based on associations between (i) the plurality of users and the plurality of devices, (ii) users of the plurality of users and the plurality of users and (iii) the plurality of users and the physical environment;
identify, using one or more models, a group state of the plurality of users in the group based on the conditions relevant to the group, wherein the one or more models have threshold indicators of different group states of the plurality of users in the group, wherein the different group states include a group crisis state and a group normal state;
generate, based on identifying that the group is currently in the group crisis state, intervention instructions that are configured to be automatically executed by one or more acting devices, the intervention instructions being configured to produce actions on the one or more acting devices to lower the plurality of users collectively from the group crisis state to the group normal state;
transmit, to the one or more acting devices, the intervention instructions, wherein the one or more acting devices are configured to receive the intervention instructions from the computing system, and, in response to receiving the intervention instructions and without permission or input from the plurality of users, to automatically perform the intervention instructions on the acting devices; and
train the one or more models having threshold indicators of different group states of the of the plurality of users in the group based on the detected first biometric conditions and group conditions, executed intervention instructions, an amount of time taken to lower the group from the group crisis state to the group normal state, and an efficacy score of the executed intervention instructions.

18. The system of claim 17, wherein the intervention instructions include one or more of (i) adjusting one or more settings in the physical environment, (ii) providing one or more interactive applications to the plurality of users at the plurality of mobile devices, and (iii) activating communication between the plurality of users at the plurality of mobile devices and an interactive coach.

19. A system for group-crisis state detection and intervention, the system comprising:
a plurality of mobile devices collectively configured to:
detect first biometric conditions specific to individual users of a plurality of users, each of the first biometric conditions identifying a health state of each of the users in the plurality of users; and
transmit, to a computing system, the first biometric conditions;
a plurality of sensors positioned in a physical environment where the plurality of users are located, the plurality of sensors being separate from the plurality of mobile devices, and configured to:
detect group conditions of the plurality of users in the physical environment; and
transmit, to the computing system, the group conditions; and
a computing system having one or more processors, the computing system configured to:
receive, from the plurality of mobile devices and the plurality of sensors, the first biometric and the group conditions;
associate the first biometric conditions and the group conditions as being part of conditions relevant to a group, wherein the association between the first biometric conditions and the group conditions is based on associations between (i) the plurality of users and the plurality of devices, (ii) users of the plurality of users and the plurality of users and (iii) the plurality of users and the physical environment;
identify, using one or more models, a group state of the plurality of users in the group based on the conditions relevant to the group, wherein the one or more models have threshold indicators of different group states of the plurality of users in the group, wherein the different group states include a group crisis state and a group normal state;
generate, based on identifying that the group is currently in the group crisis state, intervention instructions that are configured to be automatically executed by one or more acting devices, the intervention instructions being configured to produce actions on the one or more acting devices to lower the plurality of users collectively from the group crisis state to the group normal state;

transmit, to the one or more acting devices, the intervention instructions, wherein the one or more acting devices are configured to receive the intervention instructions from the computing system, and, in response to receiving the intervention instructions and without permission or input from the plurality of users, to automatically perform the intervention instructions on the acting devices; and determine an efficacy score for executed intervention instructions in lowering the plurality of users in the group from the group crisis state to the group normal state, wherein the efficacy score is based on an amount of time taken to lower plurality of users in the group from the group crisis state to the group normal state being less than a threshold value.

20. The system of claim 19, wherein the intervention instructions include one or more of (i) adjusting one or more settings in the physical environment, (ii) providing one or more interactive applications to the plurality of users at the plurality of mobile devices, and (iii) activating communication between the plurality of users at the plurality of mobile devices and an interactive coach.

* * * * *